United States Patent
Hoss et al.

(10) Patent No.: US 12,239,442 B2
(45) Date of Patent: Mar. 4, 2025

(54) ANALYTE SENSORS WITH REDUCED INTERFERENT SIGNAL AND METHODS

(71) Applicant: ABBOTT DIABETES CARE INC., Alameda, CA (US)

(72) Inventors: Udo Hoss, San Ramon, CA (US); Tianmei Ouyang, Fremont, CA (US); Benjamin J. Feldman, Berkeley, CA (US); Suyue Qian, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 354 days.

(21) Appl. No.: 17/348,169

(22) Filed: Jun. 15, 2021

(65) Prior Publication Data

US 2022/0192550 A1    Jun. 23, 2022

Related U.S. Application Data

(60) Provisional application No. 63/129,874, filed on Dec. 23, 2020.

(51) Int. Cl.
*A61B 5/1486* (2006.01)
*A61B 5/145* (2006.01)

(52) U.S. Cl.
CPC ...... *A61B 5/14865* (2013.01); *A61B 5/14532* (2013.01); *A61B 2562/125* (2013.01)

(58) Field of Classification Search
CPC ............ A61B 5/14865; A61B 5/14532; A61B 2562/125; A61B 5/6898
See application file for complete search history.

(56) References Cited

U.S. PATENT DOCUMENTS

| | | | |
|---|---|---|---|
| 5,089,112 A | 2/1992 | Skotheim et al. |
| 5,165,407 A | 11/1992 | Wilson et al. |
| 5,322,063 A | 6/1994 | Allen et al. |
| 5,390,671 A | 2/1995 | Lord et al. |
| 5,569,186 A | 10/1996 | Lord et al. |
| 5,584,813 A | 12/1996 | Livingston et al. |
| 5,849,174 A | 12/1998 | Sanghera et al. |
| 6,103,033 A | 8/2000 | Say et al. |

(Continued)

FOREIGN PATENT DOCUMENTS

| | | |
|---|---|---|
| DK | PA 2004 01265 | 8/2004 |
| EP | 0 838 230 A2 | 4/1998 |

(Continued)

OTHER PUBLICATIONS

Chen et al., "Defining the Period of Recovery of the Glucose Concentration after Its Local Perturbation by the Implantation of a Miniature Sensor," Clin Chem Lab Med 40(8):786-789 (2002).

(Continued)

*Primary Examiner* — Jay B Shah
(74) *Attorney, Agent, or Firm* — Baker Botts L.L.P.

(57) ABSTRACT

Analyte sensor comprises an electrode layer having an elongate body comprising a proximal end and a distal end. The electrode layer includes a first active working electrode area, a second electrode portion, and at least one gap electrically separating the first active working electrode portion and the second electrode portion. The first active working electrode area comprises at least one sensing spot with at least one analyte responsive enzyme disposed thereupon. Additional analyte sensors disclosed.

39 Claims, 27 Drawing Sheets

(56) References Cited

U.S. PATENT DOCUMENTS

| | | | |
|---|---|---|---|
| 6,134,461 A | 10/2000 | Say et al. | |
| 6,237,394 B1 | 5/2001 | Harris et al. | |
| 6,424,847 B1 | 7/2002 | Mastrototaro et al. | |
| 6,565,509 B1 | 5/2003 | Say et al. | |
| 6,605,200 B1 | 8/2003 | Mao et al. | |
| 6,605,201 B1 | 8/2003 | Mao et al. | |
| 6,673,022 B1 | 1/2004 | Bobo et al. | |
| 6,736,957 B1 | 5/2004 | Forrow et al. | |
| 6,809,653 B1 | 10/2004 | Mann et al. | |
| 6,850,859 B1 | 2/2005 | Schuh | |
| 6,931,327 B2 | 8/2005 | Goode, Jr. et al. | |
| 6,990,366 B2 | 1/2006 | Say et al. | |
| 7,299,082 B2 | 11/2007 | Feldman et al. | |
| 7,323,142 B2 | 1/2008 | Pendo et al. | |
| 7,501,053 B2 | 3/2009 | Karinka et al. | |
| 7,725,148 B2 | 5/2010 | Shah et al. | |
| 7,754,093 B2 | 7/2010 | Forrow et al. | |
| 8,268,143 B2 | 9/2012 | Liu et al. | |
| 8,280,474 B2 | 10/2012 | Liu et al. | |
| 8,444,834 B2 | 5/2013 | Liu et al. | |
| 8,983,568 B2 | 3/2015 | Bommakanti et al. | |
| 9,241,631 B2 | 1/2016 | Valdes et al. | |
| 9,504,471 B2 | 11/2016 | Vaitekunas et al. | |
| 9,788,766 B2 | 10/2017 | Simpson et al. | |
| 9,808,574 B2 | 11/2017 | Yodfat et al. | |
| 10,820,842 B2 | 11/2020 | Harper | |
| 10,827,954 B2 | 11/2020 | Hoss et al. | |
| 10,874,338 B2 | 12/2020 | Stafford | |
| 10,881,341 B1 | 1/2021 | Curry et al. | |
| 10,945,647 B2 | 3/2021 | Mazza et al. | |
| 10,945,649 B2 | 3/2021 | Lee et al. | |
| 10,952,653 B2 | 3/2021 | Harper | |
| 10,959,654 B2 | 3/2021 | Curry et al. | |
| 10,966,644 B2 | 4/2021 | Stafford | |
| 10,973,443 B2 | 4/2021 | Funderburk et al. | |
| 10,980,461 B2 | 4/2021 | Simpson et al. | |
| 11,000,213 B2 | 5/2021 | Kamath et al. | |
| 11,000,216 B2 | 5/2021 | Curry et al. | |
| 11,013,440 B2 | 5/2021 | Lee et al. | |
| 11,064,917 B2 | 7/2021 | Simpson et al. | |
| 11,141,084 B2 | 10/2021 | Funderburk et al. | |
| 2002/0161288 A1 | 10/2002 | Shin et al. | |
| 2002/0169369 A1 | 11/2002 | Ward et al. | |
| 2003/0042137 A1 | 3/2003 | Mao et al. | |
| 2003/0097082 A1 | 5/2003 | Purdy et al. | |
| 2003/0114836 A1 | 6/2003 | Estes et al. | |
| 2003/0225361 A1 | 12/2003 | Sabra | |
| 2004/0061232 A1 | 4/2004 | Shah et al. | |
| 2004/0087876 A1 | 5/2004 | Eskuri | |
| 2005/0027181 A1 | 2/2005 | Goode, Jr. et al. | |
| 2005/0038332 A1 | 2/2005 | Saidara et al. | |
| 2005/0215871 A1 | 9/2005 | Feldman et al. | |
| 2005/0245799 A1 | 11/2005 | Brauker et al. | |
| 2006/0020187 A1 | 1/2006 | Brister et al. | |
| 2006/0094944 A1 | 5/2006 | Chuang | |
| 2006/0142651 A1 | 6/2006 | Brister et al. | |
| 2006/0200982 A1 | 9/2006 | Bhullar et al. | |
| 2006/0257996 A1 | 11/2006 | Simpson et al. | |
| 2006/0258959 A1 | 11/2006 | Sode | |
| 2008/0161666 A1 | 7/2008 | Feldman et al. | |
| 2008/0172205 A1 | 7/2008 | Breton et al. | |
| 2008/0194990 A1 | 8/2008 | Heller et al. | |
| 2008/0319414 A1 | 12/2008 | Yodfat et al. | |
| 2009/0076360 A1 | 3/2009 | Brister et al. | |
| 2009/0099521 A1 | 4/2009 | Gravesen et al. | |
| 2009/0102678 A1 | 4/2009 | Mazza et al. | |
| 2009/0178459 A1 | 7/2009 | Li et al. | |
| 2010/0145377 A1 | 6/2010 | Lai et al. | |
| 2010/0193484 A1 | 8/2010 | Chen et al. | |
| 2010/0230285 A1 | 9/2010 | Hoss et al. | |
| 2010/0286496 A1 | 11/2010 | Simpson et al. | |
| 2011/0213225 A1 | 9/2011 | Bernstein et al. | |
| 2012/0150005 A1 | 6/2012 | Hoss et al. | |
| 2013/0345534 A1* | 12/2013 | Hoss | A61B 5/1468 600/345 |
| 2015/0005601 A1 | 1/2015 | Hoss et al. | |
| 2015/0094554 A1 | 4/2015 | Heller et al. | |
| 2015/0298124 A1 | 10/2015 | Fischer et al. | |
| 2015/0351690 A1 | 12/2015 | Toth et al. | |
| 2016/0235347 A1 | 8/2016 | Baig et al. | |
| 2017/0107555 A1 | 4/2017 | Katsuki et al. | |
| 2017/0112531 A1 | 4/2017 | Schoonmaker et al. | |
| 2017/0188908 A1 | 7/2017 | Hoss et al. | |
| 2017/0265795 A1 | 9/2017 | Boock et al. | |
| 2017/0273610 A1 | 9/2017 | Suri et al. | |
| 2017/0363564 A1 | 12/2017 | Hoss et al. | |
| 2018/0199873 A1 | 7/2018 | Wang et al. | |
| 2018/0328877 A1 | 11/2018 | Vaddiraju et al. | |
| 2019/0125230 A1 | 5/2019 | Feldman | |
| 2019/0175083 A1 | 6/2019 | Cohen et al. | |
| 2019/0216374 A1 | 7/2019 | Hoss et al. | |
| 2019/0261907 A1 | 8/2019 | Brister et al. | |
| 2019/0298232 A1* | 10/2019 | Ko | H05K 1/181 |
| 2019/0310222 A1 | 10/2019 | Boock | |
| 2019/0320947 A1 | 10/2019 | Chen et al. | |
| 2019/0326501 A1 | 10/2019 | Gilbert et al. | |
| 2020/0022670 A1 | 1/2020 | Eibl et al. | |
| 2020/0060592 A1 | 2/2020 | Feldman et al. | |
| 2020/0146595 A1 | 5/2020 | Simpson et al. | |
| 2020/0178862 A1 | 6/2020 | Brister | |
| 2020/0178864 A1 | 6/2020 | Cui et al. | |
| 2020/0237275 A1 | 7/2020 | Feldman et al. | |
| 2020/0237277 A1 | 7/2020 | Ouyang et al. | |
| 2020/0241015 A1 | 7/2020 | Ouyang et al. | |

FOREIGN PATENT DOCUMENTS

| | | |
|---|---|---|
| GB | 2 067 764 A | 7/1981 |
| WO | WO 98/56293 A1 | 12/1998 |
| WO | WO 99/56613 A1 | 11/1999 |
| WO | WO 03/056319 A2 | 7/2003 |
| WO | WO 2004/088275 A2 | 10/2004 |
| WO | WO 2006/018447 A2 | 2/2006 |
| WO | WO 2006/042811 A2 | 4/2006 |
| WO | WO 2010/091005 A1 | 8/2010 |

OTHER PUBLICATIONS

DCU Conferences, Nov. 2003, 8 pgs.
Declaration of John Mastrototaro, PH.D., 205 pgs. (Sep. 29, 2022).
Dexcom 10K, 59 pgs. (2005).
DexCom CGM Resource Center References Bibliography, 14 pgs. (Jun. 12, 2011).
Dexcom SEC Form, S-1-2005, 309 pgs. (Feb. 1, 2005).
Diabetes Abstract Book, 53(2):1-12 (Jun. 2004).
FDA Notice—Determination of Regulatory, Federal Registry 86(211):60827-60829 (Nov. 4, 2021) 3 pgs.
FDA Premarket Approval (PMA) for Freestyle Navigator Continuous Glucose Monitor, Jan. 23, 2022, 6 pgs.
Feldman et al., "A Continuous Glucose Sensor Based on Wired Enzyme Technology—Results from a 3-Day Trial in Patients with Type 1 Diabetes," Diabetes Technology & Thgerapeutics 5(5):769-779 (2003).
Freestyle Navigator User Guide, (Mar. 6, 2000) 38 pgs.
Heinemann et al., "Benefits and Limitations of MARD as a Performance Parameter for Continuous Glucose Monitoring in the Interstitial Space," Journal of Diabetes Science and Technology 14(1):135-150 (2020).
Heller et al., "Electrochemical Glucose Sensors and Their Applications in Diabetes Management," Chem. Rev. 108:2482-2505 (2008).
Heller et al., "Electrochemistry in Diabetes Management," Accounts of Chemical Research 43(7):963-973 (2010).
Heller, "Integrated Medical Feedback Systems for Drug Delivery," AIChE Journal 51(4):1054-1066 (2005).
International Search Report and Written Opinion mailed Sep. 24, 2021 in International Application No. PCT/US2021/037307.
International Search Report and Written Opinion mailed Sep. 24, 2021 in International Application No. PCT/US2021/037309.

(56) References Cited

OTHER PUBLICATIONS

International Search Report and Written Opinion mailed Sep. 23, 2021 in International Application No. PCT/US2021/037313.
International Search Report and Written Opinion mailed Sep. 24, 2021 in International Application No. PCT/US2021/037322.
Kovatchev et al., "Evaluating the Accuracy of Continuous Glucose-Monitoring Sensors," Diabetes Care 27:1922-1928 (2004).
Original Premarket Approval Application (Jun. 2005), 61 pgs.
Premarket Approval Application Amendment (May 2006), 89 pgs.
Reiterer et al., "Significance and Reliability of MARD for the Accuracy of CGM Systems," Journal of Diabetes Science and Technology 11(1):59-67 (2017).
Therasense Navigates Continuous Glucose Monitor PMA, Prepares for Flash, The Gray Sheet 29(37):18 (2003), 2 pgs.
Ward et al., "A Wire-Based Dual-Analyte Sensor for Glucose and Lactate: In Vitro and In Vivo Evaluation," Diabetes Technology & Therapeutics 6(3):389-401 (2004).
Website—Abbotts Continuous Blood Glucose Monitor Approval Soon, Oct. 3, 2006, 3 pgs.
Website—Children w Diabetes-Report from Diabetes Tech, Jan. 21, 2022, 3 pgs.
Website—Dexcom Leading the Way Brochure, 2009, 12 pgs.
Website—TheraSense Files Premarket Approval Application for Freestyle Navigator, Dec. 13, 2003, 3 pgs.
Wilson et al., "Introduction to the Glucose Sensing Problem," Chapter 1 (2010) 27 pgs.
U.S. Appl. No. 17/347,829, filed Jun. 15, 2021.
U.S. Appl. No. 17/347,869, filed Jun. 15, 2021.
U.S. Appl. No. 17/347,845, filed Jun. 15, 2021.
Khan et al., "Kinetics of the reduction of water-soluble colloidal $MnO_2$ by ascorbic acid," Journal of Colloid and Interface Science 290:184-189 (2005).
U.S. Appl. No. 60/490,208, filed Jul. 25, 2003, Simpson.
U.S. Appl. No. 17/347,869, filed Oct. 25, 2022 Non-Final Office Action.
U.S. Appl. No. 17/347,845, filed Dec. 22, 2022 Non-Final Office Action.
Cho et al., "The TheraSense, Inc. Continuous Glucose Monitor: Preliminary Clinical Results from a Subcutaneous Sensor with a Wireless Connection to a Hand-Held Display/Alarm," Clinical Therapeutics/New Technology—Glucose Monitoring and Sensing, 392-P, A91 (2003).
Craston et al., "Microband Electrodes Fabricated by Screen Printing Processes: Applications in Electroanalysis," Talanta, vol. 38, No. 1, 17-26 (1991).
"Abbott Receives CE Mark for Freestyle® Libre, A Revolutionary Glucose Monitoring System for People with Diabetes," 8 pages (2023).
"FDA authorizes first fully interoperable continuous glucose monitoring system, streamlines review pathway for similar devices," FDA News Release, retrieved from https://www.fda.gov/news-events/press-announcements/fda-authorizes-first-fully-interoperable-continuous-glucose-monitoring-system-streamlines-review on Mar. 27, 2018, 3 pages.
ATTD Program, 4 pages (2009).
Cambridge Dictionary of American English, 3 pages (2000)—Recess.
Dexcom (DXCM) Company Profile, 2017 /Q4 Earnings call transcript, 12 pages (2017).
DexCom (DXCM) Q1 2018 Results—Earnings Call Transcript retrieved from https://seekingalpha.com/article/4168949-dexcom-dxcm-q1-2018-results-earnings-call-transcript on May 2, 2018, 4 pages.
Dexcom G6 Continuous Glucose Monitoring System User Guide, 7 pages (2020).
Dexcomg6, Continuous Glucose Monitoring System, User Guide, 22 pages (2020).
Dexcomg6, Start Here, Set up, Dexcom G6 Continuous Glucose Monitoring (CGM) System (G6), 8 pages (2019).
Dexcomg6, Using Your G6, 7 pages (2020).
Drawing Sheets for U.S. Pat. No. 10,973,443 issued Apr. 13, 2021, 2 pages.
Email communication from Sophie Hood, Jan. 24, 2023, 6 pages.
Excerpts from Expert Report of Catharine M. Lawton—Ex. 36, Spruce Point Capital Management, Does Dexcom Really Have A Future If It Can't Match Abbott's Scale? 2 pages, Mar. 21, 2019.
Hall, Interview with Kevin Sayer, President and CEO of Dexcom About The New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, 23 pages (2009).
Hoss, et al., "Continuous Glucose Monitoring in Subcutaneous Tissue Using Factory—Calibrated Sensors: A Pilot Study", Diabetes Technology & Therapeutics, 12(8):591-597 (2010).
Hoss, et al., "Feasibility of Factory Calibration for Subcutaneous Glucose Sensors in Subjects With Diabetes", Journal of Diabetes Science and Technology, 8(1):89-94 (2014).
IEEE 100, The Authoritative Dictionary of IEEE Standards Terms, $7^{th}$ Ed., 3 pages (2000).
Interview with Dexcom CEO, Dexcom CEO Kevin Sayer Explains G6, Written By: Michelle Boise, 9 pages (2018).
Joint Declaration of Funderburk, et al. for U.S. Appl. No. 15/963,828, 11 pages (2020).
Letter from the Department of Health & Human Services, Food and Drug Administration to Abbott Diabetes Care, Inc. dated Mar. 12, 2008, regarding the Premarket Approval Application (PMA) for the FreeStyle Navigator Continuous Glucose Monitoring System, 7 pages.
Merriam-Webster's Collegiate Dictionary, $10^{th}$ Ed., 4 pages (1999)—Housing and recess.
Merriam-Webster's Collegiate Dictionary, $10^{th}$ Ed., 4 pages (1999)—Release and retain.
Non-Final Office Action for U.S. Appl. No. 14/884,622 dated Jun. 13, 2018, 7 pages.
Non-Final Office Action for U.S. Appl. No. 17/030,030 dated Dec. 17, 2020, 7 pages.
Notice of Allowance for U.S. Appl. No. 15/963,828 dated Mar. 3, 2021, 32 pages.
Omnipod image, Exhibit 182, 2 pages, Sep. 22, 2022.
Response to Non-Final Office Action for U.S. Appl. No. 15/963,828, filed Dec. 8, 2020, 17 pages.
Response to Restriction Requirement for U.S. Appl. No. 14/884,622, filed Apr. 5, 2018, 15 pages.
S&P Global Market Intelligence "DeXCom, Inc. NasdaqGS:DXCM, Company Conference Presentation," 17 pages (2021).
S&P Global Market Intelligence "DeXCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Sayer, CGMS Changing Diabetes Management: Kevin Sayer, DIC Interview Transcript, Featuring Steve Freed, 11 pages (2019).
Sonix, Dexcom CEO—Prime Position in Our Market—Mad Money—CNBC.mp4, 4 pages (2023).
Tegnestedt, et al., "Levels and sources of sound in the intensive care unit—an observational study of three room types", Acta Anaesthesiologica Scandinavica, pp. 1-10 (2013).
The Chambers Dictionary, 4 pages (1998)—Retract.
The MiniMed Paradigm® REAL-Time Insulin Pump and Continuous Glucose Monitoring System, Insulin Pump User Guide, Paradigm® 522 and 722 Insulin Pumps, Medtronic MiniMed, Inc., 25 pages (2008).
The New Oxford American Dictionary, 3 pages (2001)—Retract.
The New Penguin English Dictionary, Penguin Books, 4 pages (2000)—Recess.
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Software Change to an Existing Device, Guidance for Industry and Food and Drug Administration Staff," 32 pages (2017).
Watkin, "An Introduction to Flash Glucose Monitoring," 16 pages (2013).

(56) References Cited

OTHER PUBLICATIONS

Webster's New College Dictionary, 2 pages (2001)—Alcove.
Webster's Third New International Dictionary, 5 pages (1993)—Retract.
Chen, et al., "A novel fault-tolerant sensor system for sensor drift compensation", Sensors and Actuators, A 147:623-632 (2008).
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Gerritsen, et al., "Performance of subcutaneously implanted glucose sensors for continuous monitoring", The Netherlands Journal of Medicine, 54:167-179 (1999).
Guardian® Real-Time, Continuous Glucose Monitoring System, User Guide, Medtronic MiniMed, Inc., 181 pages (2006).
Guardian® RT, Continuous Glucose Monitoring System, REF MMT-7900, User Guide, Medtronic MiniMed, 128 pages (2005).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
U.S. Appl. No. 61/155,889, filed Feb. 26, 2009, Hoss, et al.
Brückel, et al., "In Vivo Measurement of Subcutaneous Glucose Concentrations with an Enzymatic Glucose Sensor and a Wick Method", Klin Wochenschr, 67:491-495 (1989).
U.S. Appl. No. 61/155,889.
FreeStyle Navigator Continuous Glucose Monitoring System, User's Guide, Abbott Diabetes Care Inc., 38 pages (2008).
Guardian® REAL-Time, Continuous Glucose Monitoring System, User Guide, Medtronic MiniMed, Inc., 184 pages (2006).
Mastrototaro, et al., "An electroenzymatic glucose sensor fabricated on a flexible substrate", Sensors and Actuators B, 5:139-144 (1991).
FreeStyle Navigator Continuous Glucose Monitoring System, Dept of Health & Human Services, Food and Drug Administration, Mar. 12, 2008, 8 pages.
U.S. Appl. No. 17/347,829, filed Nov. 8, 2023 Final Office Action.
U.S. Appl. No. 17/347,845, filed Nov. 22, 2023 Non-Final Office Action.
U.S. Appl. No. 17/347,869, filed Dec. 7, 2023 Non-Final Office Action.
U.S. Appl. No. 17/347,869, filed Jun. 10, 2024 Final Office Action.
U.S. Appl. No. 17/347,829, filed Apr. 11, 2024 Non-Final Office Action.
U.S. Appl. No. 17/347,829, filed Sep. 26, 2024 Final Office Action.
U.S. Appl. No. 17/347,845, filed Apr. 9, 2024 Final Office Action.
U.S. Appl. No. 17/347,845, filed Aug. 5, 2024 Non-Final Office Action.

* cited by examiner

ANALYTE SENSORS WITH REDUCED INTERFERENT SIGNAL AND METHODS

CROSS-REFERENCE TO RELATED APPLICATIONS

This application claims priority to and the benefit of U.S. Provisional Application No. 63/129,874, filed Dec. 23, 2020, which is incorporated by reference herein in its entirety.

FIELD

The subject matter described herein relates generally to systems, devices, and methods for in vivo monitoring of an analyte level.

BACKGROUND

The detection of various analytes within an individual can sometimes be vital for monitoring the condition of their health. Deviation from normal analyte levels can often be indicative of a number of physiological conditions. Glucose levels, for example, can be particularly important to detect and monitor in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Monitoring of other analytes may be desirable for other various physiological conditions. Monitoring of multiple analytes may also be desirable in some instances, particularly for comorbid conditions resulting in simultaneous dysregulation of two or more analytes in combination with one another.

Many analytes represent intriguing targets for physiological analyses, provided that a suitable detection chemistry can be identified. To this end, in vivo analyte sensors configured for assaying various physiological analytes have been developed and refined over recent years, many of which utilize enzyme-based detection strategies to facilitate detection specificity. Indeed, in vivo analyte sensors utilizing a glucose-responsive enzyme for monitoring blood glucose levels are now in common use among diabetic individuals. In vivo analyte sensors for other analytes are in various stages of development, including in vivo analyte sensors capable of monitoring multiple analytes. Poor sensitivity may be problematic for some analyte sensors, particularly due to background signal arising from interaction of an interferent with a working electrode or other analyte sensing chemistry components.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to an analyte sensor including an electrode layer having an elongate body comprising a proximal end and a distal end. The electrode layer includes a first active working electrode area, a second electrode portion, and at least one gap electrically separating the first active working electrode portion and the second electrode portion. The first active working electrode area comprises at least one sensing spot with at least one analyte responsive enzyme disposed thereupon.

In some embodiments, the first active working electrode area can include a plurality of sensing spots. The at least one analyte responsive enzyme disposed on the at least one sensing spot of the first active working electrode area can be a glucose responsive enzyme.

In some embodiments, the at least one gap in the electrode layer is U-shaped and extends from the proximal end of the elongate body on a first side of the first active working electrode area to proximate distal end of the elongate body of the electrode layer, and back to the proximal end of the elongate body on a second side of the first active working electrode area. Additionally or alternatively, the at least one gap can include two laterally spaced apart gaps extending from the proximal end of the elongate body of the electrode layer to the distal end of the elongate body of the electrode layer on opposing sides of the first active working electrode area. The at least one gap in the electrode layer can include a wavy pattern, a curly pattern, a curvy pattern, an undulating pattern, or a crimped pattern. The at least one gap in the electrode layer can have a width of about 1 µm to about 100 µm.

In some embodiments, the at least one gap can be formed in the electrode layer during fabrication of the electrode layer. For example, the at least one gap can be laser-cut in the electrode layer.

In some embodiments, the first active working electrode area can be connected to a first sensor current conductive trace and the second electrode portion of the electrode layer is not connected to a sensor current conductive trace. Alternatively, the first active working electrode area can be connected to a first sensor current conductive trace and the second electrode portion of the electrode layer can be connected to a second sensor current conductive trace. The second electrode portion can be a scrubbing electrode configured to oxidize one or more interferents.

In some embodiments, the interferent can selected from a group consisting of ascorbic acid, glutathione, uric acid, acetaminophen, isoniazid, salicylate, and combination thereof. For example, the interferent can be ascorbic acid.

The disclosed subject matter is also directed to an analyte sensor including an electrode layer having an elongate body comprising a proximal end and a distal end. The electrode layer includes a first active working electrode area having a plurality of sensing spots with at least one analyte-responsive enzyme disposed thereupon. First and second adjacent sensing spots in the first active working electrode area are in an overlapping configuration. The analyte sensor can include any of the features described for the analyte sensor above.

In some embodiments, third and fourth adjacent sensing spots in the first active working electrode area can be in an overlapping configuration. Additionally, all the plurality of sensing spots in the first active working electrode area can be in an overlapping configuration.

In some embodiments, the shape of each of the plurality of sensing spots can be substantially spherical, circular, square, rectangular, triangular, conical, or elliptical, or a combination thereof. The first, second, and third sensing spots in the first active working electrode area can be in an overlapping configuration.

In some embodiments, the plurality of sensing spots in the first active working electrode area can be in a linear configuration. Alternatively, the plurality of sensing spots in the first active working electrode area can be in a non-linear configuration. The plurality of sensing spots in the first active working electrode area can be in a grid configuration.

In some embodiments, the at least one analyte responsive enzyme disposed upon the plurality of sensing spots of the first active working electrode area can be a glucose responsive enzyme.

The disclosed subject matter is also directed to an analyte sensor including a substrate having an upper surface comprising a first portion and a second exposed portion, an electrode layer disposed upon the first portion of the upper surface of the substrate, and a membrane covering at least a portion of the electrode layer and the second exposed portion of the upper surface of the substrate. The electrode layer includes a first active working electrode area comprising at least one sensing spot with at least one analyte-responsive enzyme disposed thereupon. The analyte sensor can include any of the features described for the analyte sensors above.

In some embodiments, the substrate can include a polymeric material selected from polyester, and polyimide. For example, the polymeric material can be polyester.

In some embodiments, at least a portion of the second exposed portion of the upper surface of the substrate can be roughened. The second exposed portion of the upper surface of the substrate can have any suitable roughness value.

In some embodiments, the membrane can include a material selected from a polymeric material, a cross-linking agent, and combinations thereof. For example, the polymeric material can include polyvinylpyridine homopolymer or copolymer. The at least one analyte responsive enzyme disposed upon the sensing spot of the first active working electrode area can be a glucose responsive enzyme.

The disclosed subject matter is also directed to an analyte sensor including a substrate, an electrode layer disposed on the substrate and having an elongate body comprising a proximal end and a distal end, and an interferent-barrier membrane layer disposed upon at least a portion of the sensor and comprising sulfonated tetrafluoroethylene based fluoropolymer. The electrode layer includes a first active working electrode area comprises at least one sensing spot with at least one analyte responsive enzyme disposed thereupon. The first active working electrode area is connected to a sensor current conductive trace. The interferent barrier-membrane is configured to reduce an interferent signal of at least one interferent.

In some embodiments, the analyte sensor can also include a second membrane layer disposed upon the electrode layer and the interferent-barrier membrane layer is disposed upon the second membrane layer. The second membrane layer can include polyvinylpyridine homopolymer or copolymer. The interferent-barrier membrane layer can be coated on the second membrane layer. In some embodiments, the at least one interferent can be selected from a group consisting of ascorbic acid, glutathione, uric acid, acetaminophen, isoniazid, salicylate, and combination thereof. For example, the interferent can ascorbic acid. The interferent signal can be reduced to less than about 5% of a total signal when an electrode potential is in the range of about −100 mV to about +100 mV. For example, the interferent signal can be reduced to about 3% or less of a total signal when an electrode potential is in the range of about −80 mV to about +80 mV. The at least one analyte responsive enzyme disposed on the at least one sensing spot of the first active working electrode area can be glucose, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, troponin, alcohols, aspartate, asparagine and potassium, or creatinine responsive enzyme.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 16A and 16C are not laser planed. FIGS. 16B, 16D, and 16E are laser planed, in accordance with one or more aspects of the present disclosure.

DETAILED DESCRIPTION

Figure 1:
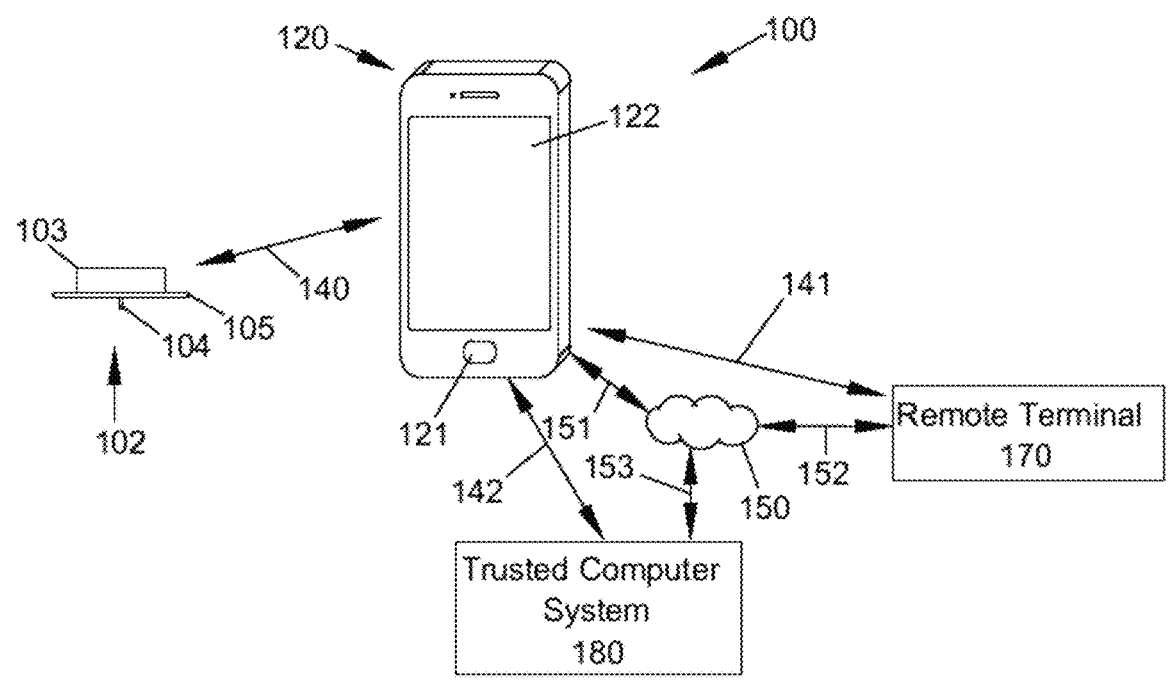
FIG. 1 shows a diagram of an illustrative sensing system that may incorporate an analyte sensor of the present disclosure.

The present disclosure generally describes analyte sensors suitable for in vivo use and, more specifically, analyte sensors featuring one or more enhancements for reducing or eliminating signals indicative of interferent species to promote improved detection sensitivity, and methods for production and use thereof.

Such enhancements may include decreasing the availability of a working electrode surface upon a sensor tail (the portion of a sensor for insertion into a tissue), particularly the availability of a carbon working electrode upon a sensor tail upon which interferents may react and contribute to signal not associated with the analyte. Other components of an analyte sensor may also react with an interferent and contribute to the signal at the carbon working electrode. Aspects of the present disclosure include, alone or in combination, planing asperities from a carbon working electrode, including compounds that react with interferents to prevent their interaction with a carbon working electrode, and/or addition of a scrubbing electrode to react with interferents to prevent their interaction with a carbon working electrode. In one or more aspects, the enhancements described herein may decrease the sensitivity of the sensor to interferents (e.g., by prohibiting or reducing interferents from generating signal at the working electrode, such as by eliminating excess carbon electrode surface using sensing chemistries and/or membranes) and/or decrease the local concentration of interferents at the working electrode (e.g., by "pre-reacting" the interferents such that they do not or substantially do not reach the working electrode). While not necessary, when the signal of the analyte of interest is not compromised, one or all of the enhancements described herein may be used in combination with a working electrode having a low working potential below the oxidation potential of the interferents of interest. In some instances, analyte sensors incorporating a low potential working electrode may further incorporate a low potential redox mediator to enhance detection of the analyte signal of interest of such low working potentials. Additionally, aspects of the present disclosure include, alone or in combination, treatment of a substrate layer below the working electrode to securely attach a membrane to the substrate.

The analyte sensors described herein comprise a sensor tail comprising at least one working electrode, particularly a carbon working electrode, and an active area disposed thereupon. A mass transport limiting membrane is then disposed upon the carbon working electrode (i.e., disposed upon both the active area and any extraneous carbon working electrode lacking the active area forming the sensor tail). Aspects of the present disclosure include the analyte sensors described herein, wherein the analyte sensors comprise a substrate having an upper surface and a second exposed surface. In particular, the substrate comprises at least one carbon electrode disposed upon the first portion of the upper surface of the substrate. Aspects of the present disclosure include, alone or in combination, a membrane disposed upon the carbon working electrode and at least a portion of the second exposed surface of the substrate.

Various carbon electrode asperities may exist along the edges of the carbon working electrode, where they may be insufficiently coated or are not coated at all with the mass transport limiting membrane, thereby providing a carbon surface for interferents to undergo a reaction and contribute to the measured signal at the working electrode. As used herein, the term "asperity," and grammatical variants thereof, refers to a rough edge along a surface (e.g., along a working electrode). Asperities may be in the form of a ridge along the edge of a working electrode, thereby leading to insufficient coating of a mass transport limiting membrane in this location. To reduce or eliminate such interferent signals, the present disclosure provides for planing of one or more edges of the carbon working electrode to remove carbon asperities therefrom, thereby affording a more uniform profile of the working electrode surface. Where the working electrode is formed from a material other than carbon, such asperities may be equally present in the composition of the particular working electrode ("electrode asperities").

Separate or in combination with planing one or more edges of the carbon working electrode to remove carbon asperities, the present disclosure further provides analyte sensors comprising one or more means to prevent or reduce an interferent's access to the working electrode. In particular, one or more enzymatic or chemical compounds may be incorporated into the analyte sensor which reacts with the interferent of interest to render it inactive such that it cannot contribute to the measured signal at the working electrode. Alternatively, or again in combination, a scrubbing electrode may be incorporated into the analyte sensor which reacts with the interferent of interest to render it inactive such that it cannot contribute to the measured signal at the working electrode.

Additionally, separate or in combination, one or more physical features, such as at least one gap in the electrode layer can be incorporated into the analyte sensor which allows a non-active portion of the electrode layer to pre-react with an interferent of interest to render it inactive such that it cannot contribute to the measure signal at the active working electrode area. Further, separate or in combination, the present disclosure provides, analyte sensors comprising decreased available area of active working electrode surface upon a sensor tail (the portion of a sensor for insertion into a tissue), particularly the availability of a carbon working electrode upon a sensor tail upon which interferents may react and contribute to signal not associated with the analyte by providing configurations of the working electrode described herein below.

Particular details and further advantages of each type of enhancement are described in further detail herein. Depending on particular needs, the analyte sensors of the present disclosure may be configured to detect one analyte or multiple analytes simultaneously or near simultaneously.

Analyte sensors employing enzyme-based detection are commonly used for assaying a single analyte, such as glucose, due to the frequent specificity of enzymes for a particular substrate or class of substrate. Analyte sensors employing both single enzymes and enzyme systems comprising multiple enzymes acting in concert may be used for this purpose. As used herein, the term "in concert," and grammatical variants thereof, refers to a coupled enzymatic reaction, in which the product of a first enzymatic reaction becomes the substrate for a second enzymatic reaction, and the second enzymatic reaction or a subsequent enzymatic reaction serves as the basis for measuring the concentration of an analyte. Moreover, a combination of enzymes and/or enzyme systems may be employed to detect more than one analyte type. Using an in vivo analyte sensor featuring an enzyme or enzyme system to promote detection may be particularly advantageous to avoid the frequent withdrawal of bodily fluid that otherwise may be required for analyte monitoring to take place.

In vivo analyte sensors monitor one or more analytes in a biological fluid of interest such as dermal fluid, interstitial fluid, plasma, blood, lymph, synovial fluid, cerebrospinal fluid, saliva, bronchoalveolar lavage, amniotic fluid, or the like. Such fluids may comprise one or more interferents that can react with the working electrode of the analyte sensor, either directly on the working electrode itself (e.g., carbon working electrode) or with one or more sensing chemistry components disposed thereupon (e.g., the redox polymer described hereinbelow). As used herein, the term "interferent," and grammatical variants thereof, refers to any electroactive species present that are not an analyte(s) of interest (e.g., in vivo electroactive species that are not an analyte(s) of interest) within a bodily fluid (e.g., interstitial fluid, and the like). Examples include, but are not limited to, ascorbic acid (vitamin C), glutathione, uric acid, paracetamol (acetaminophen), isoniazid, salicylate, and the like, and any combination thereof. The reaction of these interferents with the working electrode can create an electrochemical signal that is inseparable or not easily separable from signal originating from the analyte of interest, which may complicate the accurate detection of such analytes, particularly those in low-abundance (e.g., low- to sub-millimolar concentrations). The electrochemical signal generated by an interferent may be particularly problematic as the signal from the interferent becomes closer in magnitude to that of the signal from the target analyte. This may occur, for example, when the concentration of the interferent approaches or exceeds the concentration of the analyte of interest. Some interferents are ubiquitous in vivo and are not easily avoided. Therefore, techniques to minimize their influence during in vivo analyses may be highly desirable.

The present disclosure provides analyte sensor enhancements that, either alone or in combination with other enhancements, may improve detection sensitivity for both single analytes and multiple analytes in combination with one another, as explained in further detail hereinbelow. Namely, the present disclosure provides analyte sensors having reduced carbon working electrode edge asperities and/or incorporated compounds or scrubbing electrodes that may afford decreased background signal resulting from in vivo interferents. Although certain aspects of the present disclosure are directed to enhancement of carbon working electrodes, it is to be appreciated that other types of electrodes may be similarly enhanced according to the disclosure herein. Electrode types that may be enhanced through use of the disclosure herein also include gold, platinum, PEDOT, and the like.

Before describing the analyte sensors of the present disclosure and their enhancements in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure. As shown, sensing system 100 includes sensor control device 102 and reader device 120 that are configured to communicate with one another over local communication path or link 140, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances.

Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety.

Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Alternately, sensor 104 may be adapted to penetrate the epidermis. Still further alternately, sensor 104 may be disposed superficially and not penetrate a tissue, such as when assaying one or more analytes in perspiration upon the skin. Sensor 104 may comprise a sensor tail of sufficient length for insertion to a desired depth in a given tissue. The sensor tail may comprise at least one working electrode and an active area comprising an enzyme or enzyme system configured for assaying one or more analytes of interest.

A counter electrode may be present in combination with the at least one working electrode, optionally in further combination with a reference electrode. Particular electrode configurations upon the sensor tail are described in more detail below in reference to FIG. 2A-4. One or more enzymes in the active area may be covalently bonded to a polymer comprising the active area, according to various embodiments. Alternately, enzymes may be non-covalently associated within the active area, such as through encapsulation or physical entrainment. The one or more analytes may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine analyte concentrations in vivo. It is to be appreciated, however, that the entirety of sensor control device 102 may have one or more various configurations permitting full transplantation beneath tissue and into one or more body fluids for assaying one or more analytes of interest, without departing from the scope of the present disclosure.

Referring again to FIG. 1, sensor 104 may automatically forward data to reader device 120. For example, analyte concentration data may be communicated automatically and periodically, such as at a certain frequency as data is obtained or after a certain time period has passed, with the data being stored in a memory until transmittal (e.g., every minute, five minutes, or other predetermined time period), such as by BLUETOOTH® or BLUETOOTH® Low Energy protocols. Data associated with different analytes may be forwarded at the same frequency or different frequencies and/or using the same or different communication protocols. In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time, automatically or non-automatically. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp, or a combination thereof. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications. For example, needles having a cross-sectional diameter ranging from about 300 microns to about 400 microns may be used.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle may be subsequently withdrawn after facilitating sensor insertion.

Figure 2A:
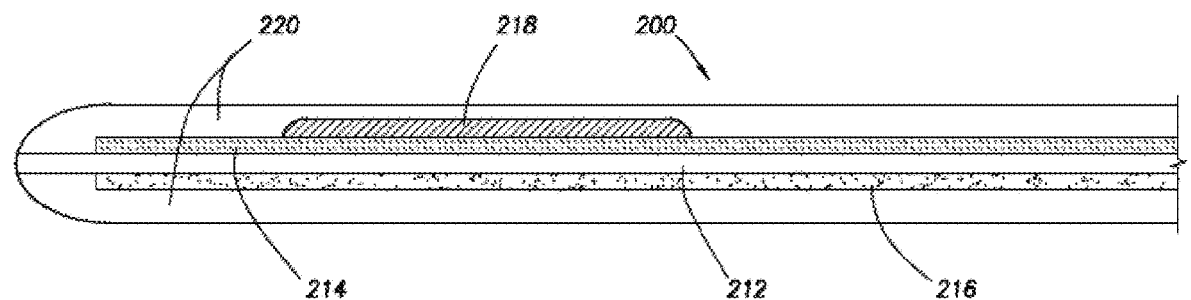
FIGS. 2A-2C show cross-sectional diagrams of analyte sensors comprising a single active area.
Figure 2B:
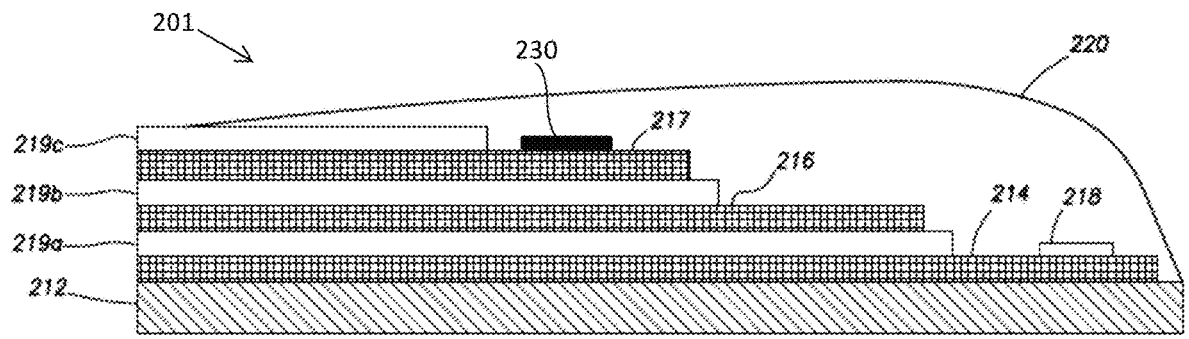
Figure 2C:
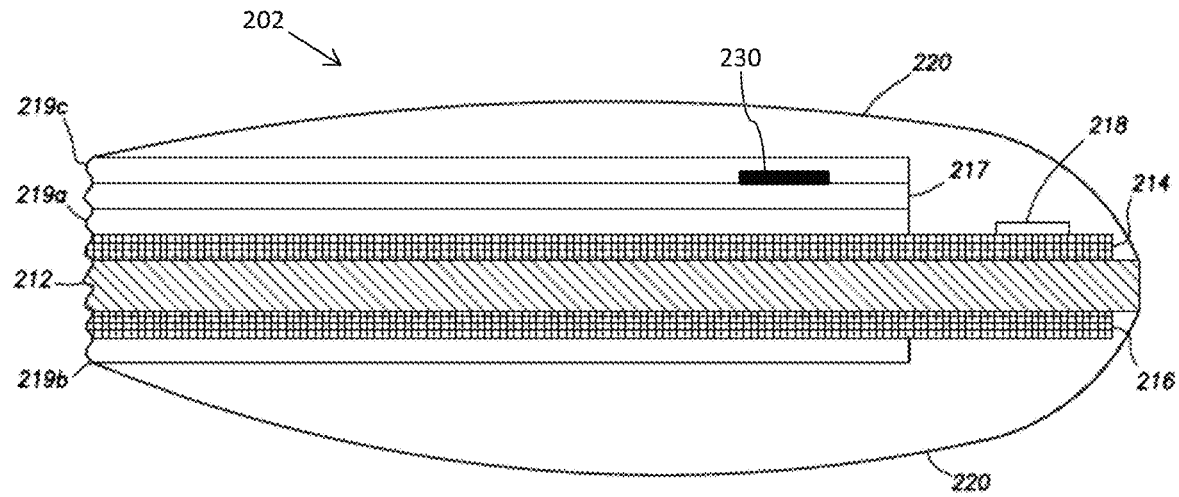

Sensor configurations featuring a single active area that is configured for detection of a corresponding single analyte may employ two-electrode or three-electrode detection motifs, as described further herein in reference to FIGS. 2A-2C. Sensor configurations featuring two different active areas for detection of separate analytes, either upon separate working electrodes or upon the same working electrode, are described separately thereafter in reference to FIGS. 3A-4. Sensor configurations having multiple working electrodes may be particularly advantageous for incorporating two different active areas within the same sensor tail, since the signal contribution from each active area may be determined more readily through separate interrogation of each working electrode. Each active area may be overcoated with a mass transport limiting membrane of the same or different composition.

When a single working electrode is present in an analyte sensor, three-electrode sensor configurations may comprise a working electrode, a counter electrode, and a reference electrode. Related two-electrode sensor configurations may comprise a working electrode and a second electrode, in which the second electrode may function as both a counter electrode and a reference electrode (i.e., a counter/reference electrode). The various electrodes may be at least partially stacked (layered) upon one another and/or laterally spaced apart from one another upon the sensor tail. In any of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

Any of the working electrode configurations described hereinafter may benefit from the further disclosure below directed to decreasing the availability of edge asperities of the working electrode upon the sensor tail.

FIG. 2A shows a diagram of an illustrative two-electrode analyte sensor configuration, which is compatible for use in the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. Active area 218 may comprise multiple spots or a single spot configured for detection of an analyte, as discussed further herein.

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 (i.e., membrane 220 is a mass transport limiting membrane having some permeability for the analyte of interest). The composition and thickness of membrane 220 may vary to promote a desired analyte flux to active area 218, thereby providing a desired signal intensity and stability. Analyte sensor 200 may be operable for assaying an analyte by any of coulometric, amperometric, voltammetric, or potentiometric electrochemical detection techniques.

FIGS. 2B and 2C show diagrams of illustrative three-electrode analyte sensor configurations, which are also compatible for use in the disclosure herein. Three-electrode analyte sensor configurations may be similar to that shown for analyte sensor 200 in FIG. 2A, except for the inclusion of additional electrode 217 in analyte sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219a, 219b, and 219c separate electrodes 214, 216, and 217 from one another and provide electrical isolation. Alternately, at least one of electrodes 214, 216, and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 2A, active area 218 in analyte sensors 201 and 202 may comprise multiple spots or a single spot. Additionally, analyte sensors 201 and 202 may likewise be operable for assaying an analyte by any of coulometric, amperometric, voltammetric, or potentiometric electrochemical detection techniques.

Like analyte sensor 200, membrane 220 may also overcoat active area 218, as well as other sensor components, in analyte sensors 201 and 202, thereby serving as a mass transport limiting membrane. Additional electrode 217 may be overcoated with membrane 220 in some embodiments. Membrane 220 may again be produced through dip coating or in situ photopolymerization and vary compositionally or be the same compositionally at different locations. Although FIGS. 2B and 2C have depicted all of electrodes 214, 216, and 217 as being overcoated with membrane 220, it is to be recognized that only working electrode 214 or active area 218 may be overcoated in some embodiments. Moreover, the thickness of membrane 220 at each of electrodes 214, 216, and 217 may be the same or different. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

Figure 3A:
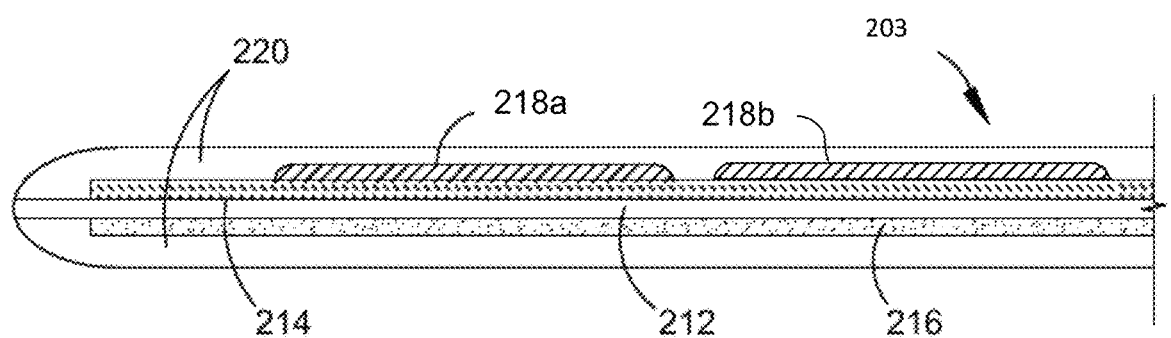
FIGS. 3A-3C show cross-sectional diagrams of analyte sensors comprising two active areas.

FIG. 3A shows an illustrative configuration for sensor 203 having a single working electrode with two different active areas disposed thereon. FIG. 3A is similar to FIG. 2A, except for the presence of two active areas upon working electrode 214: first active area 218a and second active area 218b, which are responsive to different analytes and are laterally spaced apart from one another upon the surface of working electrode 214. Active areas 218a and 218b may comprise multiple spots or a single spot configured for detection of each analyte. The composition of membrane 220 may vary or be compositionally the same at active areas 218a and 218b. First active area 218a and second active area 218b may be configured to detect their corresponding analytes at working electrode potentials that differ from one another, as discussed further below.

Figure 3B:
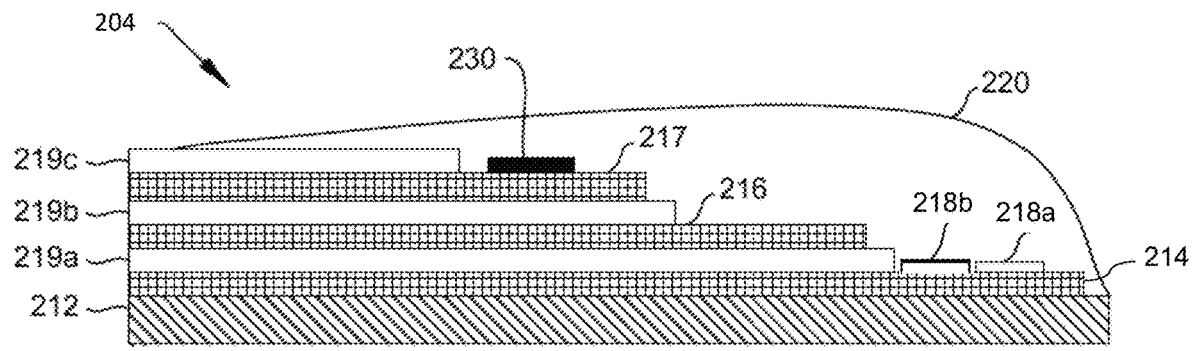
Figure 3C:
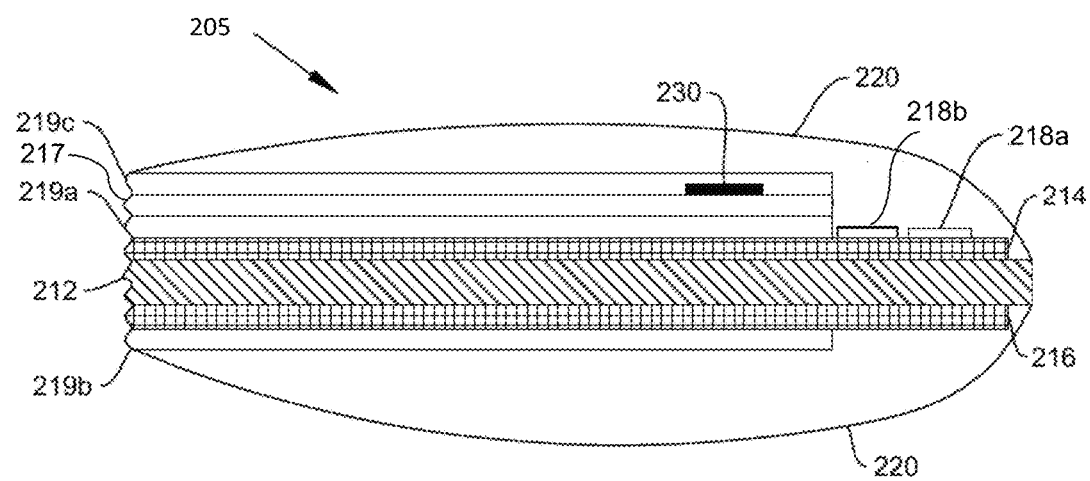

FIGS. 3B and 3C show cross-sectional diagrams of illustrative three-electrode sensor configurations for sensors 204 and 205, respectively, each featuring a single working electrode having first active area 218a and second active area 218b disposed thereon. FIGS. 3B and 3C are otherwise similar to FIGS. 2B and 2C and may be better understood by reference thereto. As with FIG. 3A, the composition of membrane 220 may vary or be compositionally the same at active areas 218a and 218b.

Figure 4:
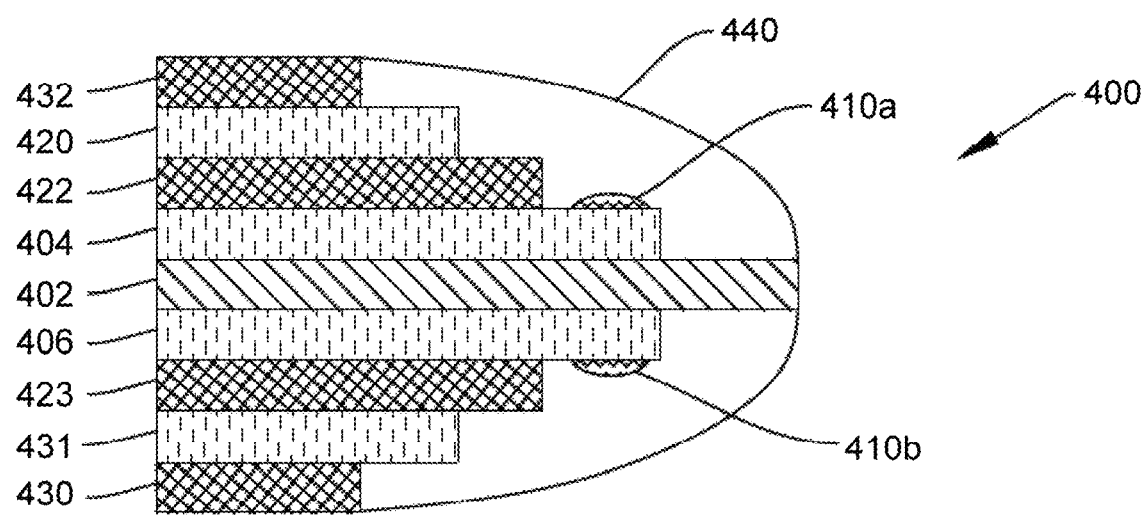
FIG. 4 shows a cross-sectional diagram of an analyte sensor comprising two working electrodes, each having an active area present thereon.

FIG. 4 shows a cross-sectional diagram of an illustrative analyte sensor configuration having two working electrodes, a reference electrode, and a counter electrode, which is compatible for use in the disclosure herein. As shown, analyte sensor 400 includes working electrodes 404 and 406 disposed upon opposite faces of substrate 402. First active area 410a is disposed upon the surface of working electrode 404, and second active area 410b is disposed upon the surface of working electrode 406. Counter electrode 420 is electrically isolated from working electrode 404 by dielectric layer 422, and reference electrode 421 is electrically isolated from working electrode 406 by dielectric layer 423. Outer dielectric layers 430 and 432 are positioned upon reference electrode 421 and counter electrode 420, respectively. Membrane 440 may overcoat at least active areas 410a and 410b, according to various embodiments, with other components of analyte sensor 400 or the entirety of analyte sensor 400 optionally being overcoated with membrane 440 as well. Again, membrane 440 may vary compositionally at active areas 410a and 410b, if needed, in order to afford suitable permeability values for differentially regulating the analyte flux at each location.

Alternative sensor configurations having multiple working electrodes and differing from the configuration shown in FIG. 4 may feature a counter/reference electrode instead of separate counter and reference electrodes 420, 421, and/or feature layer and/or membrane arrangements varying from those expressly depicted. For example, the positioning of counter electrode 420 and reference electrode 421 may be reversed from that depicted in FIG. 4. In addition, working electrodes 404 and 406 need not necessarily reside upon opposing faces of substrate 302 in the manner shown in FIG. 4.

A carbon working electrode may suitably comprise the working electrode(s) in any of the analyte sensors disclosed herein. While carbon working electrodes are very commonly employed in electrochemical detection, use thereof in electrochemical sensing is not without difficulties. In particular, current related to an analyte of interest only results when an active area interacts with an analyte and transfers electrons to the portion of the carbon working electrode adjacent to the active area. Bodily fluid containing an analyte of interest also interacts with a carbon surface of the carbon working electrode not overcoated with an active area and does not contribute to the analyte signal, since there is no enzyme or enzyme system present at these locations to facilitate electron transfer from the analyte to the working electrode. Interferents may, however, undergo oxidation at portions of the working electrode lacking an active area and contribute background to the overall signal. Thus, carbon working electrodes with an extraneous (or "exposed") carbon area upon the electrode surface do not meaningfully contribute to the analyte signal and may lead to contributory background signals in some cases. Other electrodes having an excessive surface area not directly detecting an analyte of interest may experience similar background signals and may be enhanced through modification of the disclosure herein.

Although various interferents may interact with the working electrode of the analyte sensors described herein, ascorbic acid is one example of an interferent commonly present in biological fluids that may generate a background signal at a carbon working electrode. For example, ascorbic acid oxidizes at the working electrode to produce dehydroascorbic acid. Various embodiments of the present disclosure will be described herein with reference to the interferent being ascorbic acid; however, it is to be understood that that the embodiments and analyte sensor configurations described herein are equally applicable to other interferents (electroactive species within a bodily fluid having an analyte of interest).

Figure 5:
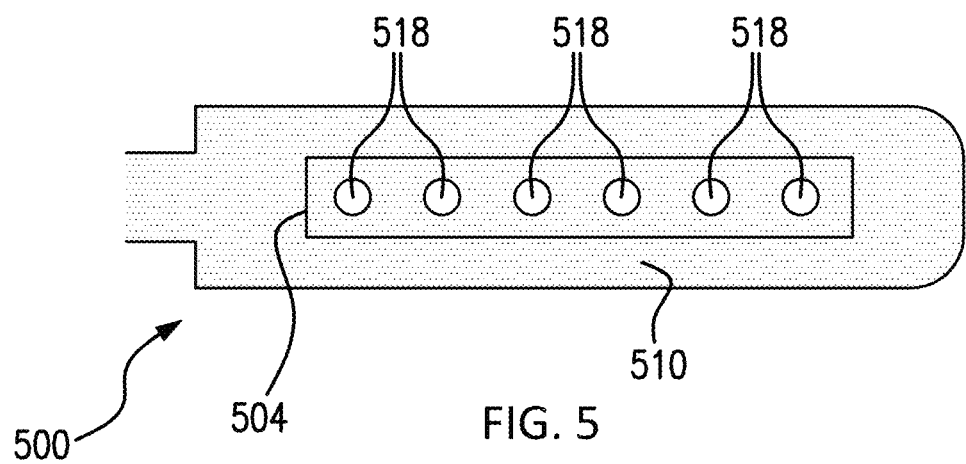
FIG. 5 is a diagram showing a top view of a conventional carbon working electrode having an active area thereon.

As provided above, the active area described herein may be a single sensing layer or a sensing layer having multiple sensing spots. Referring now to FIG. 5, illustrated is a top view of conventional carbon working electrode 500 having an active area 504 disposed thereon comprising multiple sensing spots 518. Only portions of carbon working electrode 500 comprising the sensing spots 518 contribute signal associated with an analyte of interest when the analyte interacts with the active area 504. Although carbon working electrode 500 shows six sensing spots 518 within the active area 504, it is to be appreciated that fewer or greater than six sensing spots 518 may be included upon carbon working electrode 500, without departing from the scope of the present disclosure. Extraneous carbon area 510 is not directly overlaid with sensing spots 518 and does not contribute signal associated with the analyte but may generate a background signal associated with one or more interferents. Accordingly, the oxidation of interferents at carbon working electrode 500 is proportional to the area of extraneous carbon area 510 available for interaction with the interferents. Indeed, the oxidation of ascorbic acid at carbon working electrode 500 scales roughly linearly with the area of available extraneous carbon area 510.

As shown, the active area 504 is discontiguous and in the form of multiple sensing spots 518. As defined herein, the term "discontiguous," and grammatical variants thereof, means that any single spot (sensing element) does not share an edge or boundary (e.g., is not touching) an adjacent spot.

The sensor tails described in the present disclosure comprising the carbon working electrode 500 may be prepared upon a template substrate material (see FIGS. 2A-2B, 3A-3C, 4) along with additional layered elements of the sensor tail (e.g., dielectric materials, other electrodes, and the like). During sensor fabrication, the sensor tail comprising the carbon working electrode 500 is thereafter singulated by one or more means. Singulation may be achieved by one or more cutting or separation protocols including, but not limited to, laser singulation, slitting, shearing, punching, and the like. Singulation of the sensor tails may be performed before or after application of the active area upon the carbon working electrode 500 toward the distal tip of the sensor tail (i.e., the portion of the sensor tail that will be inserted deepest into a tissue). As used herein, the distal "tip" of the sensor tail is referred to as the most distal edge of a sensor tail, or that portion that is most deeply inserted into a tissue.

One or more portions of the sensor tail are laser singulated, typically requiring multiple laser passes, to cut the sensor tail into the desired shape. At the tip of the sensor tail comprises at least a portion of the working electrode and the active area. Typically, the laser singulated sensor tails have a width in the range of about 100 µm to about 500 µm and a length of about 3 mm to about 10 mm, encompassing any value and subset therebetween. Generally, the distal portion of the sensor tail accounts for a distal length of about 0.5 mm to about 5 mm, encompassing any value and subset therebetween. After laser singulation, a mass transport limiting membrane is deposited upon at least the sensor tip comprising the active area.

In one or more aspects of the present disclosure, prior to disposing the mass transport limiting membrane, carbon asperities may be present along the edges of the carbon electrode due to the laser singulation process. These carbon asperities may provide a surface upon which interferents may react and contribute background signal to an analyte sensor.

Laser singulation of a carbon working electrode may result in the formation of carbon asperities having widths of about 50 µm or less, such as in the range of about 5 µm to about 50 or about 10 µm to about 30 encompassing any value and subset therebetween. Further, these carbon asperities may have a height of about 20 µm or less, such as in the range of about 1 µm to about 20 or about 2 µm to about 10 as described hereinbelow in greater detail, encompassing any value and subset therebetween. Accordingly, these carbon asperities may provide substantial area with which interferents may interact. In addition, the asperities can contribute to inconsistent coverage (thickness) of a mass transport limiting membrane. These carbon asperities may be reduced or removed by one or more laser planing methods, as described hereinbelow.

Figure 6A:
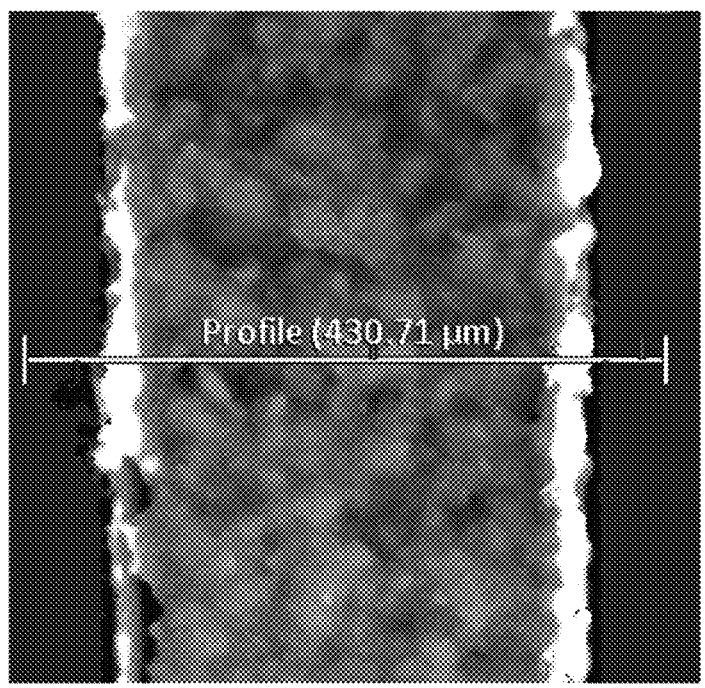
FIG. 6A shows a photograph of a top view of a working electrode having no membrane disposed thereon.
Figure 6B:
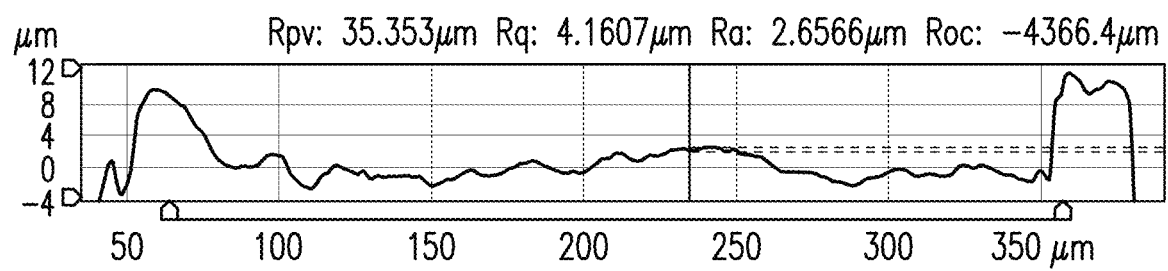
FIG. 6B is a depth profile along the line indicated in FIG. 6A.

Referring first to FIG. 6A, and prior to any laser planing to reduce or remove carbon asperities in accordance with the present disclosure, illustrated is a close up of an example of a laser singulated carbon working electrode for use as at least a portion of a sensor tail, in which the carbon working electrode has no mass transport limited membrane deposited thereon. Electrodes cut into their desired shape by other means may have asperities of a similar appearance and size. Carbon asperities are apparent along the edges of the working electrode with which interferents may react. FIG. 6B shows a depth profile along the line indicated in FIG. 6A, evaluated along the identified 430.71 µm profile width. The 3D optical profile was obtained using a ZEGAGE™ 3D Optical Profiler, ZYGOO® Corporation (Middlefield, CT). As shown in FIG. 6B, carbon asperities along the singulation (ablation) edges of the example singulated sensor tail are up to about 30 µm wide and up to about 10 µm in height.

A mass transport limiting membrane may reduce or prevent interferent access to extraneous carbon areas (e.g., extraneous carbon area 510 of FIG. 5). When disposed upon a laser singulated carbon working electrode (and an active area thereupon), the thickness of the membrane varies across the width of the working electrode, particularly where significant asperities are present. Typically, the membrane is thinnest along the edges of the electrode, which is also where the carbon asperities are located. Accordingly, even when a membrane is present, the carbon asperities may not be sufficiently coated with the membrane to adequately reduce or prevent interferent interaction therewith.

Figure 7A:
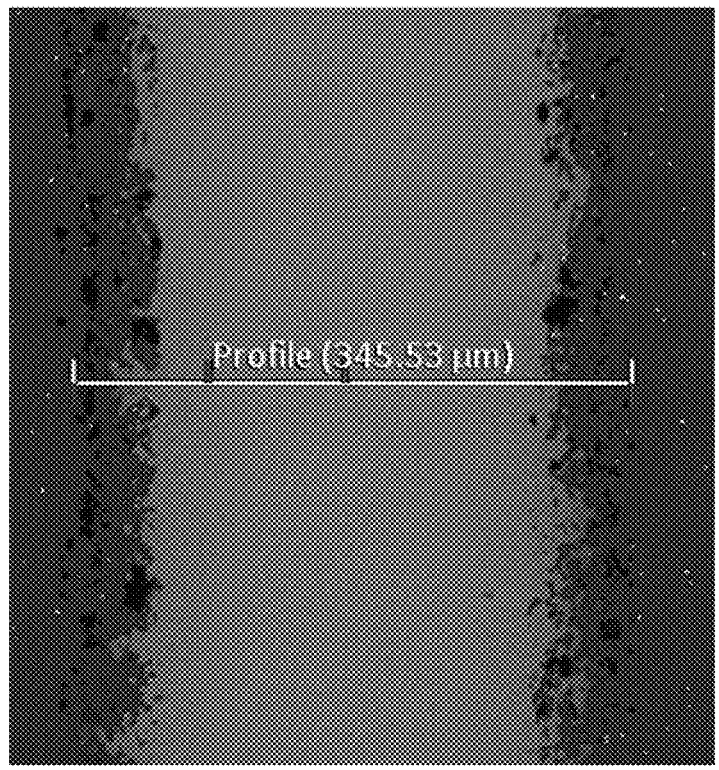
FIG. 7A shows a photograph of a top view of a working electrode having a membrane disposed thereon.
Figure 7B:
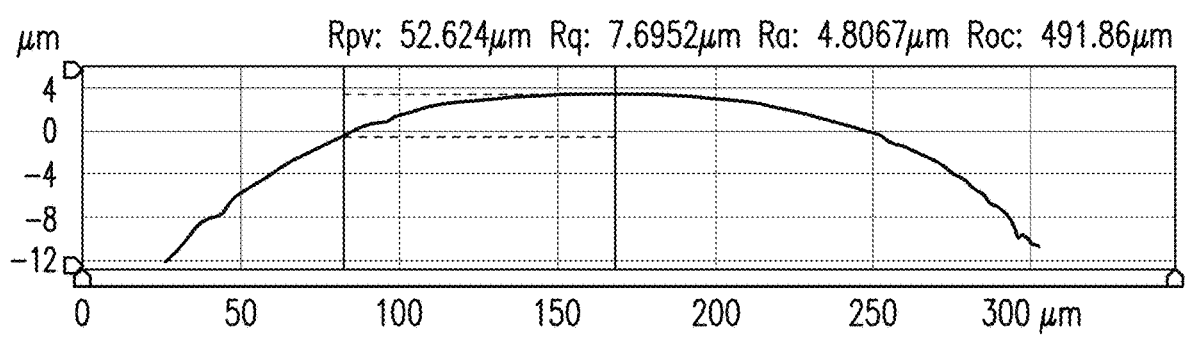
FIG. 7B is a depth profile along the line indicated in FIG. 7A.

Referring to FIG. 7A, and prior to any laser planing to reduce or remove carbon asperities in accordance with one or more aspects of the present disclosure, illustrated is a close up of an example laser singulated carbon working electrode having a mass transport limited membrane deposited thereon. FIG. 7B shows a depth profile along the line indicated in FIG. 7A, evaluated along the identified 345.53 µm profile width. The 3D optical profile was obtained using a ZEGAGE™ 3D Optical Profiler, ZYGOO® Corporation (Middlefield, CT). As shown in FIG. 7B, the membrane is considerably thinner along the singulation ridges of the carbon working electrode.

In various aspects, the present disclosure provides methods and analyte sensors in which carbon working electrodes for use in forming a sensor tail are planed by one or more single- or multi-pass laser planing cuts, alone or in combination with the additional enhancements described herein. In some embodiments, a single-pass laser planing method is used in which the laser depth is set to less than the thickness of the working electrode. For example, the laser planing may remove the top portions of the carbon layer, such as the top 50% of the carbon layer. The carbon layer is typically in the range of 10 µm (without asperities); in some embodiments, about 5 µm (or about 50%) may be removed therefrom (e.g., see FIG. 9C). Laser planing according to the disclosure herein may remove or decrease the prominence of asperities.

In some embodiments, greater than 1, such as less than about 10, single-pass laser planing cuts may be made, each progressively closer to the midline length of the working electrode to reduce or eliminate the carbon asperities. In such a way, initial laser planing cuts may be made at the outermost location of any single carbon asperity and subsequent laser planing cuts may be made toward the midline length of the working electrode to create a milled edge, which may be a stepped edge of approximately 90° or beveled edge (i.e., an edge that is not perpendicular to the faces of the electrode) if, for example, the most proximal laser planing cut toward the midline of the electrode does not result in a true 90° angle (see FIG. 8, laser planing cut (edge) 810 shown as a sloped edge rather than a shear 90° angle edge). For example, in one embodiment, about 2 to about 10 single-pass laser planing cuts may be made, each having a distance apart between about 1 µm to about 100 µm, encompassing any value and subset therebetween. Selection of the particular number of laser planing passes and their distance apart may be based on a number of factors including, but not limited to, the shape and size of the carbon asperities, the length and width of the working electrode, the coverage profile of any membrane disposed thereupon, and the like, and any combination thereof.

Laser planing may be preferentially used to remove at least about 5% up to about 95% of the total carbon asperity area from a singulated sensor tail comprising a carbon working electrode, encompassing any value and subset therebetween. In some embodiments, up to 100% of the carbon asperities are removed, or about 5% to about 50%, encompassing any value and subset therebetween. In preferred embodiments, at least about 50% of the carbon asperities are removed. The particular amount of carbon asperity removal may be based on a number of factors including, but not limited to, the density, shape, and size of the carbon asperities, the concentration of analyte of interest compared to the concentration of interferent available within the bodily fluid being assayed and the like, and any combination thereof.

Figure 8:
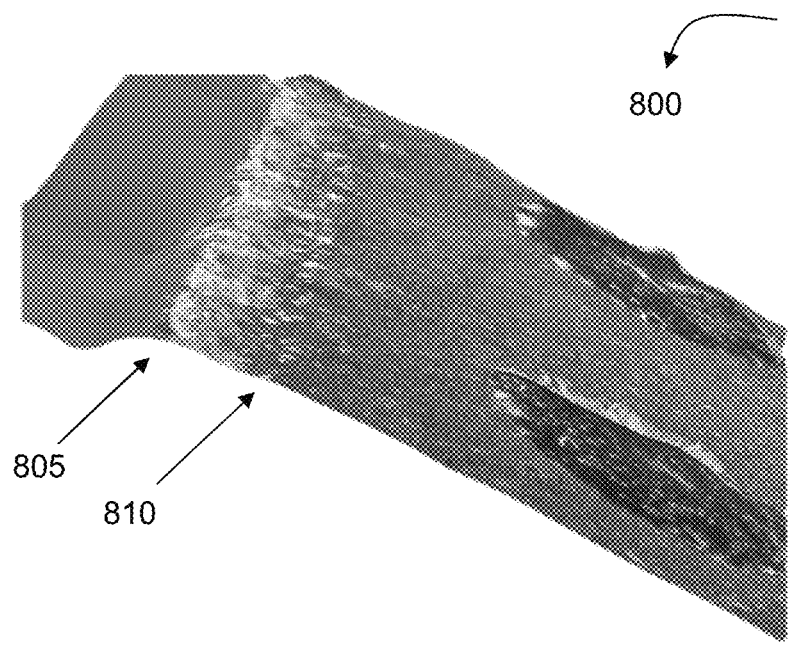
FIG. 8 is a photograph showing a 3D view of a laser planed working electrode, in accordance with one or more aspects of the present disclosure.

FIG. 8 shows a photograph of an edge of a sensor tail 800 showing laser singulation cut (ridge) 805 and laser planing cut (edge) 810 recessed from the edge of the sensor tail to remove a portion of the edge of a carbon working electrode (the carbon or electrode layer), in accordance with one or more embodiments of the present disclosure. That is, the laser planing cut 810 is directed to reducing the carbon asperities along the upper or top portion of the carbon electrode (where the active area resides, for example), while a thinner portion of the working electrode remains along an outer perimeter (and at the opposite portion of the electrode, which does not comprise the active area).

In one or more aspects of the present disclosure, alone or in combination with any other enhancements to reduce or eliminate analyte sensor signals associated with interferents, provided is an analyte sensor comprising an interferent-reactant species. As used herein, the term "interferent-reactant species," and grammatical variants thereof, refers to any compound, whether biological or non-biological, that are capable of reacting with an interferent and rendering it inactive such that it cannot contribute to the measured signal at the working electrode. That is, the interferent-reactant species may be included as part of an analyte sensor in order to "pre-react" an interferent before it is able to react on the working electrode of the analyte sensor. Accordingly, the interferent-reactant species can eliminate or reduce the local concentration of an interferent present at or accessible to the working electrode, thereby eliminating or reducing signal attributed to such interferents because the interferents never reach excess area of a working electrode.

Various aspects of the methods and analyte sensors integrating an interferent-reactant species are described with reference to interferent-reactant species for ascorbic acid elimination or removal, it is to be continually appreciated that the enhancements described herein pertain to other potential interferents, without limitation. Such interferents may include, for example, ascorbic acid (vitamin C), glutathione, uric acid, paracetamol (acetaminophen), isoniazid, salicylate, and the like, and any combination thereof. In non-limiting examples, the interferent-reactant species of the present disclosure may be an enzyme of ascorbate oxidase (to react with ascorbic acid), glutathione peroxidase (to react with glutathione), xanthine oxidase (to react with uric acid), urate oxidase (to react with uric acid), cytochrome P450 (to react with paracetamol), eosinophil peroxidase (to react with isoniazid), salicylate-oxidizing enzyme (to react with salicylate), other enzymes that can oxidize, reduce, or otherwise react and decompose the interferent of interest, and the like, and any combination thereof. In alternative or combination embodiments, the interferent-reactant species may be one of a non-enzyme. For example, various metal oxides, such as manganese oxide ($MnO_2$) or iron oxide ($Fe_2CO_3$) may oxidize or otherwise react and decompose ascorbic acid and be used as the one or more interferent-reactant species of the present disclosure.

Figure 9A:
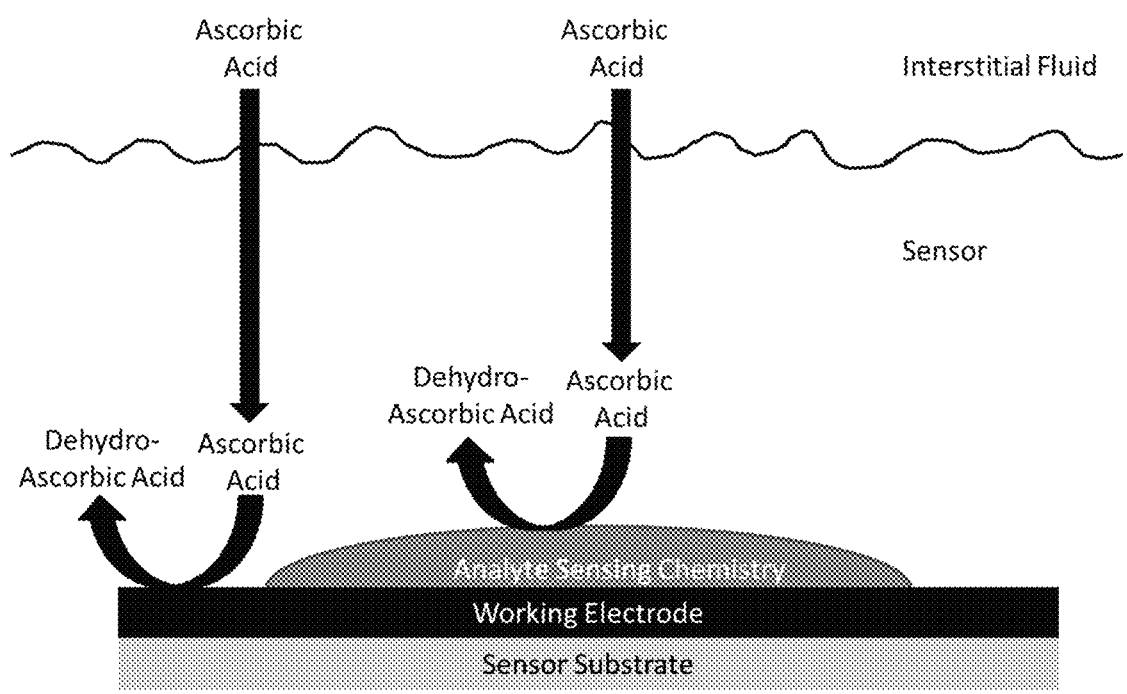
FIG. 9A is a depiction of a convention sensor having no incorporated interferent-reactive species.

Referring to FIG. 9A, illustrated is a depiction of a convention sensor demonstrating potential interferent reaction of ascorbic acid with excess working electrode and, potentially, also the sensing chemistry, thereby producing signal attributable to the ascorbic acid. The sensor of FIG. 9A has no interferent-reactant species incorporated therewith. As shown, the ascorbic acid interferent diffuses from the interstitial fluid toward the sensor working electrode, where it may be oxidized at least on the excess working electrode and/or additionally on the sensing chemistry.

Figure 9B:
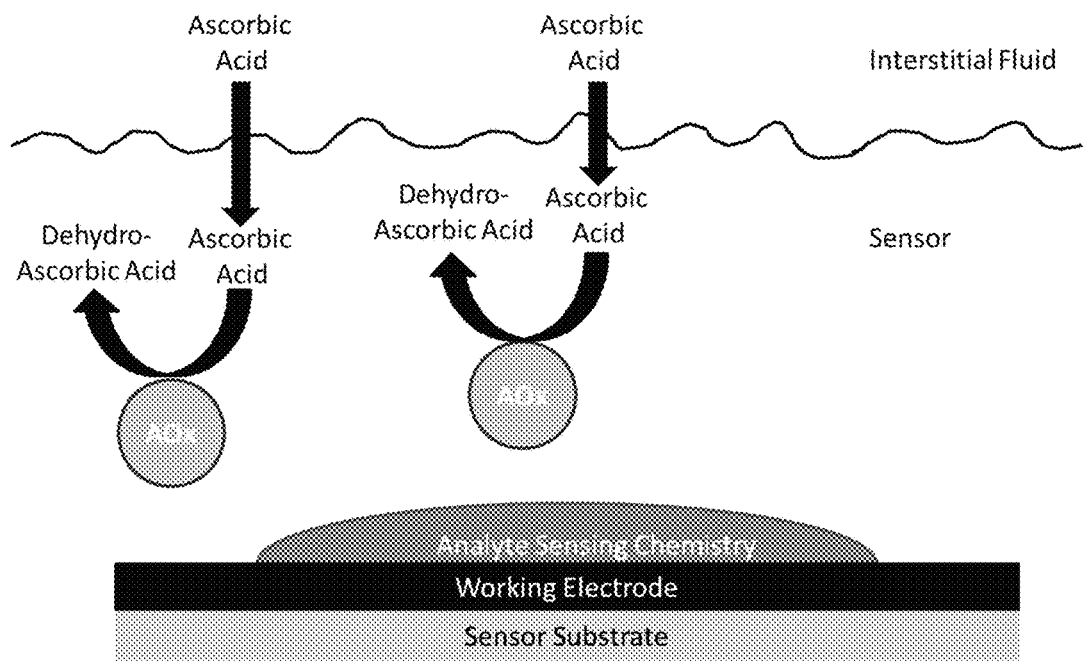
FIG. 9B is a depiction of the sensor of FIG. 9B incorporating interferent-reactive species, in accordance with one or more aspects of the present disclosure.

According to various aspects of the present disclosure, FIG. 9B illustrates a depiction of the sensor of FIG. 9A incorporating an interferent-reactant species, and in particular the interferent-reactant species of ascorbate oxidase (AOx). As shown, the ascorbate oxidase reacts with the ascorbic acid prior to it contacting the working electrode or sensing chemistry, thereby preventing said reacted ascorbic acid from contributing to analyte signal. It is to be noted that the sensor depicted in FIG. 9B may have any configuration and/or component of the sensors described herein, without limitation.

The particular location of one or more interferent-reactant species for incorporation into the analyte sensors of the present disclosure is not considered to be particularly limiting. For example, the interferent-reactant species provided as part of an analyte sensing active area; a membrane coating an analyte sensing active area; provided as its own layer atop any of a working electrode, analyte sensing active area, and/or membrane coating; and the like; and any combination thereof. When provided as part of an active layer, membrane, or its own layer, it may be free-floating or otherwise immobilized (e.g., covalently or non-covalently bound) within a polymer matrix. The particular concentration of the interferent-reactant species incorporated into an analyte sensor (in any one or more locations) may depend on a number of factors including, but not limited to, the particular analyte (s) of interest, the particular interferent(s) of interest, the in vivo location of the analyte sensor, and the like, and any combination thereof. In some instances, when the interferent-reactant species is an enzyme, the total amount of interferent-reactant species may be in the range of about 0.01 Units to about 100 Units of activity per sensor, encompassing any value and subset therebetween. For example, a sensor having an interferent-reactant species of ascorbate oxidase may have about 0.5 Units of activity per sensor. In other instances, when the interferent-reactant species is a non-enzyme compound, such as a metal oxide, the total amount of interferent-reactant species may be in the range of about 0.1 μg to about 100 μg per sensor, encompassing any value and subset therebetween. For example, a sensor having an interferent-reactant species of $MnO_2$ may be present in an amount of about 1 μg per sensor.

As stated above, generally, the interferent-reactant species described herein, whether present as a layer itself, present within the membrane, or present within an active area will be present within a polymer matrix, either mobilized or immobilized. This polymer matrix may be composed of any polymers, crosslinkers, and/or additives compatible with the interferent-reactant species selected for use in the analyte sensor that does not interfere with the sensing chemistry. Each of the polymers, crosslinkers, and/or additives may be selected from any of those described herein, without limitation. For example, non-limiting examples of such polymers include poly(4-vinylpyridine) and poly(N-vinylimidazole) (PVI) or a copolymer thereof, a sulfonated tetrafluoroethylene based fluoropolymer-copolymer (e.g., NAFION™, The Chemours Company, Wilmington, DE), polyvinyl alcohol, and any combination thereof; non-limiting examples of crosslinkers include triglycidyl glycerol ether (gly3) and/or PEDGE and/or polydimethylsiloxane diglycidylether (PDMS-DGE); non-limiting examples of additives include stabilizers, such as albumin, and/or any other stabilizers described herein.

In one or more aspects of the present disclosure, alone or in combination with any other enhancements to reduce or eliminate analyte sensor signals associated with interferents, provided is an analyte sensor comprising a scrubbing electrode (with or without integration of an interferent-reactant species and/or asperity planing, for example). As described herein, the term "scrubbing electrode," and grammatical variants thereof, refers to an electrode capable of reacting with an interferent to render it inactive such that it cannot contribute to the measured signal at the working electrode. That is, the scrubbing electrode may be included as part of an analyte sensor in order to "pre-react" an interferent before it is able to react on the working electrode of the analyte sensor. Accordingly, similar to the presence of an interferent-reactant species, the scrubbing electrode can eliminate or reduce the local concentration of an interferent present at or accessible to the working electrode, thereby eliminating or reducing signal attributed to such interferents because the interferents never reach excess area of a working electrode.

In one or more aspects, the scrubbing electrode may be positioned in a facing relationship, and spatially offset from the working electrode. That is, the active area of the working electrode and the active area of the scrubbing electrode, which may or may not be disposed on a substrate, face one another and are separated by a gap. Preferably, the gap is a thin layer between the two electrodes that permits bodily fluids to pass therebetween, including the analyte of interest and any interferent(s) therein. The configuration of the scrubbing electrode relative to the working electrode is desirably such that the bodily fluid comes into contact with the scrubbing electrode for a sufficient time to react to any interferent prior to the bodily fluid reaching the working electrode. The scrubbing electrode does not comprise any sensing chemistry and, accordingly, analytes of interest do not react therewith. In such a manner, the bodily fluid has been rid or substantially rid of the interferent, and the signal obtained at the working electrode is attributable entirely or primarily to the analyte of interest.

Figure 10:
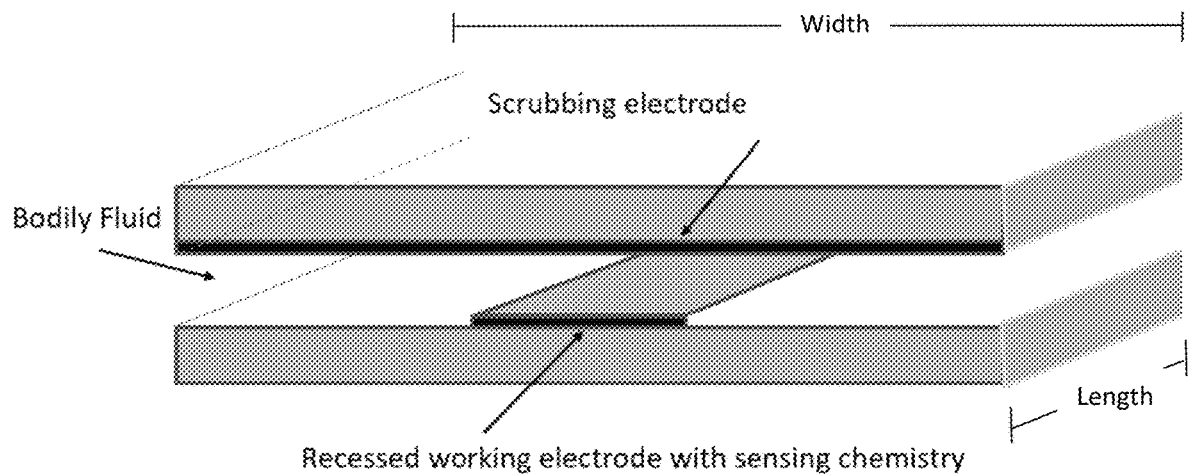
FIG. 10 is a depiction of a sensor electrode configuration comprising a scrubbing electrode, in accordance with one or more aspects of the present disclosure.

Various electrode configurations may be used to ensure that bodily fluid contacts the scrubbing electrode prior to the working electrode. One such non-limiting configuration is shown in FIG. 10. As shown, the scrubbing electrode and the working electrode are in facing relationship and the working electrode is recessed, or otherwise of a lesser width, compared to the scrubbing electrode. Although the particular configuration of the working electrode and scrubbing electrode shown in FIG. 10 is in the shape of a rectangle, other configurations may be equally applicable to the embodiments described herein, such as square, round, helical, and the like. Generally, the working electrode and the scrubbing electrode may have a length that is greater than its width.

In one or more aspects, the width of the scrubbing electrode to the working electrode may be in the range of about 2:1 to about 50:1, encompassing any value and subset therebetween. For example, in some instances, the scrubbing electrode may have a width in the range of about 300 µm to about 5000 and the working electrode may have a width in the range of about 100 µm to about 1000 encompassing any value and subset therebetween. These dimensions incorporate orientations in which the thin layer may extend up the length of the sensor tail, having a linear or non-linear shape, in order to increase the ratio between the size of scrubbing electrode and the size of the working electrode, without making the sensor tail too wide for practical in vivo use (insertion).

A thin layer is formed between the scrubbing electrode and the working electrode. This thin layer may be in the range of about 10 µm to about 100 encompassing any value and subset therebetween. In some instances, the thin layer may be about 50 The thin layer is generally formed by sealing fluid passage along two opposing edges of the scrubbing electrode (e.g., a thin layer "cell"), such that bodily fluid can enter the space between the unsealed thin layer space in a controlled fashion to ensure that it reaches the scrubbing electrode prior to the working electrode. In general, a larger ratio between the scrubbing electrode surface area to the thin layer volume may be preferred to maximize the opportunity for solutes (e.g., interferents) to interact with the scrubbing electrode. For example, with reference to FIG. 10, the thin layer between the scrubbing electrode and the working electrode may be formed by applying an adhesive, spacer, or other non-limiting separation means along the width edges of the electrodes. As such, bodily fluid is directed through the edges along the length. Accordingly, when bodily fluid, including interferents and the analyte of interest, diffuse through the thin-layer, there is ample interaction with the scrubbing electrode before reaching the working electrode. As such, analyte sensors comprising such scrubbing electrodes need not, although may, rely on a membrane to limit interferent interaction with the working electrode, which may provide manufacturing and cost benefits.

In various embodiments, the thin layer may be modified with a surfactant, hydrogel, membrane, or other material aid in channeling the bodily fluid into the thin layer, to aid in biocompatibility, to provide a microbicidal or microstatic quality, and the like, and any combination thereof.

In one or more aspects, the scrubbing electrode may be independently controlled, such as by adjusting the scrubbing electrode potential in order to fine-tune its reaction effectiveness with particular interferents. In general, the effectiveness of the scrubbing electrode to react with interferents will increase with higher potentials. The scrubbing electrode potential may be in the range of about −1000 mV to about +1000 mV, encompassing any value and subset therebetween. In general, the scrubbing electrode potential may be any working potential within the potential window of water; that is, the potential at which water, the relevant solvent for bodily fluids, is not itself oxidized or reduced. The scrubbing electrode potential may be relative to an included reference electrode (e.g., a Ag/AgCl reference electrode), which may be shared by both the scrubbing electrode and working electrode, in some embodiments. Furthermore, running the scrubbing electrode at generally negative potentials may enable the additional scrubbing of oxidizing agents, such as oxygen, which may be beneficial depending on the analyte of interest. That is, the scrubbing electrode may be used to scavenge oxygen to decrease its contribution to analyte signal.

The composition of the scrubbing electrode is not considered to be particularly limiting and may be made of known electrode materials, and may be the same or of different composition than the working electrode. Examples of suitable materials include, but are not limited to, carbon, gold, platinum, PEDOT, and the like. In some instances, the composition of the scrubbing electrode may be modified or supplemented with a material specific for reaction with an interferent of interest or to increase the surface area of the scrubbing electrode, among other advantages. It is further to be appreciated, that an interferent-reactant species may be coated upon the scrubbing electrode in any manner, as described hereinabove, in order to further enhance the elimination or reduction of interferents reaching the working electrode.

In some embodiments, rather than having a thin layer configuration for incorporation of a scrubbing electrode, the scrubbing electrode composition may be selected such that it is permeable to the analyte of interest. In such a manner, the scrubbing electrode may be layered above the working electrode, having an analyte permeable membrane or dielectric layer therebetween to avoid shorting of the sensor, and no thin layer. That is, an insulating material that is itself permeable to the analyte of interest is disposed between the permeable scrubbing electrode and the working electrode comprising the analyte sensing material. In such a manner, and based on the same rationale as the thin layer scrubbing electrode configurations described above, bodily fluid, comprising both the analyte of interest and interferents, will come into contact with the permeable scrubbing electrode where interferents react and are eliminated or otherwise reduced in concentration prior to the bodily fluid (comprising the analyte of interest and no or less interferents) coming into contact with the working electrode. Therefore, the scrubbing electrode can eliminate or reduce the local concentration of an interferent present at or accessible to the working electrode, thereby eliminating or reducing signal attributed to such interferents because the interferents never reach excess area of a working electrode.

Figure 11:
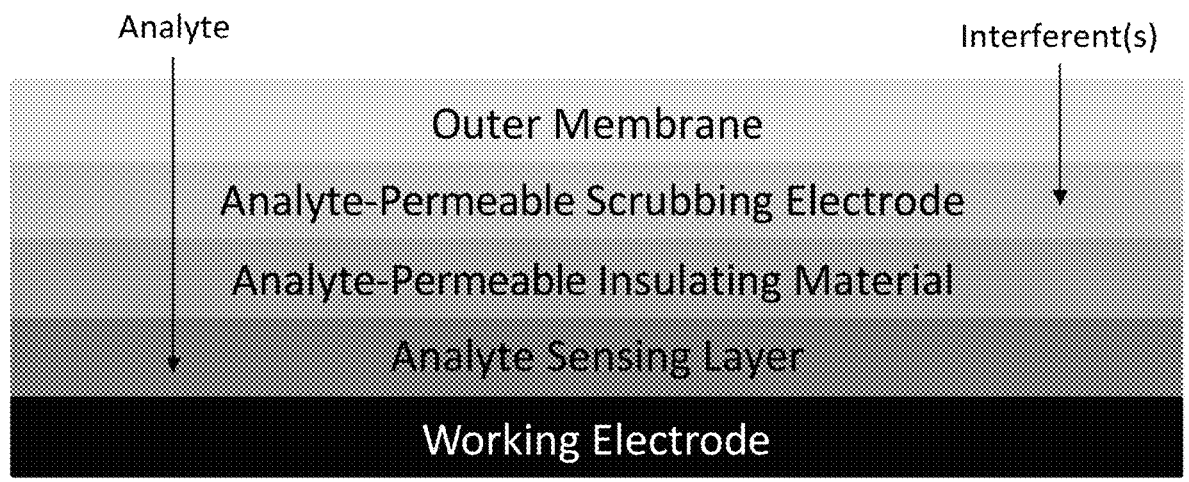
FIG. 11 is a depiction of a sensor electrode configuration comprising a permeable scrubbing electrode, in accordance with one or more aspects of the present disclosure.
Figure 25:
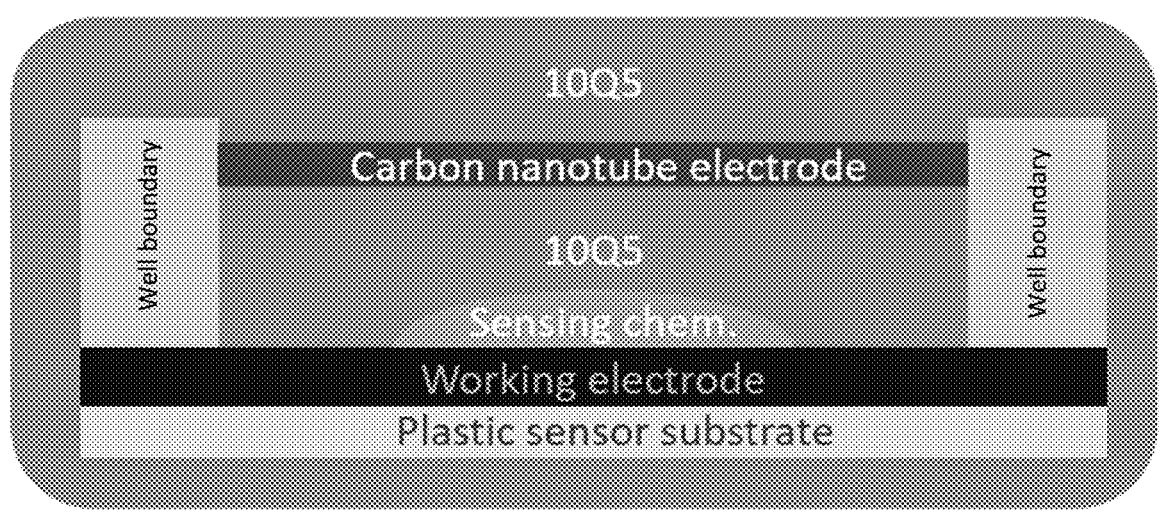
FIG. 25 is a sensor configuration for inclusion of a permeable scrubbing electrode, according to one or more aspects of the present disclosure.

One such non-limiting configuration of an analyte sensor comprising a permeable scrubbing electrode is shown in FIG. 11. As shown, a working electrode comprises sensing chemistry disposed thereupon to form an active area (as a single area or comprising multiple discontiguous spots). Upon the active area is an analyte-permeable insulating material, such as any of the polymers described herein, provided that the analyte of interest can diffuse therethrough. For example the analyte-permeable insulating layer may be a diffusion-limiting membrane. The analyte-permeable scrubbing electrode is disposed upon the diffusion-limiting membrane. While the analyte-permeable scrubbing electrode needs to be the same dimensions as the base working electrode, in preferred embodiments, the analyte-permeable scrubbing electrode has a shape and size that contacts bodily fluid prior to either of the insulating layer or the working electrode. An outer membrane may be included to provide additional diffusion-limiting qualities, biocompatibility qualities, microbicidal or microstatic qualities, protection of the permeable scrubbing electrode, and the like, and any combination thereof. As shown in FIG. 11, an interferent can diffuse through the outer membrane to the permeable scrubbing electrode, where it reacts and is rendered inactive such that it cannot contribute to the measured signal at the working electrode. Differently, the analyte of interest is not reactive with the scrubbing electrode (which has no analyte sensing chemistry) and the analyte diffuses through the outer membrane, the scrubbing electrode, and the insulating material to the sensing layer upon the working electrode. Another non-limiting configuration, as shown in FIG. 25 discussed below, may employ a "well" structure having an analyte-permeable scrubbing electrode.

Figure 12:
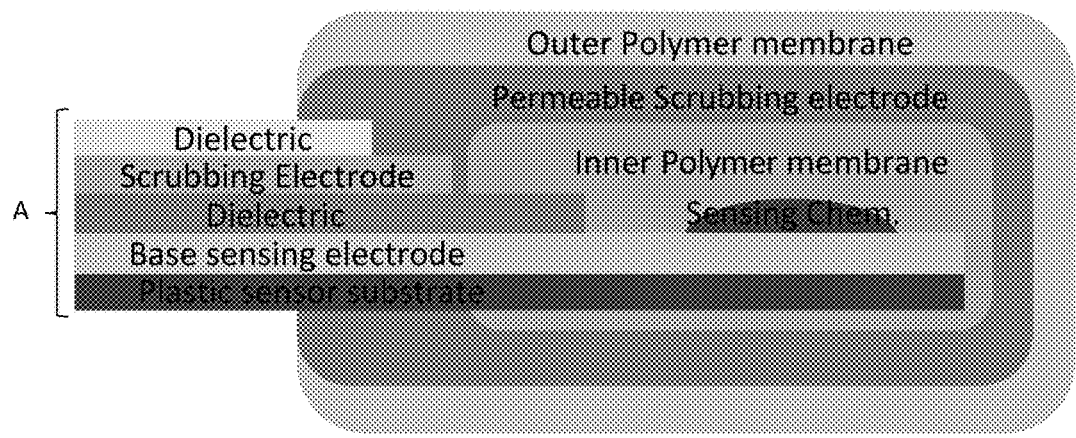
FIG. 12 is a depiction of a sensor electrode configuration comprising a non-permeable scrubbing electrode and a permeable scrubbing electrode, in accordance with one or more aspects of the present disclosure.

Another non-limiting configuration of an analyte sensor comprising a permeable scrubbing electrode is shown in FIG. 12. In this configuration, the permeable scrubbing electrode is provided in combination with a non-permeable scrubbing electrode trace to provide electrical contact such that a potential can be applied to the permeable scrubbing electrode. The non-permeable scrubbing electrode may be traced upon the dielectric material and sensing chemistry dispensed upon an exposed portion of the working electrode. The portion of the sensor A may be produced and singulated. Thereafter, it may be dip-coated to apply the inner polymer membrane and cured, then dip-coated to apply the permeable scrubbing membrane and cured, then finally dip-coated to apply the outer polymer membrane. This configuration may provide manufacturing and cost benefits.

Figure 27A:
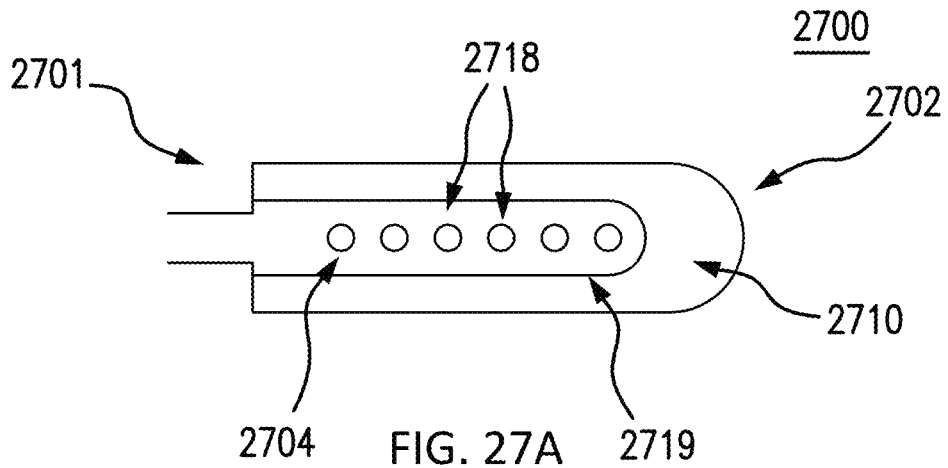
FIG. 27A is a top view of an electrode layer having a U-shaped gap thereon according to one or more aspects of the present disclosure.

FIG. 27A shows a top view of another non-limiting configuration of the analyte sensor of FIG. 5. In this example embodiment, electrode layer 2700 includes an elongate body comprising a proximal end 2701 and a distal end 2702. The electrode layer 2700 can have an first active working electrode area 2704 disposed thereon comprising at least one sensing spot 2718 with at least one analyte responsive enzyme disposed there on. Only portions of electrode layer 2700 comprising the sensing spots 2718 contribute signal associated with an analyte of interest when the analyte interacts with the active area 2704. Although electrode layer 2700 shows six sensing spots 2718 within the active area 2704, it is to be appreciated that fewer or greater than six sensing spots 2718 can be included upon electrode layer 2700, without departing from the scope of the present disclosure. Indeed, sensing spots 2718 can have any configuration described herein, without limitation.

The electrode layer 2700 also includes a second electrode portion 2710 and at least one gap 2719 which separates the active area 2704 from the second electrode portion 2710. In the illustrated embodiment the U-shaped gap 2719 extends from the proximal end 2701 of the elongate body on a first side of the first active working electrode area to proximate the distal end 2701 of the elongate body of the electrode layer, and back to the proximal end of the elongate body on a second side of the first active working electrode area 2704. The gap 2719 and the second electrode portion 2710 do not comprise any sensing chemistry and, accordingly, analytes of interest do not react therewith. Furthermore, because gap 2719 electrically separates the active area 2704 from the second electrode portion 2710, any interferents, such as ascorbic acid in the bodily fluid, that come into contact with the second electrode portion 2710 do not generate an interferent signal to the sensor. As such, the effective electrode area subject to potential interferents is reduced and therefore the overall interference to the sensor signal is reduced. In some embodiments, the second electrode portion 2710 is not connected to a sensor current conductive trace. Alternatively, the second electrode portion 2710 can be connected to a conductive trace as described further herein below.

Figure 27B:
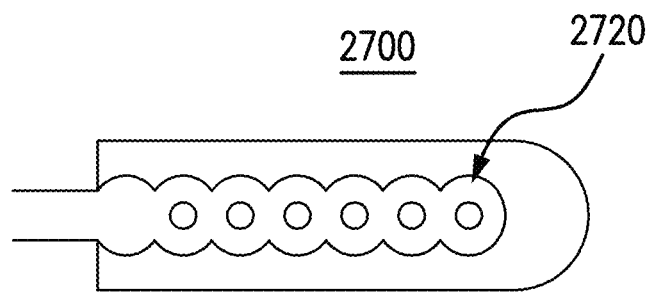
FIG. 27B is a top view of an electrode layer a wavy U-shaped gap thereon according to one or more aspects of the present disclosure.

In accordance with the disclosed subject matter, the U-shaped gap 2719 of the electrode layer 2700 of FIG. 27A, or any of the gaps disclosed herein, can have a linear configuration or a non-linear configuration. For illustration and not limitation, FIG. 27B shows a top view of an electrode layer similar to FIG. 27A, wherein the gap 2720 has a non-linear configuration. As shown, the gap includes a wavy pattern and in some embodiments, the wavy pattern can be designed to closely surround the sensing spots, which can further reduce the amount of active area 2704 to reduce the amount of sensor interference. Non-limiting examples of a other non-linear configuration include, a curly pattern, a curvy pattern, an undulating pattern, a crimped pattern or the like. As used herein, the term "U-shaped" encompasses an end that can be rounded, non-rounded, or have any suitable shape such as rectangular, and the like.

Figure 26:
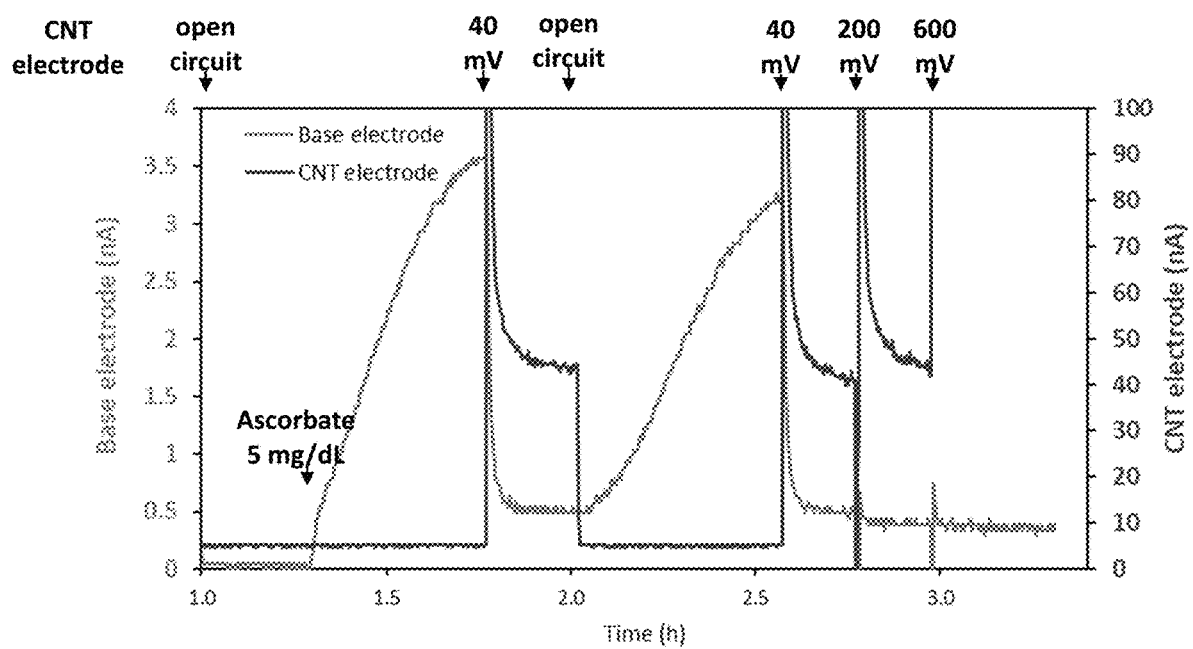
FIG. 26 is a sensor current trace of the sensor of FIG. 25, in accordance with one or more aspects of the present disclosure.
Figure 27C:
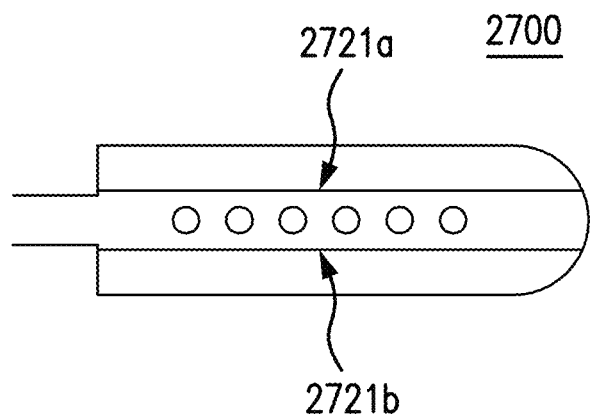
FIG. 27C is a top view of an electrode layer having laterally spaced apart gaps thereon according to one or more aspects of the present disclosure.

As one suitable alternative to the U-shape embodiment of FIGS. 27A and 27B, FIG. 27C depicts an example embodiment showing a top view of an electrode layer 2700 comprising at least two laterally spaced apart gaps 2721a and 2721b thereon. The gaps extend from the proximal end of the elongate body of the electrode layer to the distal end of the elongate body of the electrode layer on opposing sides of the first active working electrode area. The gap of FIG. 27C serves the same function as described above for FIGS. 3 27A FIGS. 3-27A including electrically separating the active area of the electrode area from the second electrode portion, thus reducing the effective size of the working electrode area subject to potential interferences to reduce signal interference.

As used herein, the term "gap" and grammatical variants thereof, means a channel or a well in the electrode layer formed by removal of the electrode layer to electrically insulate a section. Further, the at least one gap can be formed in the electrode layer during or after fabrication of the electrode layer by a variety of non-limiting techniques, for example, photolithography, or screen printing. The at least one gap in the electrode layer has a has a width of about 1 μm to about 100 μm.

Figure 28:
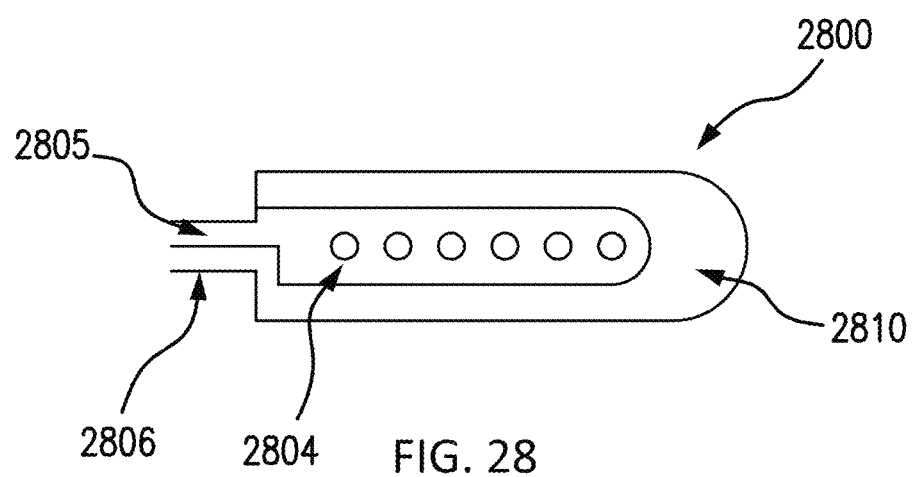
FIG. 28 is a top view of an electrode layer having second electrode portion connected to a second scrubbing electrode trace according to one or more aspects of the present disclosure.

Another non-limiting configuration of the disclosed subject matter includes a scrubbing electrode which can be connected to a scrubbing electrode sensor current conductive trace as shown in FIG. 28. Particularly, for the purpose of illustration and not limitation, FIG. 28 is an embodiment showing a top view of an electrode layer 2800 having a first active working electrode area 2804 disposed thereupon and the first active working electrode area can be connected to a first sensor current conductive trace 2805. While otherwise similar to the embodiment of FIG. 27A, in this configuration, a second electrode portion 2810, which is separated from the working electrode area via a gap, can be configured as a scrubbing electrode and can be connected to a second sensor current conductive trace 2806 such that a potential can be applied to the scrubbing electrode. As such, the scrubbing electrode 2810 can configured to oxidize or pre-react with an one or more interferents, such as not-limited to ascorbic acid, before it is able to react on the active working electrode area of the analyte sensor. Accordingly, the scrubbing electrode can eliminate or reduce the local concentration of an interferent present at or accessible to the active working electrode are, thereby eliminating or reducing signal attributed to such interferents because the interferents never reach the active area of a working electrode.

In one or more aspects, the scrubbing electrode 2810 may be independently controlled, such as by adjusting the scrubbing electrode potential in order to fine-tune its reaction effectiveness with particular interferents. In general, the effectiveness of the scrubbing electrode 2810 to react with interferents will increase with higher potentials. The scrubbing electrode potential may be in the range of about −1000 mV to about +1000 mV, encompassing any value and subset therebetween. In general, the scrubbing electrode potential may be any working potential within the potential window of water; that is, the potential at which water, the relevant solvent for bodily fluids, is not itself oxidized or reduced. The scrubbing electrode potential may be relative to an included reference electrode (e.g., a Ag/AgCl reference electrode), which may be shared by both the scrubbing electrode and working electrode, in some embodiments. Furthermore, running the scrubbing electrode at generally negative potentials may enable the additional scrubbing of oxidizing agents, such as oxygen, which may be beneficial depending on the analyte of interest. That is, the scrubbing electrode may be used to scavenge oxygen to decrease its contribution to analyte signal.

In yet another non-limiting configuration the present disclosure demonstrates how extraneous carbon area 510 as shown in FIG. 5 may be decreased in carbon working electrode 500 while still retaining functionality for producing a signal associated with an analyte of interest and minimizing or eliminating interferent signal. In particular, the pitch and diameter of the discontiguous sensing spots 518 of conventional carbon working electrode 500 may be reduced, as well as the configuration of the discontiguous sensing spots 518 relative to one another, to decrease the area of extraneous carbon area 510. As used herein, the term "grid," and grammatical variants thereof, refers to a 2D arrangement of active areas along the length of the working electrode (the length along the axis of the sensor tail 104 (FIG. 1) extending from the sensor housing 103 and into a bodily fluid) to the width of the working electrode.

Figure 29A:
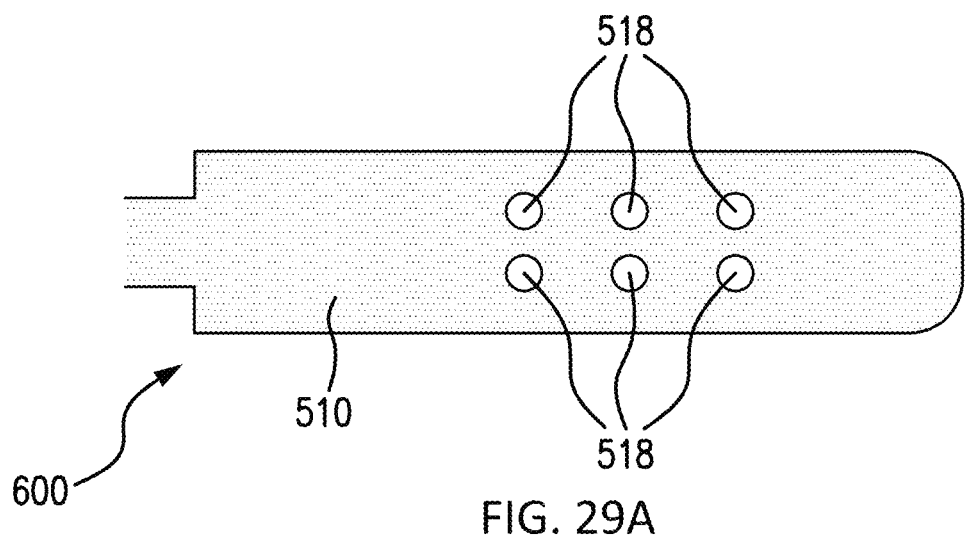
FIG. 29A shows a cross-sectional diagram of an active area grid configuration of a carbon working electrode suitable for use in the analyte sensors of the present disclosure.
Figure 29B:
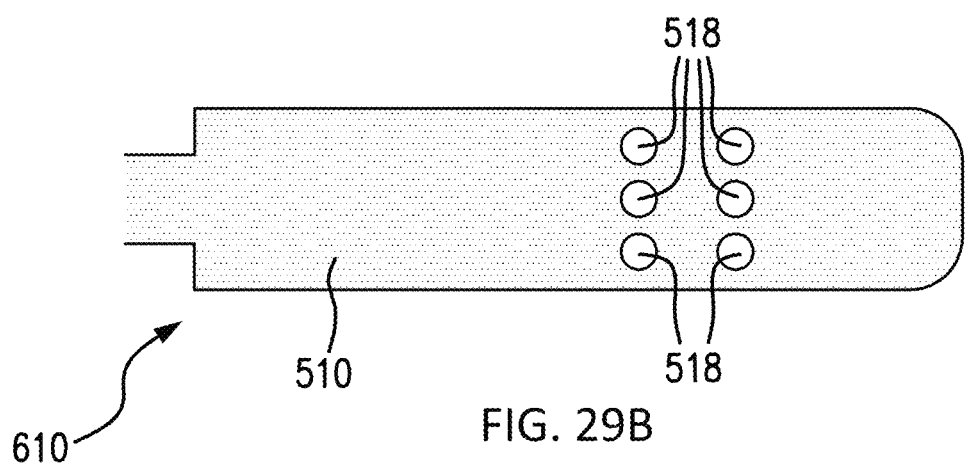
FIG. 29B shows another active area grid configuration.

For illustration of various grid configurations, the active areas of the present disclosure may be in the form of a 1×n grid, wherein n is an integer greater than 1, such as in the range of 2 to about 20, or 2 to about 10, encompassing any value and subset therebetween. In some embodiments, the active area may comprise discontiguous sensing spots in the form of a 1×6 grid, as shown in FIG. 5, for example. Other grid configurations of the active areas may be employed in the embodiments described herein, such as those illustrated in FIGS. 29A through 29B, which may be best understood with reference to FIG. 5, where like elements retain like labels. For example, in some embodiments, the active areas may comprise discontiguous sensing spots in the form of a 2×n grid, where n is an integer of 2 to about 10, or 2 to about 5, encompassing any value and subset therebetween. FIG. 29A depicts carbon working electrode 600 having a 2×3 grid of sensing spots 518 and extraneous carbon area 510. In yet other embodiments, the active area may comprise discontiguous sensing spots in the form of a 3×n grid, where n is an integer of 2 to about 6, or 2 to about 3, encompassing any value and subset therebetween. FIG. 29B depicts carbon working electrode 610 having a 3×2 grid of sensing spots 518 and extraneous carbon area 510. Notably, each of FIGS. 5, 29A, and 29B, while showing various differing grid configurations for use in the embodiments described herein, each retain the same area of extraneous carbon area 510, because the area of the carbon electrode 500, 600, and 610, respectively, has not yet been reduced in the FIGS. As can be appreciated, the grid configurations in FIGS. 29A and 29B, are disposed over a shorter longitudinal distance than is the grid configuration in FIG. 5, thereby offering the possibility of decreasing the sensor area have exposed working electrode.

Figures 30A, 30B, 30C, 30D, 30E, 30F:
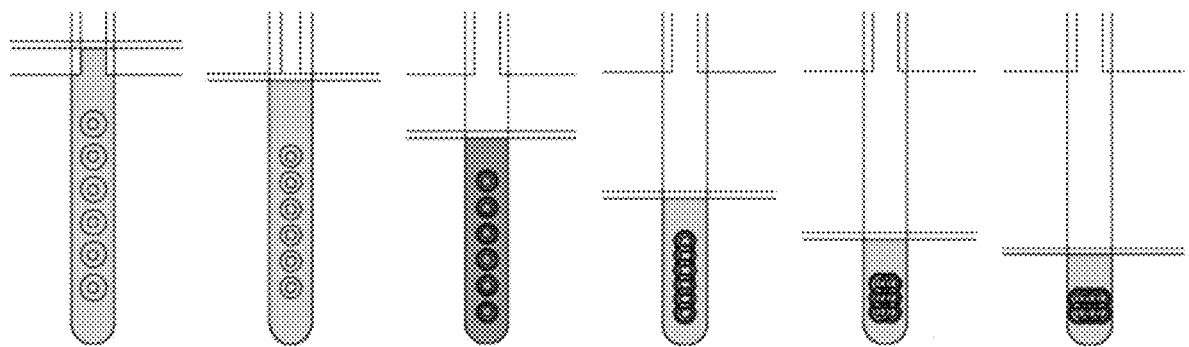
FIG. 30A is a diagram showing a top view of a working electrode having an active area thereon.
FIGS. 30B-30F show diagram of an illustrative process whereby a carbon working electrode and active area thereon may be enhanced to reduce interferent signals.

The embodiments of the present disclosure utilize grid configurations, pitch distance, active area and/or sensing spot size reduction, and active area location on the sensor tail to minimize extraneous carbon area and, thus, minimize signals associated with interferents, as illustrated in FIGS. 30A through 30E, showing top views of carbon electrodes having various active area configurations. FIG. 30A represents a control (or conventional) 1×6 active area configuration, similar to that shown in FIG. 5. The extraneous carbon area of FIG. 30A is represented as the shaded working electrode surface, absent the active areas. Each of FIGS. 30B through 30F are made with reference to FIG. 30A, and demonstrate embodiments of the present disclosure.

Each of FIGS. 30B to 30F each take advantage of reducing sensing spot pitch to reduce the extraneous carbon area, and in some embodiments merge together such that the each sensing spot is no longer discontiguous. In addition, FIG. 30B further illustrates a reduction in the pitch between adjacent sensing spots, thereby permitting the reduction of extraneous carbon area, represented as the shaded working electrode surface (below the double line), absent the sensing spots. FIG. 30C illustrates the pitch reduction of FIG. 30B, in combination with a shift of the active area toward the tip of the sensor tail, thereby permitting even further reduction of extraneous carbon area, represented as the shaded working electrode surface (below the double line), absent the sensing spots. FIG. 30D represents further pitch reduction compared to FIG. 30C, thereby permitting even further reduction of extraneous carbon area, represented as the shaded working electrode surface (below the double line), absent the sensing spots. FIG. 30E represents the pitch reduction of FIG. 30D and the sensor tail shift of FIG. 30C, in combination with a 2×3 active area grid configuration, thereby permitting even further reduction of extraneous carbon area, represented as the shaded working electrode surface (below the double line), absent the active area. FIG. 30F represents the pitch reduction of FIG. 30D and the sensor tail shift of FIG. 30C, in combination with a 3×3 active area grid configuration, thereby permitting even further reduction of extraneous carbon area, represented as the shaded working electrode surface (below the double line), absent the sensing spots. FIGS. 30D through 30F illustrate that as pitch reduction is increased, the sensing spots become less distinguishable and may, in some embodiments, be representative as a single active area lacking discontiguous sensing spots.

For illustrative purposes, Table 1 compares FIG. 30A, FIG. 30B, and FIGS. 30D through 30F based on extraneous carbon reduction percentages to estimate (Est.) the reduction in interferent (e.g., ascorbic acid) signal. The interference is measured in relation to signal strength based on the tested analyte concentration and the known interferent concentration.

TABLE 1

| Design | FIG. 30A Control | FIG. 30B Pitch | FIG. 30D 1 × 6 Grid | FIG. 30E 2 × 3 Grid | FIG. 30F 3 × 2 Grid |
|---|---|---|---|---|---|
| Extraneous Carbon Reduction | — | −26% | −49% | −64% | −69% |
| Spot Diameter Reduction | — | — | −6% | −17% | −20% |
| Interferent Signal Reduction | — | −26% (Est.) | −46% (Est.) | −54% (Est.) | −58% (Est.) |

As shown in Table 1, as the extraneous carbon area is reduced, the interferent signal reduction is also reduced, nearly linearly.

The embodiments of the present disclosure permit at least a reduction in interferent signal, such as ascorbic acid, in the range of greater than about 20%, such as in the range of about 20% to about 60% or greater, and preferably at least about 40% greater, at least about 45% greater, or at least about 50%, encompassing any value and subset therebetween.

The present disclosure provides reduced area working electrodes (e.g., carbon electrodes) having one or more active areas disposed thereupon. In some embodiments, a plurality of discontiguous active areas are disposed upon the working electrodes. Generally, the discontiguous active areas of the present disclosure have widths (diameters) in the range of from about from 50 μm to about 300 μm, encompassing any value and subset therebetween. Non-round active areas (not shown) may have area ranges equivalent to that of circular features with the foregoing width (diameter) ranges. The pitch between each discontiguous active area (the distance between adjacent active areas) may be about 50 μm to about 500 μm, encompassing any value and subset therebetween. Typically, the distal most active area is located at least about 200 μm from the tip of the working electrode (which may be identical to the tip of the sensor tail) to be located most distally into bodily fluid, including in the range of about 50 μm to about 500 μm, encompassing any value and subset therebetween.

In total, the working electrode, including active area (which a single active area or a plurality of discontiguous active areas), may have an area in the range of about 0.1 mm2 to about 2 mm2, encompassing any value and subset therebetween. In total, the extraneous working electrode area (less any active area(s)) may be in the range of about 0.01 mm2 to about 1.8 mm2, encompassing any value and subset therebetween.

To achieve reduced extraneous working electrode area to reduce interferent signal, while maintaining sensitivity to the analyte or analytes of interest, the ratio of the area of extraneous working electrode to the area of the active area may be in the range of about 1:10 to about 10:1, encompassing any value and subset therebetween. This ratio is maintained regardless of the grid configuration or pitch distance of the analyte sensors described herein; that is, the ratio range of the area of extraneous working electrode to the area of the active area always is always in this range to achieve the desired benefits described herein.

Accordingly, an analyte sensor of the present disclosure may comprise: a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1. The working electrode may be a carbon electrode. At least the sensing portion may have a mass transport limiting membrane overcoated thereupon.

Further, a method of the present disclosure may comprise: exposing an analyte sensor to a bodily fluid, the analyte sensor comprising a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1. The working electrode may be a carbon electrode. At least the sensing portion may have a mass transport limiting membrane overcoated thereupon.

Accordingly, an analyte sensor of the present disclosure may comprise: a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1. The working electrode may be a carbon electrode. At least the sensing portion may have a mass transport limiting membrane overcoated thereupon.

Further, a method of the present disclosure may comprise: exposing an analyte sensor to a bodily fluid, the analyte sensor comprising a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1. The working electrode may be a carbon electrode. At least the sensing portion may have a mass transport limiting membrane overcoated thereupon.

Further non-limiting configurations of the present disclosure demonstrate additional embodiments of how extraneous carbon area 510 as shown in FIG. 5 may be decreased in carbon working electrode 500 while still retaining functionality for producing a signal associated with an analyte of interest and minimizing or eliminating interferent signal. In particular, the pitch and/or diameter of the sensing spots 518 of carbon working electrode 500 may be reduced, as well as the configuration of the sensing spots 518 relative to one another, to decrease the area of extraneous carbon area 510.

Figure 31A:
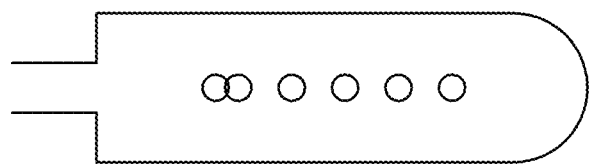
FIG. 31A is a diagram showing a top view of a working electrode having active area thereon including first and second adjacent sensing spots in an overlapping configuration.
Figure 31B:
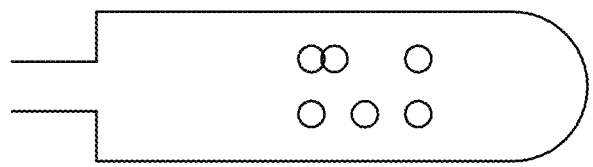
FIG. 31B-31F depict top views of example embodiments including of configurations of first and second adjacent sensing spots in an overlapping configuration according to one or more aspects of the present disclosure.
Figure 31C:
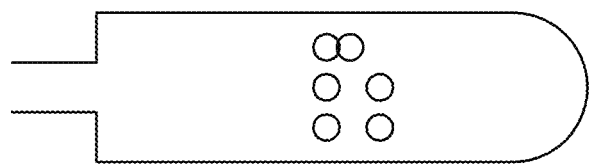
Figure 31D:
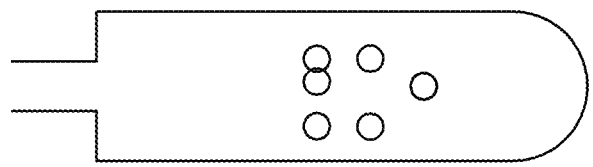
Figure 31E:
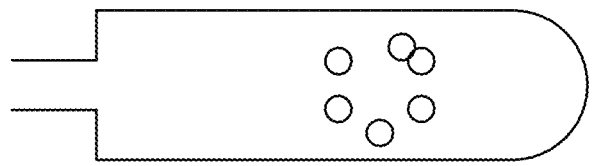
Figure 31F:
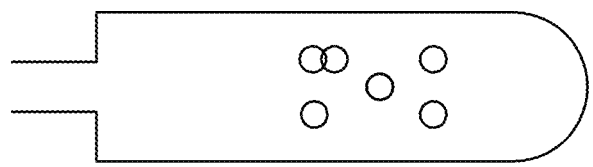

For example, an analyte sensor includes an electrode layer having an elongate body comprising a proximal end and a distal end. The electrode layer includes a first active working electrode area having a plurality of sensing spots with at least one analyte-responsive enzyme disposed thereupon. First and second adjacent sensing spots in the first active working electrode area are in an overlapping configuration, as shown in FIGS. 31A to 31F. As illustrated, each embodiment takes advantage of reducing adjacent sensing spot pitch to reduce the extraneous carbon area, by merging together at least first and second adjacent sensing spots to be in an overlapping configuration. As defined herein, "overlapping" means that the boundaries of at least two adjacent sensing spots at least touch each other whereby the adjacent sensing spots are no longer discontiguous. For example, FIG. 31A illustrates a reduction in the pitch between first and second adjacent sensing spots, such that the first and second sensing spots can be in an overlapping configuration, thereby permitting the reduction of extraneous carbon area of the electrode layer, for example by reducing the length of electrode needed to contain the sensing spots. FIG. 31B illustrates reduction in pitch between the first and second adjacent sensing spots arranged in a 3×2 grid configuration, such that the first and second adjacent sensing spots can be in an overlapping configuration. FIG. 31C illustrates reduction in pitch between the first and second adjacent sensing spots arranged in a 2×3 grid configuration, such that the first and second adjacent sensing spots can be in an overlapping configuration. FIGS. 31D through 31F further illustrate reduction in pitch between the first and second adjacent sensing spots arranged in non-linear configurations, such that the first and second adjacent sensing spots can be in an overlapping configuration. Other suitable configurations utilizing overlapping sensing spots are contemplated and within the scope of the disclosed subject matter.

Figure 32A:
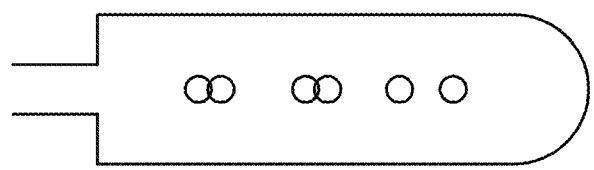
FIG. 32A-32D depict top views of example embodiments including configurations of at least two adjacent sensing spots in an overlapping configuration according to one or more aspects of the present disclosure.

In some embodiments, third and fourth adjacent sensing spots in the first active working electrode area are also in an overlapping configuration. For example, FIG. 32A illustrates an example embodiment of the reduction in the pitch between third and fourth adjacent sensing spots in a linear configuration permitting the reduction of extraneous carbon area of the electrode layer, wherein the third and fourth sensing spots can be in an overlapping configuration.

Figure 32B:
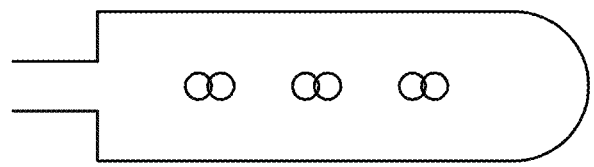
Figure 32C:
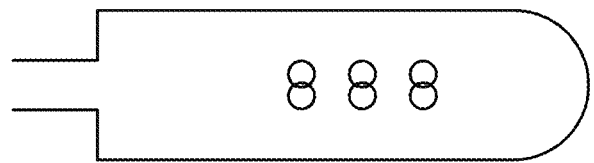
Figure 32D:
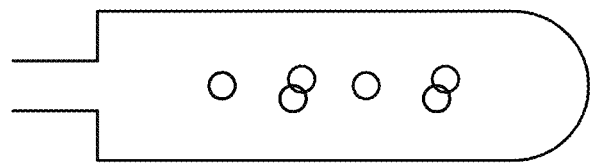

In some embodiments, fifth and sixth adjacent sensing spots in the first active working electrode area are also in an overlapping configuration. For example, FIG. 32B illustrates an embodiment of the reduction in the pitch between three pairs of adjacent spots in a linear configuration permitting the reduction in extraneous carbon area of the electrode layer, wherein the each pair of adjacent sensing spots can be in an overlapping configuration. Further, FIG. 32C illustrates an example embodiment of reduction in the pitch between three pairs of adjacent spots in a grid configuration, whereby each pair of adjacent sensing spots are in an overlapping configuration. In some embodiments, all the plurality of sensing spots in the first active working electrode area can be in an overlapping configuration FIG. 32D illustrates an example embodiment of reduction in the pitch between at least two adjacent sensing spots, wherein the sensing spots are arranged in a non-linear configuration with alternating single and double spots along a length thereof.

Figure 33:
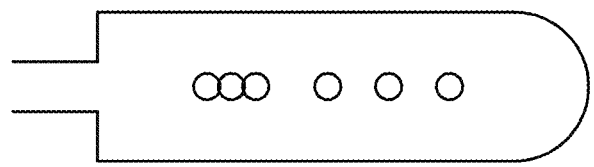
FIG. 33 depicts a top view of an example embodiment including at least three adjacent sensing spots in an overlapping configuration according to one or more aspects of the present disclosure.

FIG. 33 illustrates an example embodiment of the reduction in the pitch between at least three adjacent sensing spots permitting the reduction of extraneous carbon area of the electrode layer, wherein the sensing spots can be in a linear configuration and the at least three adjacent sensing spots are in an overlapping configuration. It is to be noted that the at least three sensing spots can have any configuration described herein, without limitation.

While the shape of the sensing spots are illustrated as round in FIGS. 32A-D and 33, any other suitable shape could be used including substantially spherical, circular, square, rectangular, triangular, conical, or elliptical, or a combination thereof.

Figure 34A:
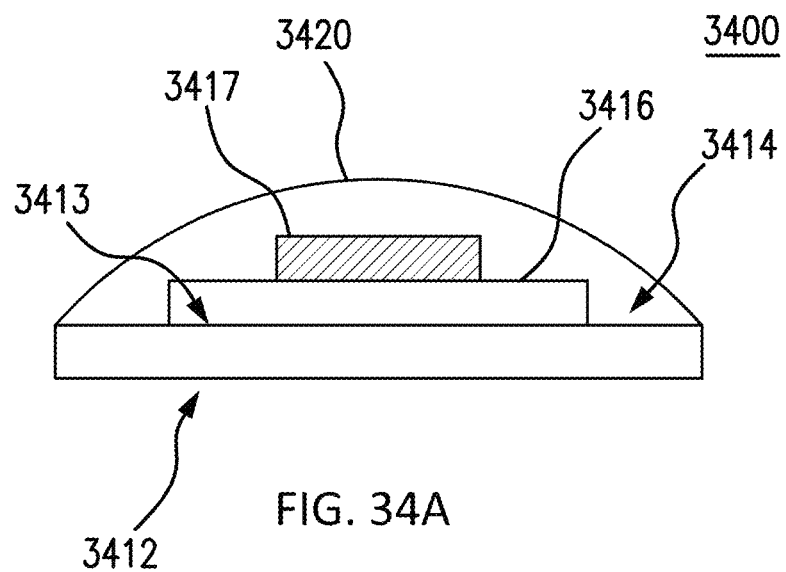
FIG. 34A is a cross-sectional diagram of an example embodiment having a substrate having a conventional working electrode and a membrane disposed thereupon according to one or more aspects of the present disclosure.

Another non-limiting example embodiment is illustrated in FIG. 34A. Particularly, analyte sensor 3400 comprises substrate 3412 having an upper surface including a first portion 3413 and a second exposed portion 3414. A working electrode layer 3416 can be disposed only upon the first portion 3413 of the upper surface of the substrate such that the second exposed portion of the substrate is not covered by the electrode layer. The working electrode can have a first active working electrode area disposed thereupon with a single or multiple sensing spots 3417 configured for detecting on an analyte, as discussed further herein. A membrane 3420 can cover at least a portion of the electrode layer 3416 and the second exposed portion of the substrate 3414. The membrane can directly cover and contact both the electrode layer and the second exposed portion of the substrate. As such, the membrane 3420 attaches to the second exposed portion of the substrate 3414.

Figure 34B:
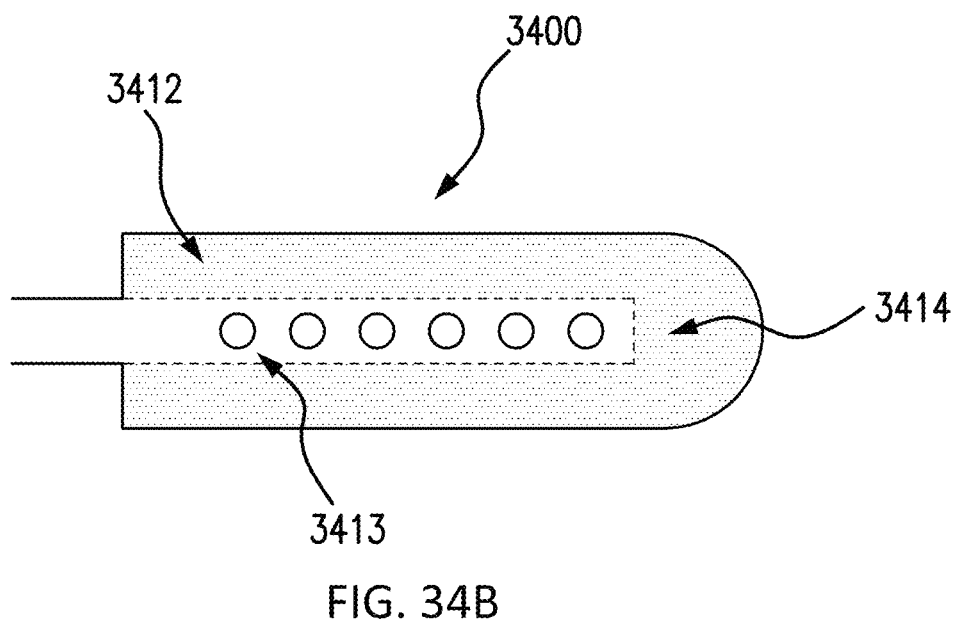
FIG. 34B is a top view of the embodiment of FIG. 34A illustrating a substrate having a rough second exposed portion.

As illustrated in FIG. 34B, in some embodiments, the surface of the second exposed portion of the substrate 3414 can have a rough surface to facilitate a secure attachment of the membrane 3420 to the second exposed portion of the substrate 3414. As used herein, a rough surface means on the surface having irregularities to provide increased surface area for the attachment of the membrane 3420. In one or more aspects of the present disclosure, second exposed portion of the substrate can be roughened using physical or chemical processing techniques. In non-limiting examples, the surface of the substrate can be roughened by subjecting it to etching, bombarding the surface of the substrate with ions, embossing the surface of the substrate, or using a laser. The roughened second exposed portion of the substrate can have any suitable roughness value.

In one or more aspects of the present disclosure, the substrate can comprise a material compatible with the material of the working electrode. In a non-limiting example, the substrate can comprise polymeric materials, such as polyester, polyimide and combinations thereof. The membrane can comprise a material compatible with the material of the substrate 3412. In particular embodiments of the present disclosure, the membrane covering one or more active areas may comprise a crosslinked polyvinylpyridine homopolymer or copolymer. In certain embodiments, the mass transport limiting membrane discussed above is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like. Further, the membrane may be formed by crosslinking in situ a polymer, including those discussed above, modified with a zwitterionic moiety, a non-pyridine copolymer component, and optionally another moiety that is either hydrophilic or hydrophobic, and/or has other desirable properties, in a buffer solution (e.g., an alcohol-buffer solution). The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, and the like, and any combinations thereof, may be used to enhance the biocompatibility of the polymer or the resulting membrane. Further, the membrane may comprise a compound including, but not limited to, poly(styrene-co-maleic anhydride), dodecylamine and poly(propylene glycol)-block-poly(ethylene glycol)-block-poly(propylene glycol) (2-aminopropyl ether) cross-linked with poly(propylene glycol)-block-poly(ethylene glycol)-block-poly(propylene glycol) bis(2-aminopropyl ether); poly(N-isopropyl acrylamide); a copolymer of poly(ethylene oxide) and poly(propylene oxide); polyvinylpyridine; a derivative of polyvinylpyridine; polyvinylimidazole; a derivative of polyvinylimidazole; polyvinylpyrrolidone (PVP), and the like; and any combination thereof. In some embodiments, the membrane may be comprised of a polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group. Other membrane compounds, alone or in combination with any aforementioned membrane compounds, may comprise a suitable copolymer of 4-vinylpyridine and styrene and an amine-free polyether arm.

The membrane compounds described herein may further be crosslinked with one or more crosslinking agents, including those listed herein with reference to the enzyme described herein. For example, suitable crosslinking agents may include, but are not limited to, polyethylene glycol diglycidylether (PEGDGE), glycerol triglycidyl ether (Gly3), polydimethylsiloxane diglycidylether (PDMS-DGE), or other polyepoxides, cyanuric chloride, N-hydroxysuccinimide, imidoesters, epichlorohydrin, or derivatized variants thereof, and any combination thereof. Branched versions with similar terminal chemistry are also suitable for the present disclosure. For example, in some embodiments, the crosslinking agent can be triglycidyl glycerol ether and/or PEDGE and/or polydimethylsiloxane diglycidylether (PDMS-DGE).

In some embodiments, the membrane composition for use as a mass transport limiting layer of the present disclosure may comprise polydimethylsiloxane (PDMS), polydimethylsiloxane diglycidylether (PDMS-DGE), aminopropyl terminated polydimethylsiloxane, and the like, and any combination thereof for use as a leveling agent (e.g., for reducing the contact angle of the membrane composition or active area composition). Branched versions with similar terminal chemistry are also suitable for the present disclosure. Certain leveling agents may additionally be included, such as those found, for example, in U.S. Pat. No. 8,983,568, the disclosure of which is incorporated by reference herein in its entirety.

Figure 35A:
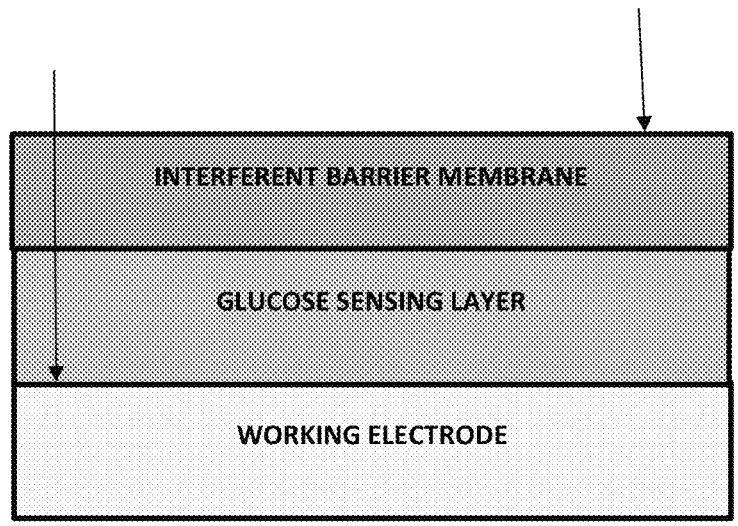
FIGS. 35A and 35B are sensor configurations including of an interferent-barrier membrane layer, according to one or more aspects of the present disclosure.
Figure 35B:
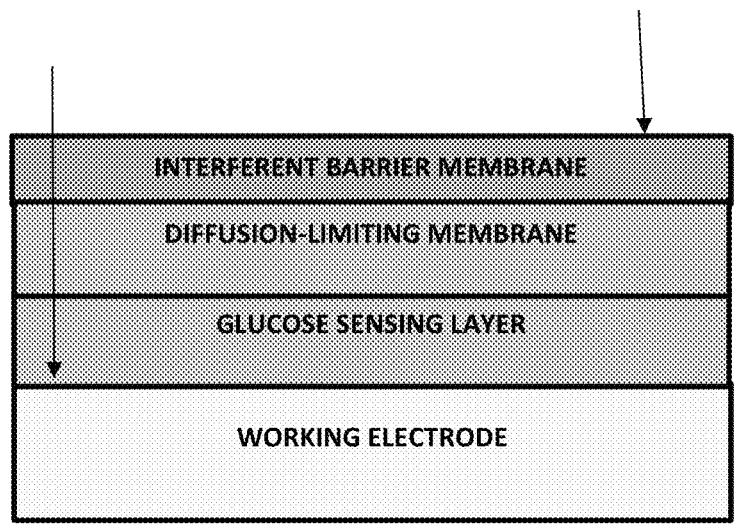

Additional non-limiting configurations of an analyte sensor including an interferent-barrier membrane layer to substantially reduce or eliminate an interferent signal of at least one interferent are shown in FIGS. 35A and 35B. As shown, an electrode layer is disposed upon a substrate (not shown), and can have an elongate body comprising a proximal end and a distal end and a first active working area of the electrode having at least one sensing spot with at least one analyte responsive enzyme disposed thereupon, as discussed herein above. The first active working area of the electrode is connected to a sensor current conductive trace. The analyte responsive enzyme disposed on the at least one sensing spot of the first active working electrode area can be a glucose, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, troponin, alcohols, aspartate, asparagine and potassium, or creatinine responsive enzyme.

In the embodiment of FIG. 35A, covering the active area is an interferent-barrier membrane layer. In some embodiments, the interferent-barrier layer can cover only the first active working area of the electrode. In additional embodiments, the interferent-barrier layer can cover the entire working electrode, i.e., the first active working area of the electrode and a second electrode portion. The interferent-barrier membrane layer can be in the form of a sheet or a film and can be made up of material that provides a barrier for one or more interferents provided that the analyte of interest can diffuse through. The interferent-barrier membrane can be made from suitable polymers, such as but not limited to, ion exchange membranes selected from, per-fluorinated sulfonic acid polymers, consisting of a polytetrafluoroethylene (PTFE) backbone. Specifically, the interferent-barrier membrane can include one or more sulfonated tetrafluoroethylene-based fluoropolymer-copolymers, (e.g., NAFION™, The Chemours Company, Wilmington, DE). Alternatively, the sulfonated tetrafluoroethylene-based fluoropolymer-copolymers can include, Flemion™ (Asahi Glass Company), Aciplex-S® (Asahi Chemicals), or Fumion® (Fumatech), Aquivion™ (Solvay Solexis) or Fumapem® FS (Fumatech) or combinations thereof. One or more of these of these polymers can also be used in combination with Nafion® in the interferent-barrier membrane. In some embodiments, a perfluorinated resin solution containing Nafion® in lower aliphatic alcohols and water (commercially available from Sigma-Aldrich, 274704) can be used. The perfluorinated resin solution can contain Nafion® at 1 to 10 wt %. The thickness of the interferent-barrier membrane layer can be in the range of from about 5 µm to about 30 µm.

In some embodiments, the analyte sensor can have one or more membrane layers in addition to the interferent-barrier membrane layer. In some embodiments, for example, a membrane, such as a diffusion limiting membrane can be included. As shown in FIG. 35B, for illustration, the sensor includes a second membrane layer (e.g., a diffusion limiting membrane) disposed upon the electrode layer and the interferent-barrier membrane layer is disposed upon (e.g., coated on) the second membrane layer. In alternative embodiments, the second membrane can be disposed upon the interferent-barrier layer. The interferent-barrier layer can be made of the same materials as described above for FIG. 35A. The diffusion limiting membrane can be made of any material, such as any of the polymers described herein, provided that the analyte of interest can diffuse therethrough. For example, the diffusion limiting membrane can include polyvinylpyridine homopolymer or copolymer.

As shown in FIGS. 35A and B, an interferent (right arrow) cannot diffuse through the interferent-barrier membrane layer where it reacts and is rendered inactive such that it cannot contribute to the measured signal at the working electrode. By contrast, the analyte of interest (left arrow) is not reactive with the interferent-barrier membrane layer and the analyte diffuses through the interferent-barrier membrane layer to the sensing layer (i.e., first active working area) disposed upon the working electrode. The interferent can be any of those described herein above, such as ascorbic acid, glutathione, uric acid, acetaminophen, isoniazid, salicylate, and combination thereof. The interferent-barrier membrane can reduce the interferent signal to less than about 10%, 5%, 2.5%, or 1% of a total signal when an electrode potential is in the range of about −100 mV to about +100 mV.

Each of the various compositions of the common layers and elements of the sensors described herein may be equally included in the embodiments comprising an analyte-permeable scrubbing electrode. The composition of the analyte-permeable scrubbing electrode is not considered to be particularly limiting, provided that it is conductive, able to react with an interferent (e.g., oxidize ascorbic acid), and permeable to the particular analyte of interest. In some instances, the permeable electrode may be composed of a carbon nanotube material. Other formulations may include, but are not limited to, conductive nanoparticles, conductive nanowires, and the like, and any combination thereof. The permeable scrubbing electrode may further be supplemented with other conductive inks or polymers to enhance conductivity, enhance permeability, enhance the physical properties of the permeable electrode, and the like, and any combination thereof. For example, PEDOT:PSS may be incorporated or impregnated with a carbon nanotube permeable scrubbing electrode composition to increase its viscosity to enhance dip-coating. In one or more aspects, electron transfer agents, such as those described herein, may be incorporated or otherwise impregnated into the porous structure of an analyte-permeable scrubbing electrode to enhance interferent scrubbing efficiency.

The thickness of the analyte-permeable electrode is not considered to be particularly limiting and may be in the range of about 1 μm to about 50 encompassing any value and subset therebetween. Without being bound by theory, the thickness of the permeable scrubbing electrode may be increased to enhance scrubbing efficiency as interferents would be exposed to a greater surface area of the scrubbing electrode, provided that the thickness does not adversely interfere with diffusion of the analyte of interest.

Without being bound by theory, in some embodiments, the scrubbing electrode (whether or not permeable) may additionally be used to regenerate the product of the analyte detection system, thereby increasing the concentration of analytes and effectively amplifying the analyte signal.

The various layers of any of the aforementioned components of the analyte sensors described herein may be deposited by any suitable means, such as, without limitation, automated dispensing or dip-coating. Electrodes may be screen printed, for example, and traces provided to make appropriate electrical connections.

Active areas within any of the analyte sensors disclosed herein may comprise one or more analyte-responsive enzymes, either acting alone or in concert within an enzyme system. One or more enzymes may be covalently bonded to a polymer comprising the active area, as can one or more electron transfer agents located within the active area.

Examples of suitable polymers within each active area may include poly(4-vinylpyridine) and poly(N-vinylimidazole) or a copolymer thereof, for example, in which quaternized pyridine and imidazole groups serve as a point of attachment for an electron transfer agent or enzyme(s). Other suitable polymers that may be present in the active area include, but are not limited to, those described in U.S. Pat. No. 6,605,200, incorporated herein by reference in its entirety, such as poly(acrylic acid), styrene/maleic anhydride copolymer, methylvinylether/maleic anhydride copolymer (GANTREZ polymer), poly(vinylbenzylchloride), poly(allylamine), polylysine, poly(4-vinylpyridine) quaternized with carboxypentyl groups, and poly(sodium 4-styrene sulfonate).

Enzymes covalently bound to the polymer in the active areas that are capable of promoting analyte detection are not believed to be particularly limited. Suitable enzymes may include those capable of detecting glucose, lactate, ketones, creatinine, or the like. Any of these analytes may be detected in combination with one another in analyte sensors capable of detecting multiple analytes. Suitable enzymes and enzyme systems for detecting these analytes are described hereinafter.

In some embodiments, the analyte sensors may comprise a glucose-responsive active area comprising a glucose-responsive enzyme disposed upon the sensor tail. Suitable glucose-responsive enzymes may include, for example, glucose oxidase or a glucose dehydrogenase (e.g., pyrroloquinoline quinone (PQQ) or a cofactor-dependent glucose dehydrogenase, such as flavine adenine dinucleotide (FAD)-dependent glucose dehydrogenase or nicotinamide adenine dinucleotide (NAD)-dependent glucose dehydrogenase). Glucose oxidase and glucose dehydrogenase are differentiated by their ability to utilize oxygen as an electron acceptor when oxidizing glucose; glucose oxidase may utilize oxygen as an electron acceptor, whereas glucose dehydrogenases transfer electrons to natural or artificial electron acceptors, such as an enzyme cofactor. Glucose oxidase or glucose dehydrogenase may be used to promote detection. Both glucose oxidase and glucose dehydrogenase may be covalently bonded to a polymer comprising the glucose-responsive active area and exchange electrons with an electron transfer agent (e.g., an osmium (Os) complex or similar transition metal complex), which may also be covalently bonded to the polymer. Suitable electron transfer agents are described in further detail below. Glucose oxidase may directly exchange electrons with the electron transfer agent, whereas glucose dehydrogenase may utilize a cofactor to promote electron exchange with the electron transfer agent. FAD cofactor may directly exchange electrons with the electron transfer agent. NAD cofactor, in contrast, may utilize diaphorase to facilitate electron transfer from the cofactor to the electron transfer agent. Further details concerning glucose-responsive active areas incorporating glucose oxidase or glucose dehydrogenase, as well as glucose detection therewith, may be found in commonly owned U.S. Pat. No. 8,268,143, for example.

In some embodiments, the active areas of the present disclosure may be configured for detecting ketones. Additional details concerning enzyme systems responsive to ketones may be found in commonly owned U.S. patent application Ser. No. 16/774,835 entitled "Analyte Sensors and Sensing Methods Featuring Dual Detection of Glucose and Ketones," filed on Jan. 28, 2020, and published as U.S. Patent Application Publication 2020/0237275, the contents of which is incorporated in its entirety herein. In such systems, β-hydroxybutyrate serves as a surrogate for ketones formed in vivo, which undergoes a reaction with an enzyme system comprising β-hydroxybutyrate dehydrogenase (HBDH) and diaphorase to facilitate ketones detection within a ketones-responsive active area disposed upon the surface of at least one working electrode, as described further herein. Within the ketones-responsive active area, β-hydroxybutyrate dehydrogenase may convert β-hydroxybutyrate and oxidized nicotinamide adenine dinucleotide ($NAD^+$) into acetoacetate and reduced nicotinamide adenine dinucleotide (NADH), respectively. It is to be understood that the term "nicotinamide adenine dinucleotide (NAD)" includes a phosphate-bound form of the foregoing enzyme cofactors. That is, use of the term "NAD" herein refers to both $NAD^+$ phosphate and NADH phosphate, specifically a diphosphate linking the two nucleotides, one containing an adenine nucleobase and the other containing a nicotinamide nucleobase. The $NAD^+$/NADH enzyme cofactor aids in promoting the concerted enzymatic reactions disclosed herein. Once formed, NADH may undergo oxidation under diaphorase mediation, with the electrons transferred during this process providing the basis for ketones detection at the working electrode. Thus, there is a 1:1 molar correspondence between the amount of electrons transferred to the working electrode and the amount of β-hydroxybutyrate converted. Transfer of the electrons to the working electrode may take place under further mediation of an electron transfer agent, such as an osmium (Os) compound or similar transition metal complex, as described in additional detail below. Albumin may further be present as a stabilizer within the active area. The β-hydroxybutyrate dehydrogenase and the diaphorase may be covalently bonded to a polymer comprising the ketones-responsive active area. The $NAD^+$ may or may not be covalently bonded to the polymer, but if the $NAD^+$ is not covalently bonded, it may be physically retained within the ketones-responsive active area, such as with a mass transport limiting membrane overcoating the ketones-responsive active area, wherein the mass transport limiting membrane is also permeable to ketones.

Other suitable chemistries for enzymatically detecting ketones may be utilized in accordance with the embodiments of the present disclosure. For example, β-hydroxybutyrate dehydrogenase (HBDH) may again convert β-hydroxybutyrate and $NAD^+$ into acetoacetate and NADH, respectively. Instead of electron transfer to the working electrode being completed by diaphorase and a suitable redox mediator, the reduced form of NADH oxidase (NADHOx (Red)) undergoes a reaction to form the corresponding oxidized form (NADHOx (Ox)). NADHOx (Red) may then reform through a reaction with molecular oxygen to produce superoxide, which may undergo subsequent conversion to hydrogen peroxide under superoxide dismutase (SOD) mediation. The hydrogen peroxide may then undergo oxidation at the working electrode to provide a signal that may be correlated to the amount of ketones that were initially present. The SOD may be covalently bonded to a polymer in the ketones-responsive active area, according to various embodiments. The β-hydroxybutyrate dehydrogenase and the NADH oxidase may be covalently bonded to a polymer in the ketones-responsive active area, and the $NAD^+$ may or may not be covalently bonded to a polymer in the ketones-responsive active area. If the $NAD^+$ is not covalently bonded, it may be physically retained within the ketones-responsive active area, with a membrane polymer promoting retention of the $NAD^+$ within the ketones-responsive active area. There is again a 1:1 molar correspondence between the amount of electrons transferred to the working electrode and the amount of β-hydroxybutyrate converted, thereby providing the basis for ketones detection.

Another enzymatic detection chemistry for ketones may utilize β-hydroxybutyrate dehydrogenase (HBDH) to convert β-hydroxybutyrate and $NAD^+$ into acetoacetate and NADH, respectively. The electron transfer cycle in this case is completed by oxidation of NADH by 1,10-phenanthroline-5,6-dione to reform $NAD^+$, wherein the 1,10-phenanthroline-5,6-dione subsequently transfers electrons to the working electrode. The 1,10-phenanthroline-5,6-dione may or may not be covalently bonded to a polymer within the ketones-responsive active area. The β-hydroxybutyrate dehydrogenase may be covalently bonded to a polymer in the ketones-responsive active area, and the $NAD^+$ may or may not be covalently bonded to a polymer in the ketones-responsive active area. Inclusion of an albumin in the active area may provide a surprising improvement in response stability. A suitable membrane polymer may promote retention of the $NAD^+$ within the ketones-responsive active area. There is again a 1:1 molar correspondence between the amount of electrons transferred to the working electrode and the amount of β-hydroxybutyrate converted, thereby providing the basis for ketones detection.

In some embodiments, the analyte sensors may further comprise a creatinine-responsive active area comprising an enzyme system that operates in concert to facilitate detection of creatinine. Creatinine may react reversibly and hydrolytically in the presence of creatinine amidohydrolase (CNH) to form creatine. Creatine, in turn, may undergo catalytic hydrolysis in the presence of creatine amidohydrolase (CRH) to form sarcosine. Neither of these reactions produces a flow of electrons (e.g., oxidation or reduction) to provide a basis for electrochemical detection of the creatinine. The sarcosine produced via hydrolysis of creatine may undergo oxidation in the presence of the oxidized form of sarcosine oxidase (SOX-ox) to form glycine and formaldehyde, thereby generating the reduced form of sarcosine oxidase (SOX-red) in the process. Hydrogen peroxide also may be generated in the presence of oxygen. The reduced form of sarcosine oxidase, in turn, may then undergo re-oxidation in the presence of the oxidized form of an electron transfer agent (e.g., an Os(III) complex), thereby producing the corresponding reduced form of the electron transfer agent (e.g., an Os(II) complex) and delivering a flow of electrons to the working electrode.

Oxygen may interfere with the concerted sequence of reactions used to detect creatinine in accordance with the disclosure above. Specifically, the reduced form of sarcosine oxidase may undergo a reaction with oxygen to reform the corresponding oxidized form of this enzyme but without exchanging electrons with the electron transfer agent.

Although the enzymes all remain active when the reaction with oxygen occurs, no electrons flow to the working electrode. Without being bound by theory or mechanism, the competing reaction with oxygen is believed to result from kinetic effects. That is, oxidation of the reduced form of sarcosine oxidase with oxygen is believed to occur faster than does oxidation promoted by the electron transfer agent. Hydrogen peroxide is also formed in the presence of the oxygen.

The desired reaction pathway for facilitating detection of creatinine may be encouraged by including an oxygen scavenger in proximity to the enzyme system. Various oxygen scavengers and dispositions thereof may be suitable, including oxidase enzymes such as glucose oxidase. Small molecule oxygen scavengers may also be suitable, but they may be fully consumed before the sensor lifetime is otherwise fully exhausted. Enzymes, in contrast, may undergo reversible oxidation and reduction, thereby affording a longer sensor lifetime. By discouraging oxidation of the reduced form of sarcosine oxidase with oxygen, the slower electron exchange reaction with the electron transfer agent may occur, thereby allowing production of a current at the working electrode. The magnitude of the current produced is proportional to the amount of creatinine that was initially reacted.

The oxygen scavenger used for encouraging the desired reaction may be an oxidase enzyme in any embodiment of the present disclosure. Any oxidase enzyme may be used to promote oxygen scavenging in proximity to the enzyme system, provided that a suitable substrate for the enzyme is also present, thereby providing a reagent for reacting with the oxygen in the presence of the oxidase enzyme. Oxidase enzymes that may be suitable for oxygen scavenging in the present disclosure include, but are not limited to, glucose oxidase, lactate oxidase, xanthine oxidase, and the like. Glucose oxidase may be a particularly desirable oxidase enzyme to promote oxygen scavenging due to the ready availability of glucose in various bodily fluids. Reaction 1 below shows the enzymatic reaction promoted by glucose oxidase to afford oxygen clearing.

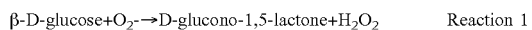

$$\beta\text{-D-glucose} + O_2 \rightarrow \text{D-glucono-1,5-lactone} + H_2O_2 \qquad \text{Reaction 1}$$

The concentration of available lactate in vivo is lower than that of glucose, but still sufficient to promote oxygen scavenging.

Oxidase enzymes, such as glucose oxidase, may be positioned in any location suitable to promote oxygen scavenging in the analyte sensors disclosed herein. Glucose oxidase, for example, may be positioned upon the sensor tail such that the glucose oxidase is functional and/or non-functional for promoting glucose detection. When non-functional for promoting glucose detection, the glucose oxidase may be positioned upon the sensor tail such that electrons produced during glucose oxidation are precluded from reaching the working electrode, such as through electrically isolating the glucose oxidase from the working electrode.

Additional details concerning enzyme systems responsive to creatinine may be found in commonly owned U.S. patent application Ser. No. 16/774,835 entitled "Analyte Sensors and Sensing Methods for Detecting Creatinine," filed on Sep. 25, 2019, and published as U.S. Patent Application Publication 2020/0237275, which is incorporated herein by reference in its entirety.

In some embodiments, the analyte sensors may comprise a lactate-responsive active area comprising a lactate-responsive enzyme disposed upon the sensor tail. Suitable lactate-responsive enzymes may include, for example, lactate oxidase. Lactate oxidase or other lactate-responsive enzymes may be covalently bonded to a polymer comprising the lactate-responsive active area and exchange electrons with an electron transfer agent (e.g., an osmium (Os)) complex or similar transition metal complex), which may also be covalently bonded to the polymer. Suitable electron transfer agents are described in further detail below. An albumin, such as human serum albumin, may be present in the lactate-responsive active area to stabilize the sensor response, as described in further detail in commonly owned U.S. Patent Application Publication 20190320947, which is incorporated herein by reference in its entirety. Lactate levels may vary in response to numerous environmental or physiological factors including, for example, eating, stress, exercise, sepsis or septic shock, infection, hypoxia, presence of cancerous tissue, or the like.

In some embodiments, the analyte sensors may comprise an active area responsive to pH. Suitable analyte sensors configured for determining pH are described in commonly owned U.S. Patent Application Publication 20200060592, which is incorporated herein by reference. Such analyte sensors may comprise a sensor tail comprising a first working electrode and a second working electrode, wherein a first active area located upon the first working electrode comprises a substance having pH-dependent oxidation-reduction chemistry, and a second active area located upon the second working electrode comprises a substance having oxidation-reduction chemistry that is substantially invariant with pH. By obtaining a difference between the first signal and the second signal, the difference may be correlated to the pH of a fluid to which the analyte sensor is exposed.

Two different types of active areas may be located upon a single working electrode, such as the carbon working electrodes discussed above, and spaced apart from one another. Each active area may have an oxidation-reduction potential, wherein the oxidation-reduction potential of the first active area is sufficiently separated from the oxidation-reduction potential of the second active area to allow independent production of a signal from one of the active areas. By way of non-limiting example, the oxidation-reduction potentials may differ by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction may take place within one of the two active areas (i.e., within the first active area or the second active area) without substantially inducing an electrochemical reaction within the other active area. Thus, a signal from one of the first active area or the second active area may be independently produced at or above its corresponding oxidation-reduction potential (the lower oxidation-reduction potential) but below the oxidation-reduction potential of the other active area. A different signal may allow the signal contribution from each analyte to be resolved.

Some or all embodiments of analyte sensors disclosed herein may feature one or more active areas located upon the surface of at least one working electrode, where the active areas detect the same or different analytes. A membrane may overcoat at least the active area (comprising an analyte-responsive enzyme), and may further overcoat all or a portion of the working electrode lacking an active area (the exposed or extraneous portion of the working electrode). The membrane may be a mass transport limiting membrane and may be a single layer of membrane, a bilayer of two different membrane polymers, or an admixture of two different membrane polymers An electron transfer agent may be present in any of the active areas disclosed herein. Suitable electron transfer agents may facilitate conveyance of electrons to the adjacent working electrode after one or more analytes undergoes an enzymatic oxidation-reduction reaction within the corresponding active area, thereby generating an electron flow that is indicative of the presence of a particular analyte. The amount of current generated is proportional to the quantity of analyte that is present. Depending on the sensor configuration used, the electron transfer agents in active areas responsive to different analytes may be the same or different. For example, when two different active areas are disposed upon the same working electrode, the electron transfer agent within each active area may be different (e.g., chemically different such that the electron transfer agents exhibit different oxidation-reduction potentials). When multiple working electrodes are present, the electron transfer agent within each active area may be the same or different, since each working electrode may be interrogated separately.

Suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605, 200, which are incorporated herein by reference in their entirety. Additional examples of suitable electron transfer agents include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

Active areas suitable for detecting any of the analytes disclosed herein may comprise a polymer to which the electron transfer agents are covalently bound. Any of the electron transfer agents disclosed herein may comprise suitable functionality to promote covalent bonding to the polymer within the active areas. Suitable examples of polymer-bound electron transfer agents may include those described in U.S. Pat. Nos. 8,444,834, 8,268,143 and 6,605, 201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. When two or more different active areas are present, the polymer within each active area may be the same or different.

Covalent bonding of the electron transfer agent to a polymer within an active area may take place by polymerizing a monomer unit bearing a covalently bonded electron transfer agent, or the electron transfer agent may be reacted with the polymer separately after the polymer has already been synthesized. A bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, one or more of the enzymes within the active areas may be covalently bonded to a polymer comprising an active area. When an enzyme system comprising multiple enzymes is present in a given active area, all of the multiple enzymes may be covalently bonded to the polymer in some embodiments, and in other embodiments, only a portion of the multiple enzymes may be covalently bonded to the polymer. For example, one or more enzymes comprising an enzyme system may be covalently bonded to the polymer and at least one enzyme may be non-covalently associated with the polymer, such that the non-covalently bonded enzyme is physically entrained within the polymer. Covalent bonding of the enzyme(s) to the polymer in a given active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidyl ether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments. In particular embodiments, all of the enzymes within a given active area may be covalently bonded to a polymer.

The electron transfer agent and/or the enzyme(s) may be associated with the polymer in an active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained within the polymer without being bonded thereto. Physically entrained electron transfer agents and/or enzyme(s) may still suitably interact with a fluid to promote analyte detection without being substantially leached from the active areas.

The polymer within the active area may be chosen such that outward diffusion of $NAD^+$ or another cofactor not covalently bound to the polymer is limited. Limited outward diffusion of the cofactor may promote a reasonable sensor lifetime (days to weeks) while still allowing sufficient inward analyte diffusion to promote detection.

In some embodiments, a stabilizer may be incorporated into the active area of the analyte sensors described herein to improve the functionality of the sensors and achieve desired sensitivity and stability. Such stabilizers may include an antioxidant and/or companion protein to stabilize the enzyme, for instance. Examples of suitable stabilizers may include, but are not limited to serum albumin (e.g., humane or bovine serum albumin or other compatible albumin), catalase, other enzyme antioxidants, and the like, and any combination thereof. The stabilizers may be conjugated or non-conjugated.

In particular embodiments of the present disclosure, the mass transport limiting membrane overcoating one or more active areas may comprise a crosslinked polyvinylpyridine homopolymer or copolymer. The composition of the mass transport limiting membrane may be the same or different where the mass transport limiting membrane overcoats active areas of differing types. When the membrane composition varies at two different locations, the membrane may comprise a bilayer membrane or a homogeneous admixture of two different membrane polymers, one of which may be a crosslinked polyvinylpyridine or polyvinylimidazole homopolymer or copolymer. Suitable techniques for depositing a mass transport limiting membrane upon the active area may include, for example, spray coating, painting, inkjet printing, screen printing, stenciling, roller coating, dip coating, the like, and any combination thereof. Dip coating techniques may be especially desirable for polyvinylpyridine and polyvinylimidazole polymers and copolymers.

In certain embodiments, the mass transport limiting membrane discussed above is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

In some embodiments, a membrane may be formed by crosslinking in situ a polymer, including those discussed above, modified with a zwitterionic moiety, a non-pyridine copolymer component, and optionally another moiety that is either hydrophilic or hydrophobic, and/or has other desirable properties, in a buffer solution (e.g., an alcohol-buffer solution). The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, and the like, and any combinations thereof, may be used to enhance the biocompatibility of the polymer or the resulting membrane.

In some embodiments, the membrane may comprise a compound including, but not limited to, poly(styrene-co-maleic anhydride), dodecylamine and poly(propylene glycol)-block-poly(ethylene glycol)-block-poly(propylene glycol) (2-aminopropyl ether) crosslinked with poly(propylene glycol)-block-poly(ethylene glycol)-block-poly(propylene glycol) bis(2-aminopropyl ether); poly(N-isopropyl acrylamide); a copolymer of poly(ethylene oxide) and poly (propylene oxide); polyvinylpyridine; a derivative of polyvinylpyridine; polyvinylimidazole; a derivative of polyvinylimidazole; polyvinylpyrrolidone (PVP), and the like; and any combination thereof. In some embodiments, the membrane may be comprised of a polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group. Other membrane compounds, alone or in combination with any aforementioned membrane compounds, may comprise a suitable copolymer of 4-vinylpyridine and styrene and an amine-free polyether arm.

The membrane compounds described herein may further be crosslinked with one or more crosslinking agents, including those listed above with reference to the enzyme described herein. For example, suitable crosslinking agents may include, but are not limited to, polyethylene glycol diglycidylether (PEGDGE), glycerol triglycidyl ether (Gly3), polydimethylsiloxane diglycidylether (PDMS-DGE), or other polyepoxides, cyanuric chloride, N-hydroxysuccinimide, imidoesters, epichlorohydrin, or derivatized variants thereof, and any combination thereof. Branched versions with similar terminal chemistry are also suitable for the present disclosure. For example, in some embodiments, the crosslinking agent can be triglycidyl glycerol ether and/or PEDGE and/or polydimethylsiloxane diglycidylether (PDMS-DGE).

A membrane may be formed in situ by applying an alcohol-buffer solution of a crosslinker and a modified polymer over the active area and any additional compounds included in the active area (e.g., electron transfer agent) and allowing the solution to cure for about one to two days or other appropriate time period. The crosslinker-polymer solution may be applied over the active area by placing a droplet or droplets of the membrane solution on at least the sensor element(s) of the sensor tail, by dipping the sensor tail into the membrane solution, by spraying the membrane solution on the sensor, by heat pressing or melting the membrane in any sized layer (such as discrete or all encompassing) and either before or after singulation, vapor deposition of the membrane, powder coating of the membrane, and the like, and any combination thereof. In order to coat the distal and side edges of the sensor, the membrane material may be applied subsequent to application (e.g., singulation) of the sensor electronic precursors (e.g., electrodes). In some embodiments, the analyte sensor is dip-coated following electronic precursor application to apply one or more membranes. Alternatively, the analyte sensor could be slot-die coated wherein each side of the analyte sensor is coated separately. A membrane applied in the above manner may have any of various functions including, but not limited to, mass transport limitation (i.e., reduction or elimination of the flux of one or more analytes and/or compounds that reach the active area), biocompatibility enhancement, interferent reduction, and the like, and any combination thereof.

Generally, the thickness of the membrane is controlled by the concentration of the membrane solution, by the number of droplets of the membrane solution applied, by the number of times the sensor is dipped in the membrane solution, by the volume of membrane solution sprayed on the sensor, and the like, and by any combination of these factors. In some embodiments, the membrane described herein may have a thickness ranging from about 0.1 micrometers ($\mu$m) to about 1000 $\mu$m, encompassing any value and subset therebetween. As stated above, the membrane may overlay one or more active areas, and in some embodiments, the active areas may have a thickness of from about 0.1 $\mu$m to about 50 $\mu$m, encompassing any value and subset therebetween. In some embodiments, a series of droplets may be applied atop one another to achieve the desired thickness of the active area and/or membrane, without substantially increasing the diameter of the applied droplets (i.e., maintaining the desired diameter or range thereof). Each single droplet, for example, may be applied and then allowed to cool or dry, followed by one or more additional droplets. Active areas and membrane may, but need not be, the same thickness throughout or composition throughout.

In some embodiments, the membrane composition for use as a mass transport limiting layer of the present disclosure may comprise polydimethylsiloxane (PDMS), polydimethylsiloxane diglycidylether (PDMS-DGE), aminopropyl terminated polydimethylsiloxane, and the like, and any combination thereof for use as a leveling agent (e.g., for reducing the contact angle of the membrane composition or active area composition). Branched versions with similar terminal chemistry are also suitable for the present disclosure. Certain leveling agents may additionally be included, such as those found, for example, in U.S. Pat. No. 8,983,568, the disclosure of which is incorporated by reference herein in its entirety.

In some instances, the membrane may form one or more bonds with the active area. As used herein, the term "bonds," and grammatical variants thereof, refers to any type of an interaction between atoms or molecules that allows chemical compounds to form associations with each other, such as, but not limited to, covalent bonds, ionic bonds, dipole-dipole interactions, hydrogen bonds, London dispersion forces, and the like, and any combination thereof. For example, in situ polymerization of the membrane can form crosslinks between the polymers of the membrane and the polymers in the active area. In some embodiments, crosslinking of the membrane to the active area facilitates a reduction in the occurrence of delamination of the membrane from the sensor.

Embodiments disclosed herein include:

Analyte sensor comprises an electrode layer having an elongate body comprising a proximal end and a distal end. The electrode layer includes a first active working electrode area, a second electrode portion, and at least one gap electrically separating the first active working electrode portion and the second electrode portion. The first active working electrode area comprises at least one sensing spot with at least one analyte responsive enzyme disposed thereupon. Additional analyte sensors disclosed.

Aspects of the invention are set out in independent claims 1, 15 and 31 and preferred and optional features are set out in the claims dependent thereon. The preferred and optional features may be provided in combination within a single analyte sensor. Moreover, an analyte sensor may be provided that combines features of independent claims 1, 15 and 31 together with any of the features of the dependent claims.

A. A method comprising: laser singulating a working electrode, the working electrode comprising an active area disposed thereupon and electrode asperities, the active area comprising an analyte-responsive enzyme; and laser planing at least a portion of the electrode asperities, the laser planing recessed from an edge of the working electrode to remove at least a portion of the electrode asperities.

B. A working electrode as part of an amperometric sensor, the working electrode comprising a working electrode comprising active area disposed thereupon and electrode asperities, the active area comprising an analyte-responsive enzyme, wherein the working electrode is first laser singulated and thereafter laser planed to and the working electrode thereafter laser planed from an edge of the working electrode to remove at least a portion of electrode asperities therefrom.

C. A method comprising: laser singulating a working electrode, the working electrode comprising an active area disposed thereupon and electrode asperities, the active area comprising an analyte-responsive enzyme; disposing a membrane upon at least a portion of the working electrode comprising the active area; and laser planing at least a portion of the electrode asperities, the laser planing recessed from an edge of the working electrode to remove at least a portion of the electrode asperities.

D. An analyte sensor comprising: a working electrode comprising an active area disposed thereon and electrode asperities laser planed therefrom, the active area comprising an analyte-responsive enzyme.

E. A method comprising: exposing an analyte sensor to a bodily fluid, the analyte sensor comprising a working electrode comprising an active area disposed thereon and electrode asperities laser planed therefrom, the active area comprising an analyte-responsive enzyme.

F. An analyte sensor comprising: a working electrode comprising an active area having an analyte-responsive enzyme disposed thereon; a membrane disposed upon at least a portion of the working electrode comprising the active area; and an interferent-reactant species incorporated into the analyte sensor.

G. A method comprising: exposing an analyte sensor to a bodily fluid, the analyte sensor comprising a working electrode comprising an active area having an analyte-responsive enzyme disposed thereon; a membrane disposed upon at least a portion of the working electrode comprising the active area; and an interferent-reactant species incorporated into the analyte sensor.

H. An analyte sensor comprising: a working electrode comprising an active area having an analyte-responsive enzyme disposed thereon; and a scrubbing electrode positioned in a facing relationship to the working electrode, wherein the working electrode and scrubbing electrode are spatially offset.

I. A method comprising: exposing an analyte sensor to a bodily fluid, the analyte sensor comprising a working electrode comprising an active area having an analyte-responsive enzyme disposed thereon; and a scrubbing electrode positioned in a facing relationship to the working electrode, wherein the working electrode and scrubbing electrode are spatially offset.

J. An analyte sensor comprising: a working electrode comprising an active area having an analyte-responsive enzyme disposed thereon; and a permeable scrubbing electrode positioned above the working electrode, wherein the permeable scrubbing electrode is permeable to an analyte of interest for diffusion of the analyte of interest to the analyte-responsive enzyme.

K. A method comprising: exposing an analyte sensor to a bodily fluid, the analyte sensor comprising a working electrode comprising an active area having an analyte-responsive enzyme disposed thereon; and a permeable scrubbing electrode positioned above the working electrode, wherein the permeable scrubbing electrode is permeable to an analyte of interest for diffusion of the analyte of interest to the analyte-responsive enzyme.

L. An analyte sensor comprising: a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1.

M. A method comprising: exposing an analyte sensor to a bodily fluid, the analyte sensor comprising a working electrode having sensing portion and an exposed electrode portion, wherein the sensing portion comprises an active area having an analyte-responsive enzyme disposed thereupon and the exposed electrode portion comprises no active area, and wherein a ratio of the exposed electrode portion to the sensing portion is in the range of about 1:10 to about 10:1.

Each of embodiments L and M may have one or more of the following additional elements in any combination:

Element 1: wherein the working electrode is a carbon working electrode.

Element 2: wherein an area of the exposed electrode portion is in the range of about 0.1 mm2 to about 2 mm2.

Element 3: wherein an area of the sensing portion is in the range of about 0.01 mm2 to about 1.8 mm2.

Element 4: wherein the active area is comprised of a plurality of discontiguous active areas.

Element 5: wherein the active area is comprised of a plurality of discontiguous active areas, and wherein each discontiguous active area has a diameter in the range of about 0.01 μm to about 1.8 μm.

Element 6: wherein the active area is comprised of a plurality of discontiguous active areas separated by a pitch having a distance in the range of about 50 μm to about 500 μm.

Element 7: wherein the sensing portion is comprised of a plurality of discontiguous active areas arranged in a 1×n grid configuration, wherein n is an integer in the range of 2 to about 20.

Element 8: wherein the sensing portion is comprised of a plurality of discontiguous active areas arranged in a 2×n grid configuration, wherein n is an integer in the range of 3 to about 10.

Element 9: wherein the sensing portion is comprised of a plurality of discontiguous active areas arranged in a 3×n grid configuration, wherein n is an integer in the range of 2 to about 6.

Element 10: wherein a mass transport limiting membrane is disposed upon at least the sensing portion.

Element 11: wherein the analyte-responsive enzyme is a glucose responsive enzyme.

To facilitate a better understanding of the embodiments described herein, the following examples of various representative embodiments are given. In no way should the following examples be read to limit, or to define, the scope of the invention.

Figure 13A:
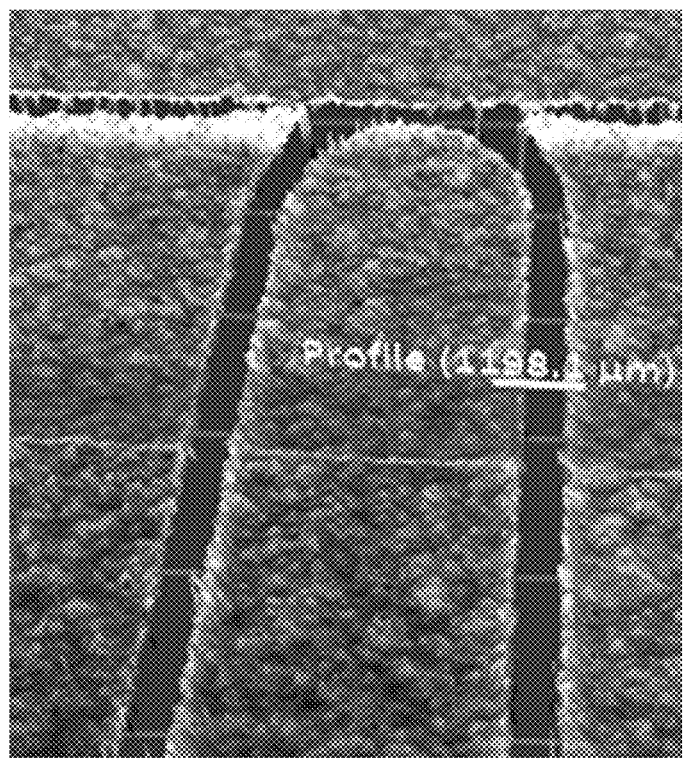
FIG. 13A shows a photograph of a top view of a working electrode having no membrane and no active area disposed thereon.
Figure 13B:
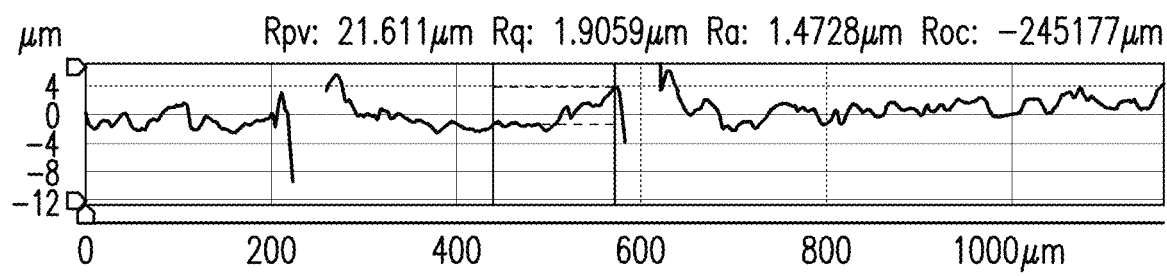
FIG. 13B is a depth profile along the line indicated in FIG. 13A.

Example 1. In this Example, laser planing was performed on the example laser singulated working electrode shown in FIG. 13A. FIG. 13A does not comprise an active area disposed thereupon. FIG. 13B shows a 3D optical profile of a portion of singulated working electrode of FIG. 13A, evaluated along the identified profile width. The 3D optical profile was obtained using a ZEGAGE™ 3D Optical Profiler, ZYGOO® Corporation (Middlefield, CT). As shown in FIG. 13B, the electrode asperities at the edge of the singulated sensor tail exhibited a height of about 5 μm.

Figure 13C:
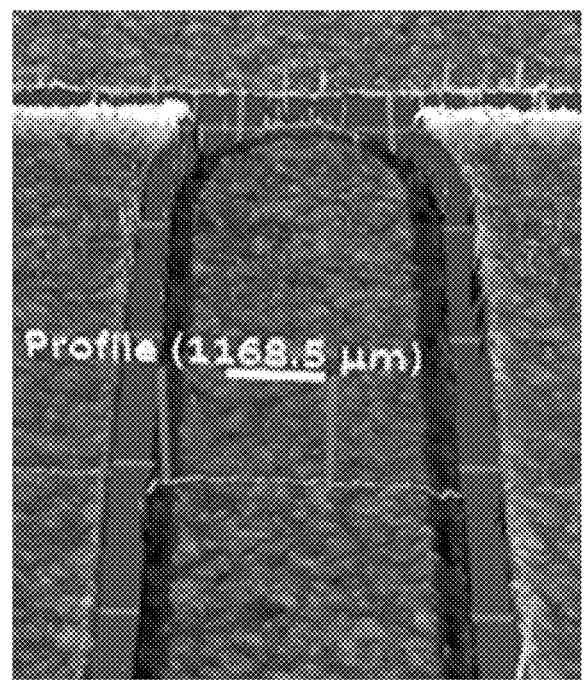
FIG. 13C shows a photograph of a top view of the working electrode of FIG. 13A after laser planing, in accordance with one or more aspects of the present disclosure.
Figure 13D:
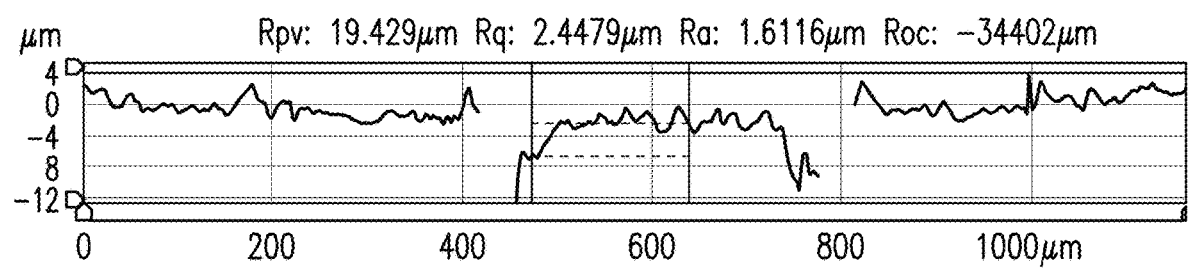
FIG. 13D is a depth profile along the line indicated in FIG. 13C.

Laser planing was performed using three single-pass laser lines positioned at the edge of the carbon asperities and made 10 μm apart progressively toward the midline of the electrode at 10% laser power. In the examples described herein, a UV laser was used, but it is to be appreciated that any laser may be used to perform laser planing, without departing from the scope of the present disclosure. FIG. 13C is a photograph of the planed sensor tail, showing the beveled edge of the working electrode of the sensor tail. FIG. 13D is a 3D optical profile (obtained as previously described) along the identified profile line showing the electrode asperities removed.

Figure 14A:
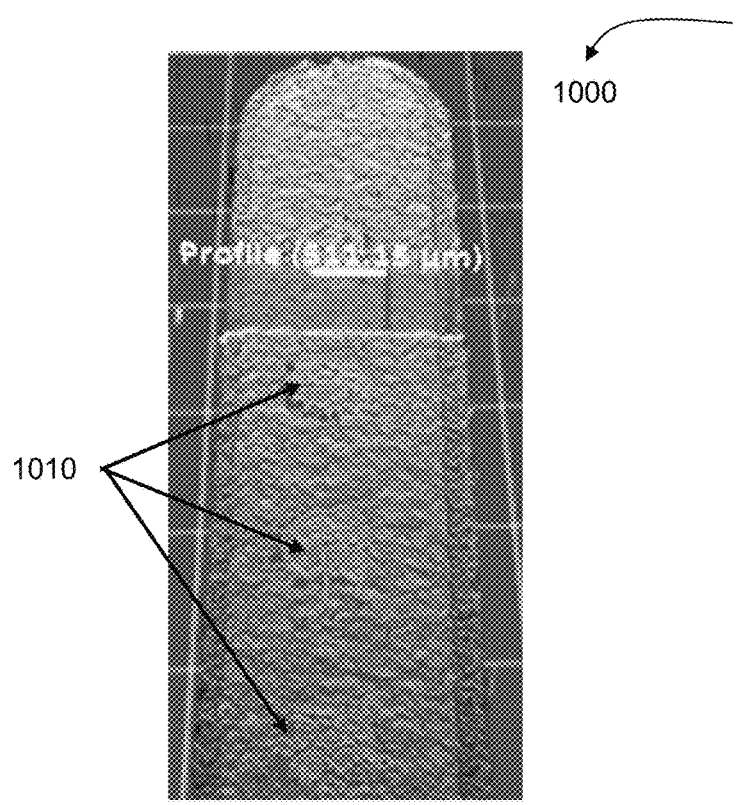
FIG. 14A shows a photograph of a top view of a working electrode having no membrane and an active area disposed thereon after laser planing, in accordance with one or more aspects of the present disclosure.
Figure 14B:
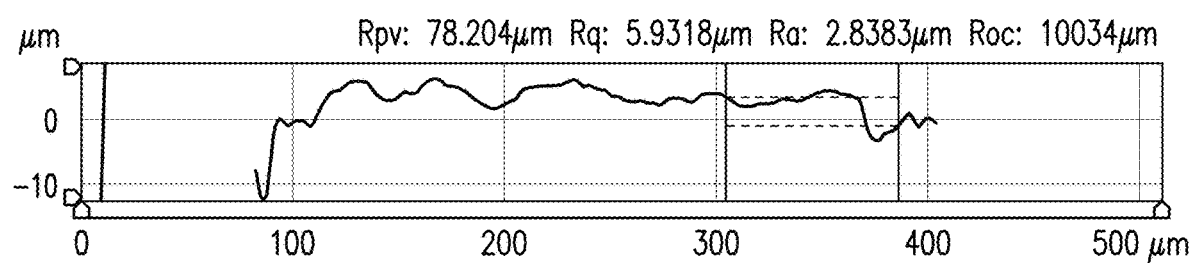
FIG. 14B is a depth profile along the line indicated in FIG. 14A.
Figure 15:
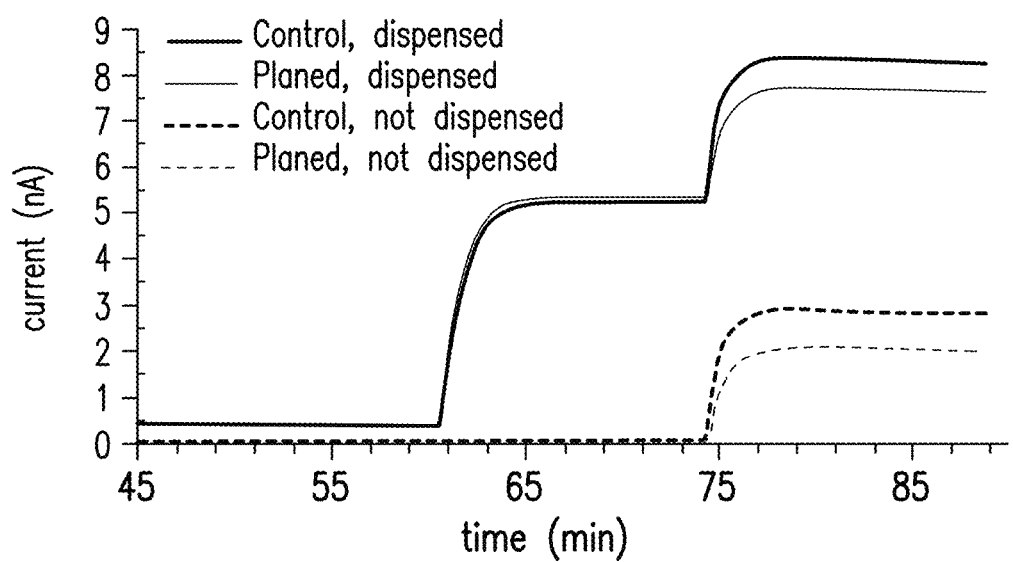
FIG. 15 is a graph of a paired-difference test comparing planed and unplanned working electrodes having either an active area or lacking an active area in response to the interferent ascorbic acid.

Example 2. In this Example, and with reference to FIG. 14A, a laser planed carbon working electrode 1000 was prepared in accordance with Example 1, the carbon electrode comprising active areas 1010 dispensed thereupon. The unplaned carbon electrode comprising active areas 1010 is not shown, but will be referred to as "unplaned, dispensed" electrode. FIG. 14B is a 3D optical profile (obtained as previously described) along the identified profile line showing minimal electrode asperities as a result of the planing.

Example 3. A paired-difference test was performed. The unplaned electrode of FIG. 13A and planed electrode of FIG. 13C having no active area ("not planed, not dispensed" and "planed, not dispensed," respectively) were examined with the "unplaned, dispensed" electrode of Example 2 and the planed electrode of FIG. 14A having multiple sensing spots ("planed, dispensed") were evaluated in 100 mM PBS at 37° C. separately in 50 mg/dL glucose and 2 mg/dL ascorbate. The results are provided in Table 1 below, and graphically represented in FIG. 15.

TABLE 1

| | Iavg (nA) n = 8* | | | |
|---|---|---|---|---|
| | Undispensed | | Dispensed | |
| | Not Planed (FIG. 13A) | Planed (FIG. 13C) | Not Planed | Planed (FIG. 14A) |
| Glucose | −0.01 | −0.01 | 4.86 | 4.96 |
| Ascorbate | 2.88 | 2.06 | 3.11 | 2.37 |
| % Δ** | | −28.5 | | −23.8 |

*background corrected;
**laser-planed relative to control

As shown, the paired-different test demonstrates that the laser planed electrodes demonstrate a reduction in 2 mg/dL of ascorbate by about 24% to about 29% compared to the unplaned counterparts.

Example 4. Paired-Difference tests were performed on the following prepared laser singulated working electrodes. The unplaned "control" working electrodes comprised active areas of multiple sensing spots. The electrodes described as "compressed" comprise the same concentration of active area, but the multiple sensing spots are closer together and/or closer to the tip of the electrode. The totality of analyte-responsive enzyme for all samples was the same, whether compressed or not. Laser planing is described with reference to three separate single-pass laser lines, each a particular distance from the edge of the initial unplaned electrode (the "planing scheme"). For example, "20-40-60" refers to a first single-pass laser line at 20 μm from the edge of the unplaned electrode, a second single-pass laser line at 40 μm from the edge of the unplaned electrode, and a third single-pass laser line at 60 μm from the edge of the unplaned electrode.

TABLE 2

Figures 16A, 16B, 16C, 16D, 16E:
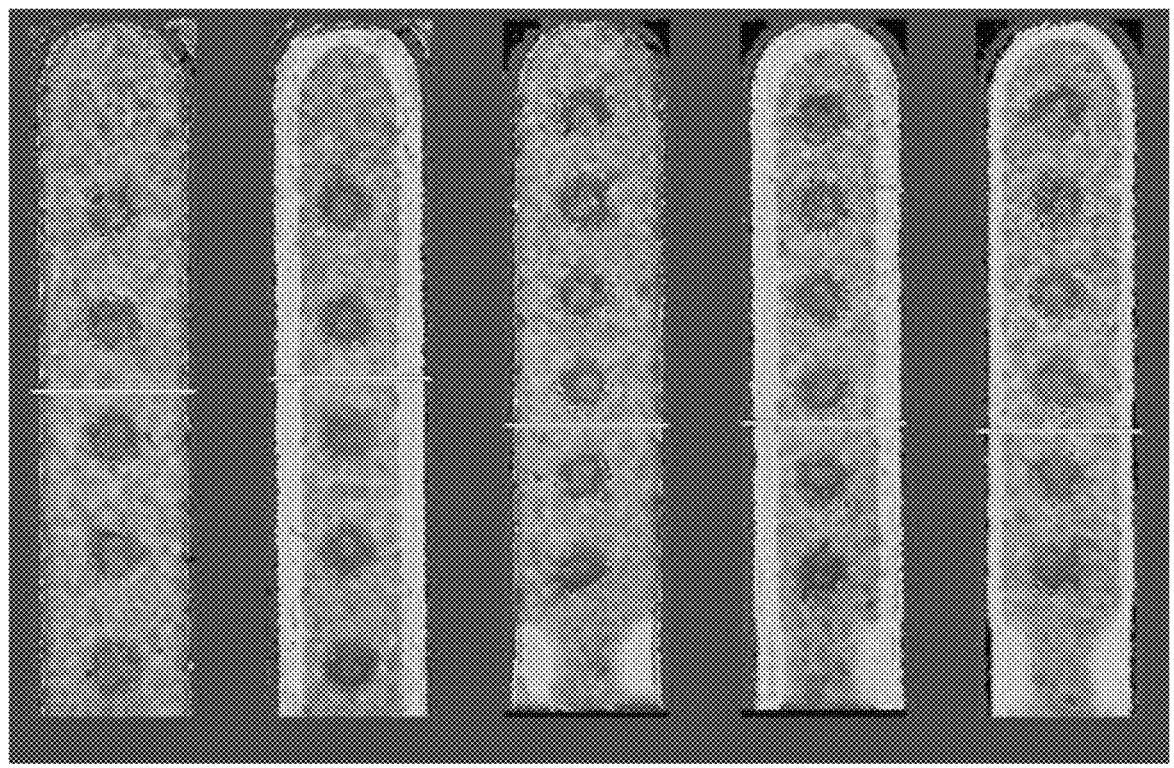
FIGS. 16A-16E show photographs of working electrodes.

| | FIG. 16A | FIG. 16B | FIG. 16C | FIG. 16D | FIG. 16E |
|---|---|---|---|---|---|
| Compressed? | No | No | Yes | Yes | Yes |
| Planing Scheme | Unplaned | 20-40-60 | Unplaned | 20-40-60 | 15-25-40 |

The electrodes 16A-16E described in Table 2 in some instances were coated with a mass transport limiting membrane having the thickness shown in Table 3 below. Paired-difference tests (avg. of n=6/condition) was performed in 100 mM PBS at 37° C. separately in 50 mg/dL glucose and 2 mg/dL ascorbate. The results are provided in Table 3 below.

TABLE 3

| | Planing? | Membrane Thickness | % Δ |
|---|---|---|---|
| 16A | No | 36 gm | 0 |
| 16A | No | 51 gm | −20 |
| 16B | 20-40-60 | 35 gm | −30 |
| 16B | 20-40-60 | 51 gm | −44 |
| 16C | No | 36 gm | −30 |
| 16C | No | 51 gm | −49 |
| 16D | 20-40-60 | 37 gm | −52 |
| 16D | 20-40-60 | 50 gm | −65 |
| 16E | 15-25-40 | 35 gm | −50 |
| 16E | 15-25-40 | 52 gm | −62 |

As shown in Table 3, the paired-different test demonstrates that the laser planed electrodes demonstrate a reduction in 2 mg/dL of ascorbate by about 30% to about 65% compared to the unplaned counterparts. The difference between the 40 μm planed distance toward the electrode midline v. the 60 μm distance did not appear to make an appreciable difference in resistance to interferent signal, indicating that a relatively small laser planing amount can be effective.

Figure 17:
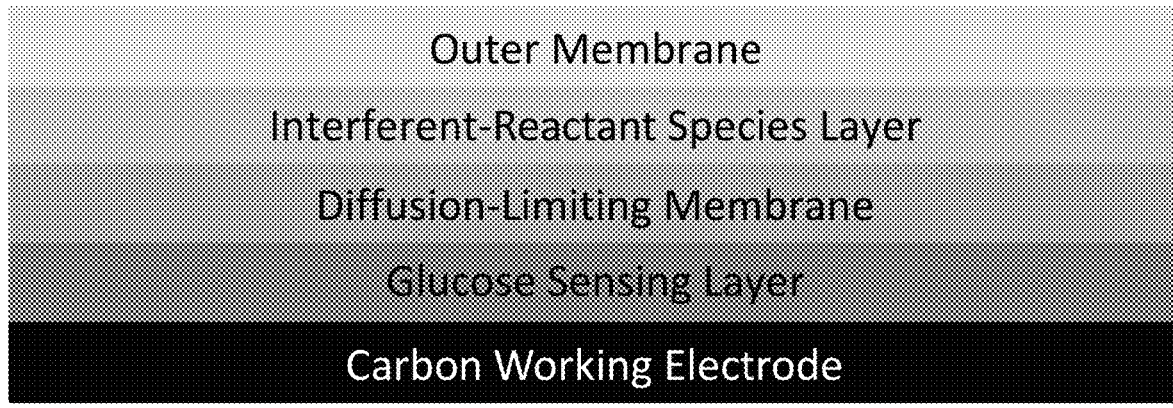
FIG. 17 is a sensor configuration for inclusion of an interferent-reactant species layer, according to one or more embodiments of the present disclosure.

Example 5. In this example, the effectiveness of incorporating an enzymatic interferent-reactant species into an analyte sensor for eliminating or reducing interferent signal at the working electrode was evaluated. Glucose sensors having an interferent-reactant layer for reacting with ascorbic acid were prepared, as shown in FIG. 17. A glucose active area sensing layer was coated onto the carbon working electrode in the form of six discontiguous sensing spots and comprising glucose oxidase sensing chemistry. A diffusion-limiting membrane was coated upon the entire working electrode, covering each of the sensing spots, and comprised a crosslinked polyvinylpyridine co-styrene polymer (termed "10Q5"). 50 nL of an interferent-reactant species layer was coated atop the diffusion-limiting membrane, covering the sensing layer and the excess (exposed) carbon working electrode. The interferent-reactant species layer comprised ascorbate oxidase (24.6 mg/ml) in a matrix of PVI polymer (9.2 mg/ml), PEDGE-400 crosslinker (6.2 mg/ml), and albumin stabilizer (24.6 mg/ml) (Solutions were made in 10 mM IVIES buffer, pH 5.5). Two types of ascorbate oxidase were evaluated, ASO-301 and ASO-311, each available from TOYOBO, headquartered in Osaka, Japan. A thin outer layer of membrane comprised of PVP crosslinked with PEGDGE400 was coated atop the entirety of the interferent-reactant species layer. These sensors are referred to as "GOx/10Q5+AscOx301/PVP" and "GOx/10Q5+AscOx311/PVP," depending on the ascorbate oxidase used.

Figure 18:
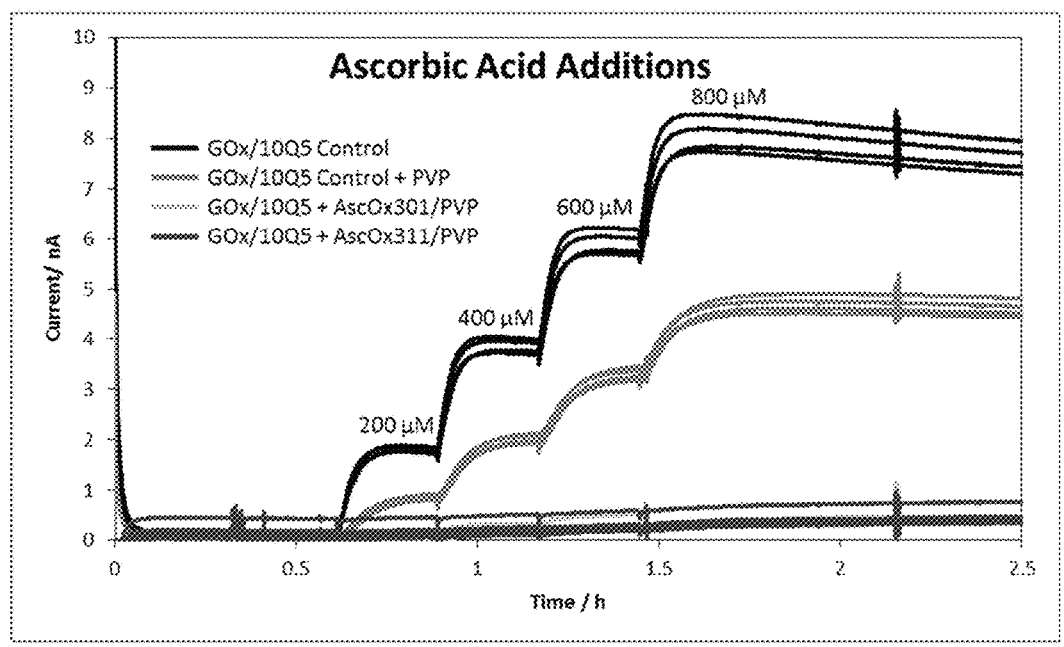
FIG. 18 is an ascorbic acid calibration curve for analyte sensors of FIG. 17 comprising an interferent-reactant species layer, according to one or more aspects of the present disclosure.
Figure 19:
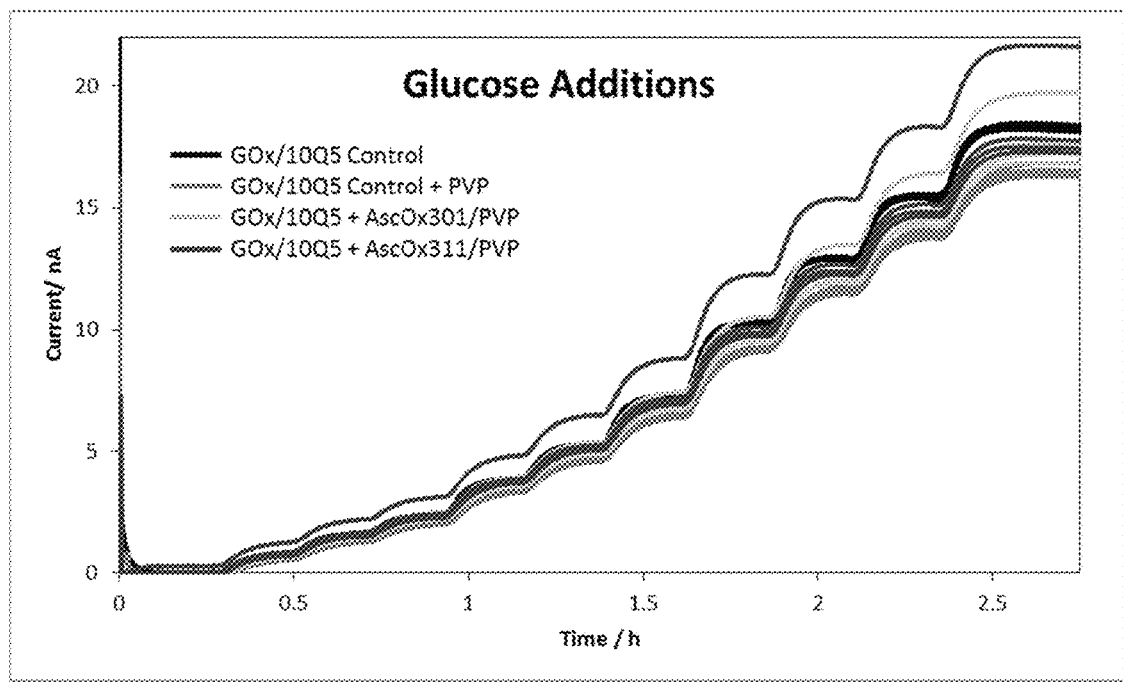
FIG. 19 is a glucose calibration curve for analyte sensors of FIG. 17 comprising an interferent-reactant species layer, according to one or more aspects of the present disclosure.

The sensors were tested in 100 mM PBS at a temperature of 33° C., a pH of 7.4, and a working potential of +40 mV, along with two controls, in quadruplicate, separately in ascorbic acid and glucose. The first control ("Gox/10Q5 Control") comprised the carbon working electrode, sensing spots, and sensing membrane as described above (absent the interferent-reactant species layer, and the outer layer). The second control ("Gox/10Q5+PVP Control") comprised the carbon working electrode, sensing spots, sensing membrane, and the outer layer coated thereupon. The sensors were calibrated in ascorbic acid, as shown in FIG. 18, and in 30 mM glucose, as shown in FIG. 19.

Figure 20:
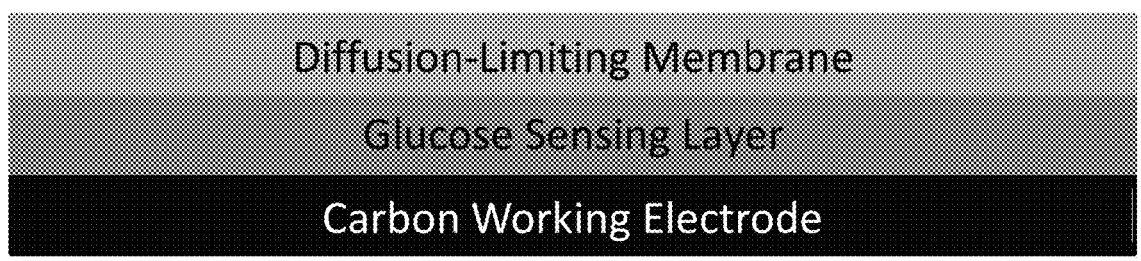
FIG. 20 is a sensor configuration for inclusion of an interferent-reactant species layer, according to one or more aspects of the present disclosure.
Figure 21:
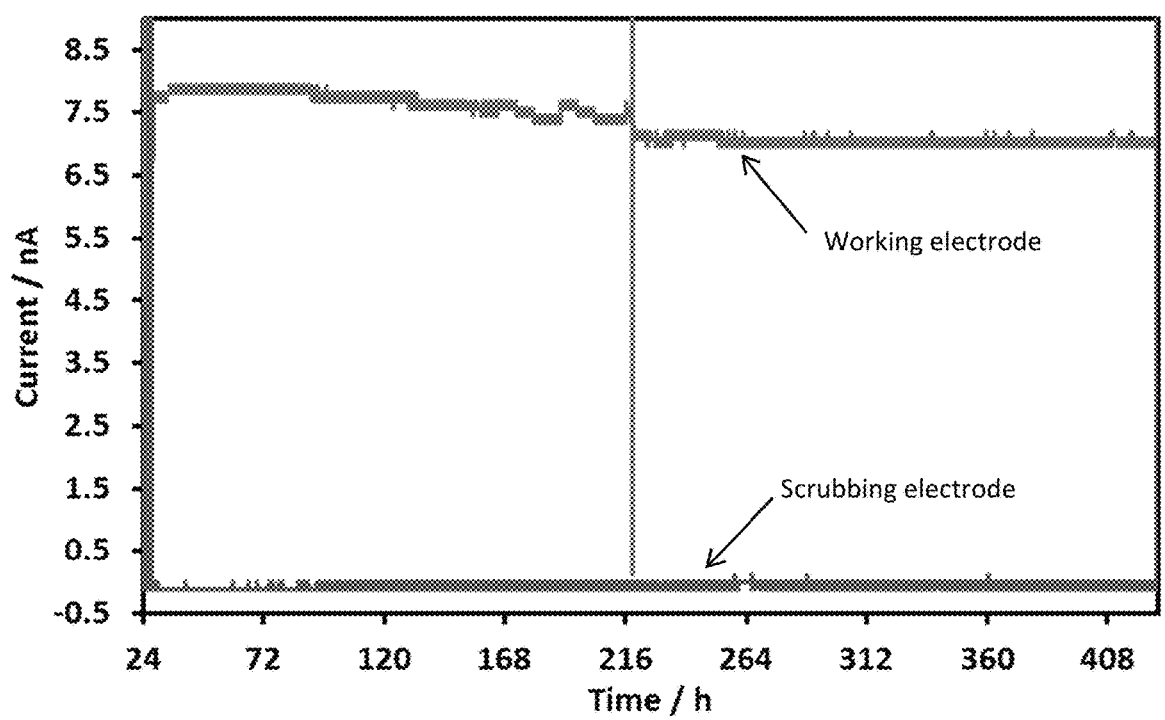
FIGS. 21-24 are sensor current traces of sensors comprising scrubbing electrodes, in accordance with one or more aspects of the present disclosure.

As shown in FIG. 20, the sensors with the interferent-reactant layer (comprising ascorbate oxidase) show very minimal response to ascorbic acid additions, as compared to the control sensors both with and without the PVP membrane. Further, the inclusion of the interferent-reactant layer did not have an appreciable influence on the response to glucose, as compared to the control sensors both with and without the PVP membrane. Moreover, even if the interferent-reactant layer had affected the glucose sensing, as long as linearity and stability for glucose is retained, any such affect could be easily accounted for. Accordingly, incorporation of an enzymatic interferent-reactant species layer is a viable method to eliminate or reduce signal at the working electrode attributable to interferents.

Example 6. In this example, the effectiveness of incorporating a metal oxide interferent-reactant species into an analyte sensor for eliminating or reducing interferent signal at the working electrode was evaluated. Glucose sensors having an interferent-reactant layer for reacting with ascorbic acid were prepared, as shown in FIG. 20. A glucose active area sensing layer was coated onto the carbon working electrode disposed upon a substrate. The active area sensing layer was in the form of six discontiguous sensing spots comprising glucose oxidase sensing chemistry. The active area had a total area of 0.1 mm$^2$. The working electrodes comprising the sensing spots were dipped in a diffusion-limiting membrane comprising either a control composition or an experimental composition. The control diffusion-limiting membrane comprised 4 ml of 140 mg/ml of 10Q5, 0.4 ml of 100 mg/ml of gly3 in solvent consisting of 80% ethanol and 20% 10 mM HEPES buffer at pH=8.1. The experimental diffusion-limiting membrane was identical to the control, with the additional inclusion of 10 mg/ml of $MnO_2$ (Catalog #217646, available from SIGMA-ALDRICH, headquartered in St. Louis, MO). The control and experimental diffusion-limiting membranes were allowed to cure.

The sensors were beaker tested in 100 mM PBS at a temperature of 33° C., along with two controls, in quadruplicate, separately in 1 mg/ml ascorbic acid and 5 mM glucose. The sensor current results are shown in Table 5.

TABLE 5

| | Sensor Current (nA) | | % Ascorbic Acid Interference |
|---|---|---|---|
| | 5 mM Glucose | 1 mg/ml Ascorbic Acid | |
| Control | 10.03 | 2.02 | 20.1% |
| Experimental | 11.24 | 0.89 | 7.9% |

As shown, the experimental sensors comprising the interferent-reactant species within the diffusion-limiting membrane show reduced ascorbic acid interference. Accordingly, incorporation of a metal oxide interferent-reactant species is a viable method to eliminate or reduce signal at the working electrode attributable to interferents.

Example 7. In this example, the effectiveness of incorporating a scrubbing electrode into an analyte sensor for eliminating or reducing interferent signal at the working electrode was evaluated. A glucose sensor was prepared by applying a glucose sensing active area of glucose oxidase chemistry to a working electrode. The working electrode was approximately 170 μm in width. A scrubbing electrode was incorporated by applying a layer of adhesive to create a thin layer of about 50 μm. The scrubbing electrode was approximately 2500 μm in width. No diffusion-limiting membrane was incorporated into the sensor.

The sensor was beaker tested in 1 mM glucose in 100 mM PBS at a temperature of 33° C. FIG. 20 shows the current for both the working electrode and the scrubbing electrode. As shown, the working electrode maintains a substantially stable glucose response and the scrubbing electrode exhibits no response to glucose, as expected because it comprises no glucose sensing chemistry, for upwards of two weeks, even absent the diffusion-limiting membrane. Accordingly, the diffusion-limiting function of the membrane may be achieved using a scrubbing electrode.

Figure 22:
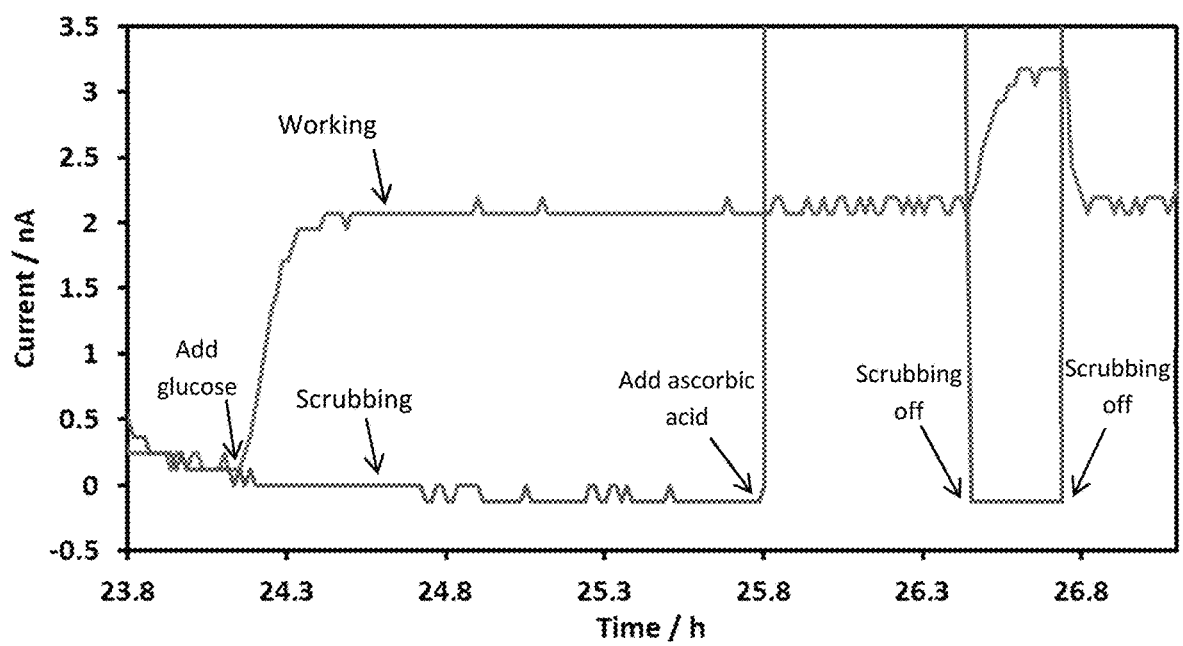
Figure 23:
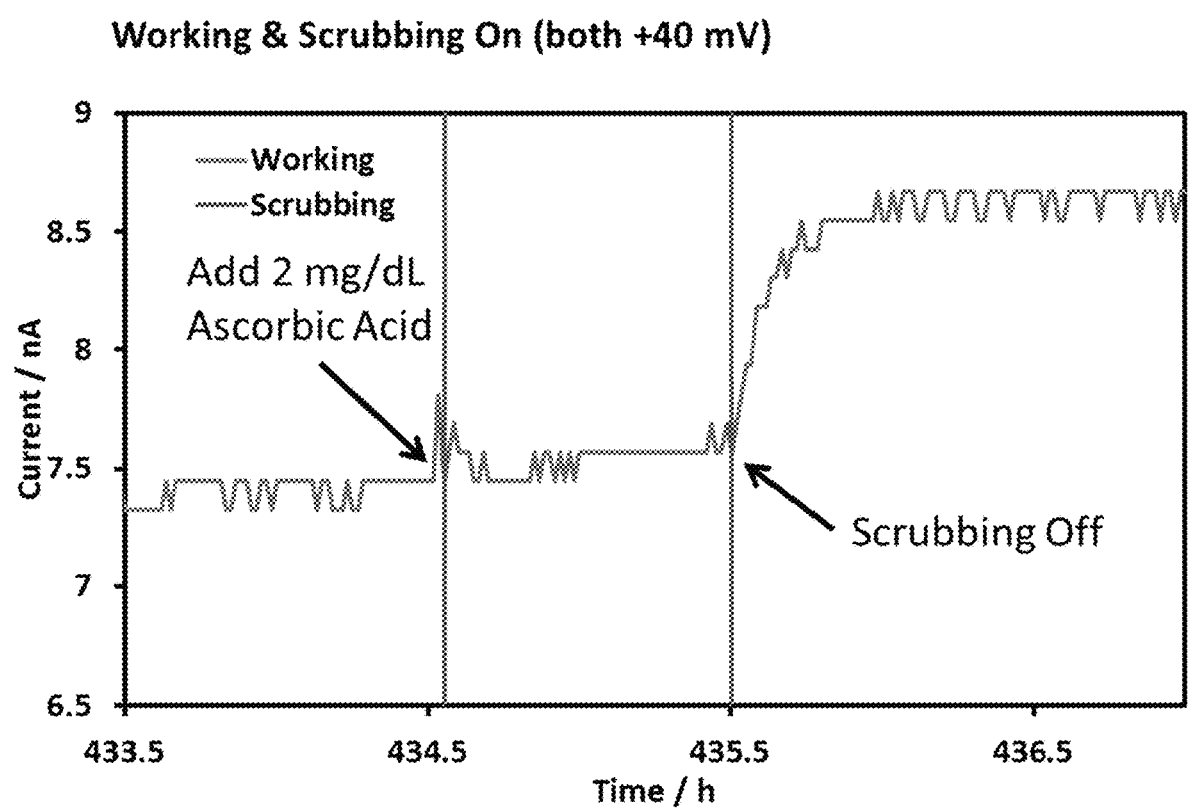

Example 8. In this example, the effectiveness of incorporating a scrubbing electrode into an analyte sensor for eliminating or reducing interferent signal at the working electrode was evaluated. The glucose sensor comprising the scrubbing electrode of Example 7 was tested in the presence of glucose and ascorbic acid, with potential applied or removed from the scrubbing electrode. When potential was applied to either the working electrode or the scrubbing electrode, the potential was +40 mV. As shown in FIG. 22, the sensor was beaker tested in 100 mM PBS at a temperature of 33° C. After approximately 24 hours, 250 µM of glucose was added and the working electrode and scrubbing electrode were observed. As shown, the working electrode peaks to a steady state upon detecting the glucose and the scrubbing electrode remains essentially unaffected. After approximately 25 hours, 2 mg/dL (114 µM) of ascorbic acid was added and, as shown, the working electrode response remained steady (detecting glucose), and the scrubbing electrode response current increased instantaneously (detecting ascorbic acid). Thereafter, the potential of the scrubbing electrode was turned off and back on again, and the comparative increase between these actions of the glucose signal may be attributed to ascorbic acid. FIG. 23 shows the sensor after approximately 18 days, demonstrating its stability over at least this time period. Accordingly, it is apparent that the scrubbing electrode is effective in removing ascorbic acid from accessing the working electrode.

Figure 24:
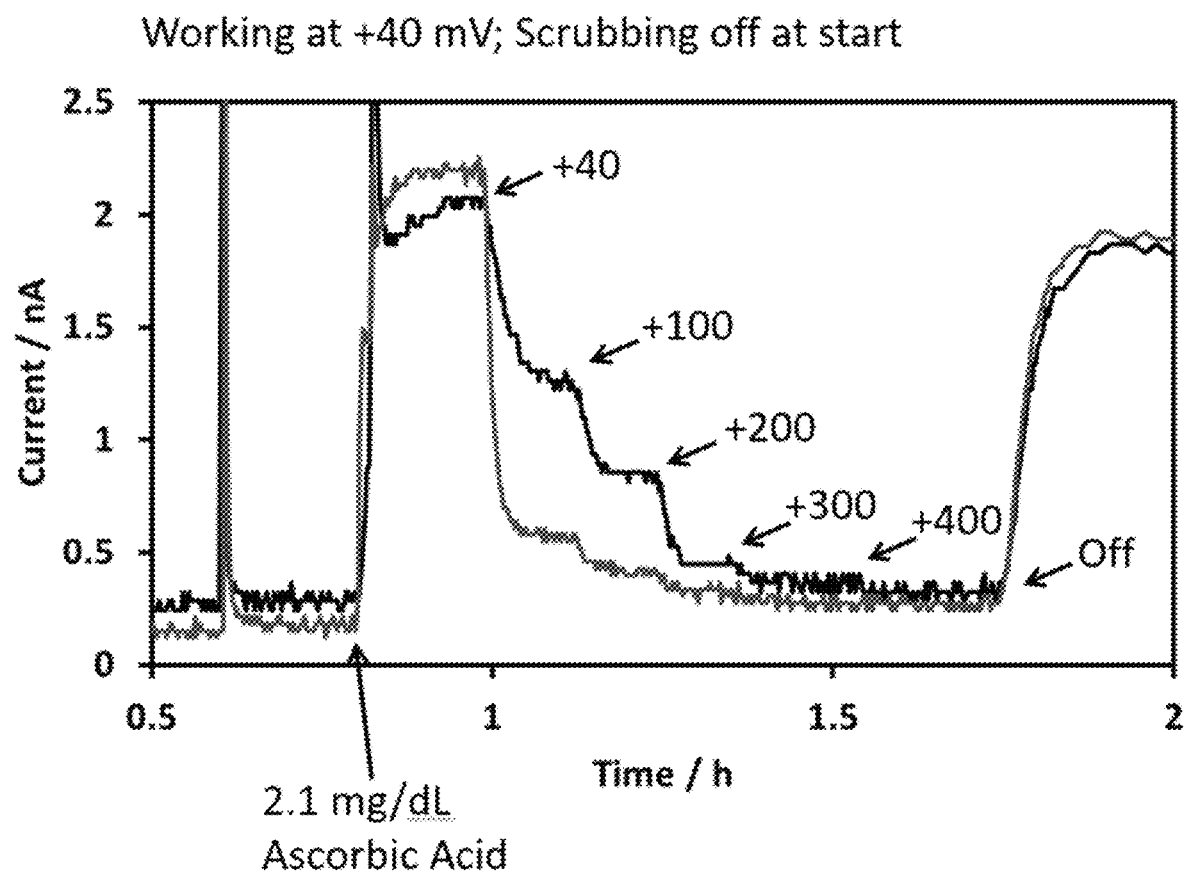

Example 9. In this example, the effectiveness of incorporating a scrubbing electrode into an analyte sensor for eliminating or reducing interferent signal at the working electrode was evaluated. Two glucose sensors comprising a scrubbing electrode were prepared according to Example 7, each having a different carbon ink type and different screen printing locations. The scrubbing electrodes were prepared by Steven Label Corporation (Santa Fe Springs, CA) (labeled "C1" in FIG. 24, the black line) and in-house (labeled "C2" in FIG. 24, the grey line). The commercial composition of the carbon inks are different (e.g., different carbon particles, different binders, and/or different ratio of carbon to binder) but exact composition is not known. Moreover, the location of screen printing was different, likely due to proprietary printing processes, temperatures, curing times, and the like. The two different sensors were beaker tested in 100 mM PBS at a temperature of 33° C. in 2.1 mg/dL ascorbic acid. The sensor currents of each of the scrubbing electrodes are shown in FIG. 24, and it is evident that the scrubbing electrode composition material, location, and potential applied to the scrubbing electrode can influence its scrubbing efficiency. Accordingly, the scrubbing electrode may be optimized in view of the interferent of interest and/or its concentration in a bodily fluid, and the like, and any combination thereof.

Example 10. In this example, the effectiveness of incorporating an analyte-permeable scrubbing electrode into an analyte sensor for eliminating or reducing interferent signal at the working electrode was evaluated. Glucose sensors comprising a carbon nanotube analyte-permeable electrode were prepared as shown in FIG. 25. The working electrode was screen printed onto a plastic substrate with surrounding wells to allow for deposited solutions of additional components of the sensor to be tested. The well is represented as the "well boundary" portions of FIG. 25. This well configuration, and variants thereof, may be used in the embodiments of the present disclosure, as described above. An active area of ketone sensing chemistry was automated liquid dispensed into the well and atop the working electrode. The sensing chemistry covered a portion of the working electrode, but excess (exposed) working electrode remained present. Thereafter, an initial diffusion-limiting membrane of 10Q5 was hand-deposited into the well atop the sensing chemistry and the excess working electrode portions. A carbon nanotube analyte-permeable scrubbing electrode was deposited into the well atop the initial 10Q5 membrane, followed by a dip-coating of the entire sensor in a second coating of 10Q5.

As shown in FIG. 26, glucose sensors comprising the carbon nanotube analyte-permeable scrubbing electrode as shown in FIG. 25 were beaker tested in 100 mM PBS. After approximately 1 hour, 5 mg/dL of ascorbate was added and the working electrode (labeled "base electrode") and scrubbing electrode (labeled "CNT electrode") were observed. As shown, the addition of the ascorbate resulted in interferent signal from the working electrode. After applying a +40 mV potential to the scrubbing electrode, the interferent signal of the working electrode decreased by ~85%. The scrubbing electrode was disconnected, and the interferent signal on the base electrode returned to previous levels. The scrubbing electrode was again connected and the potential applied was adjusted to +40, +200, and +600 mV, with modest improvements in scrubbing efficiency at higher potentials. While not shown, it was observed that various analytes of interest, including glucose and beta hydroxybutyrate, readily diffused through the scrubbing electrode to generate signal at the underlying working electrode.

Example 11. In this example, the effectiveness of incorporating an interferent-barrier membrane layer comprising a sulfonated tetrafluoroethylene based fluoropolymer-copolymer membrane, namely Nafion® into an analyte sensor for eliminating or reducing interferent signal at the working electrode was evaluated. Glucose sensors having an interferent-barrier membrane layer comprising Nafion® for reacting with ascorbic acid were prepared, as shown in FIG. 35B. A glucose sensing layer was generated on a carbon electrode by dispensing six discrete spots comprising glucose oxidase-based sensing chemistry upon the electrode. A composition comprising polyvinylpyridine and a crosslinking agent was deposited over the glucose sensing layer and the electrode to generate a mass transport limiting membrane. The sensor was then dip coated with a perfluorinated resin solution containing Nafion® in lower aliphatic alcohols and water (commercially available from Sigma-Aldrich, 274704). The experimental interferent-barrier membrane layer was allowed to cure. Control sensors were prepared in the same matter, but without the dip coated interferent-barrier membrane layer.

Figure 36A:
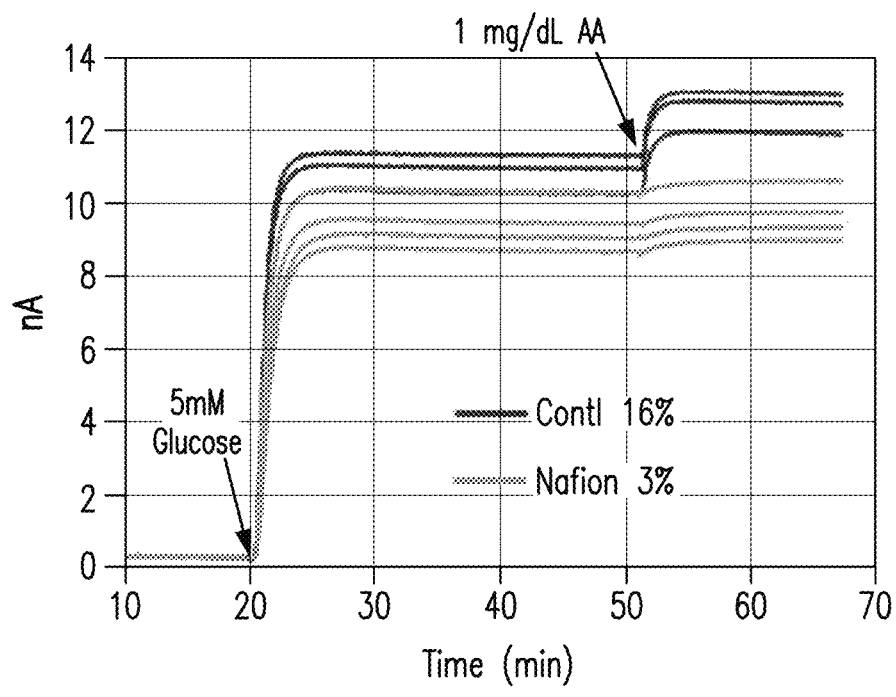
FIGS. 36A and 36B are graphs of signal versus time for analyte sensors according to one or more aspects of the present disclosure and control analyte sensors.
Figure 36B:
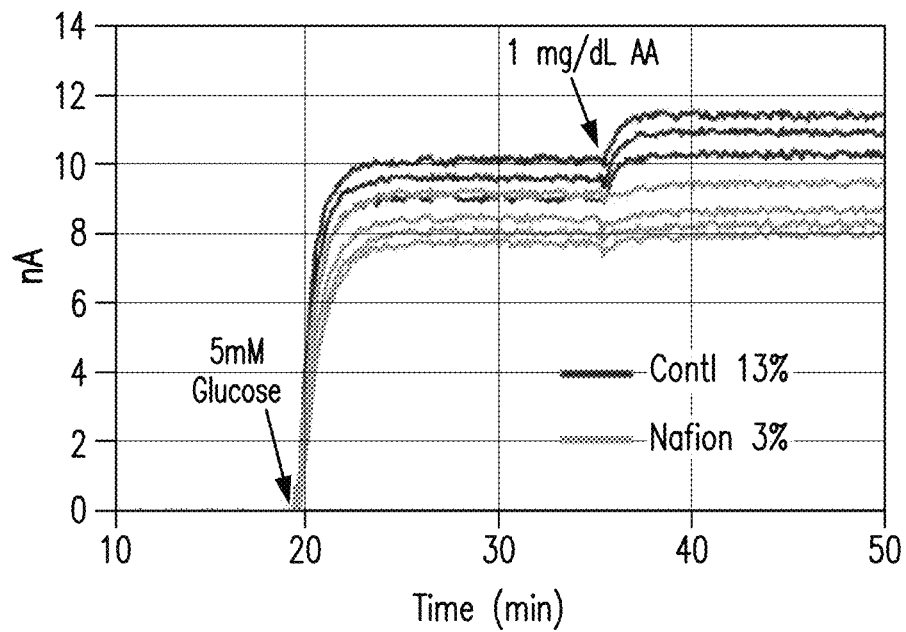

The sensors with and without the interferent-barrier membrane layer comprising Nafion® were tested in 100 mM PBS buffer, 5 mM glucose at 37° C. with 1 mg/dL ascorbic acid. The experiment was performed separately with +80 mV potential as shown in FIG. 36A and −80 mV potential as shown in FIG. 36B. Referring to FIGS. 36A and 36B, after approximately 20 minutes 5 mM glucose was added. As shown, the addition of glucose resulted in an analyte signal from the working electrode. Then, 1 mg/dL ascorbic acid was added between 35 minutes and 55 minutes. As shown, the addition of ascorbic acid resulted in an interferent signal in both the interferent-barrier membrane layer comprising Nafion® comprising sensor and the control sensor. However, as seen, the interferent signal is significantly lower for the sensor that includes the interferent-barrier membrane layer as compared to the control. The sensor current results showing the percent change after adding 1 mg/dL ascorbic acid are shown in Table 6.

TABLE 6

| Potential | Control | Sensor with interferent-barrier membrane including Nafion |
|---|---|---|
| +80 mV | 16% | 3% |
| −80 mV | 13% | 3% |

As shown, at a +80 mV potential, the amount of interference in the signal is reduced from 16% to only 3% of the total signal. Likewise, at a −80 mV potential, the amount of interference in the signal is reduced from 13% to only 3% of the total signal. Accordingly, incorporation of a sulfonated tetrafluoroethylene based fluoropolymer-copolymer (e.g., Nafion®) interferent-barrier membrane can significantly reduce interferent signal at the working electrode.

Unless otherwise indicated, all numbers expressing quantities and the like in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is:

1. An analyte sensor comprising: a working electrode including a working electrode layer having an elongate body comprising a proximal end and a distal end, the working electrode layer including a first active working electrode area, a second electrode portion, and at least one channel or well formed in the working electrode layer and electrically separating the first active working electrode area and the second electrode portion; and one or more additional electrodes, wherein the one or more additional electrodes comprise a counter electrode, a reference electrode, or both; and wherein the first active working electrode area comprises at least one sensing spot with at least one analyte responsive enzyme disposed thereupon and configured to generate a signal associated with an analyte of interest, wherein the second electrode portion is configured to reduce an overall interference to the signal attributed to one or more interferents.

2. The analyte sensor of claim 1, wherein the first active working electrode area comprises a plurality of sensing spots.

3. The analyte sensor of claim 2, wherein first and second adjacent sensing spots in the first active working electrode area are in an overlapping configuration.

4. The analyte sensor of claim 3, wherein third and fourth adjacent sensing spots in the first active working electrode area are in an overlapping configuration.

5. The analyte sensor of claim 3, wherein all the plurality of sensing spots in the first active working electrode area are in an overlapping configuration.

6. The analyte sensor of claim 3, wherein a shape of each of the plurality of sensing spots is at least one of spherical, circular, square, rectangular, triangular, conical, or elliptical, or a combination thereof.

7. The analyte sensor of claim 3, wherein first, second, and third sensing spots in the first active working electrode area are in an overlapping configuration.

8. The analyte sensor of claim 3, wherein the plurality of sensing spots in the first active working electrode area are in a linear configuration.

9. The analyte sensor of claim 3, wherein the plurality of sensing spots in the first active working electrode area are in a non-linear configuration.

10. The analyte sensor of claim 3, wherein the plurality of sensing spots in the first active working electrode area are in a grid configuration.

11. The analyte sensor of claim 3, wherein the at least one analyte responsive enzyme disposed upon the plurality of sensing spots of the first active working electrode area is a glucose responsive enzyme.

12. The analyte sensor of claim 1, wherein the at least one analyte responsive enzyme disposed on the at least one sensing spot of the first active working electrode area is a glucose responsive enzyme.

13. The analyte sensor of claim 1, wherein the at least one channel or well in the working electrode layer is U-shaped and extends from the proximal end of the elongate body on a first side of the first active working electrode area to proximate distal end of the elongate body of the working electrode layer, and back to the proximal end of the elongate body on a second side of the first active working electrode area.

14. The analyte sensor of claim 1, wherein the at least one channel or well comprises two laterally spaced apart gaps extending from the proximal end of the elongate body of the working electrode layer to the distal end of the elongate body of the working electrode layer on opposing sides of the first active working electrode area.

15. The analyte sensor of claim 1, wherein the at least one channel or well in the working electrode layer comprises a wavy pattern, a curly pattern, a curvy pattern, an undulating pattern, or a crimped pattern.

16. The analyte sensor of claim 1, wherein the at least one channel or well in the working electrode layer has a width of 1 μm to 100 μm and electrically insulates the first working electrode from the second electrode portion.

17. The analyte sensor of claim 1, wherein the at least one channel or well is formed in the working electrode layer during fabrication of the working electrode layer.

18. The analyte sensor of claim 1, wherein the at least one channel or well is laser-cut in the working electrode layer.

19. The analyte sensor of claim 1, wherein the first active working electrode area is connected to a first sensor current conductive trace and the second electrode portion of the electrode layer is not connected to a sensor current conductive trace.

20. The analyte sensor of claim 1, wherein the first active working electrode area is connected to a first sensor current conductive trace and the second electrode portion of the electrode layer is connected to a second sensor current conductive trace.

21. The analyte sensor of claim 20, wherein the second electrode portion is a scrubbing electrode configured to oxidize one or more interferents.

22. The analyte sensor of claim 21, wherein the interferent is selected from a group consisting of ascorbic acid, glutathione, uric acid, acetaminophen, isoniazid, salicylate, and combinations thereof.

23. The analyte sensor of claim 22, wherein the interferent is ascorbic acid.

24. The analyte sensor of claim 1, comprising:
a substrate, wherein the working electrode layer is disposed on the substrate; and
an interferent-barrier membrane layer disposed upon at least a portion of the sensor and comprising sulfonated tetrafluoroethylene based fluoropolymer, the interferent barrier-membrane configured to reduce an interferent signal of at least one interferent.

25. The analyte sensor of claim 24, further comprising a second membrane layer disposed upon the working electrode layer and the interferent-barrier membrane layer is disposed upon the second membrane layer.

26. The analyte sensor of claim 25, wherein the second membrane layer comprises polyvinylpyridine homopolymer or copolymer.

27. The analyte sensor of claim 26, wherein the at least one interferent is selected from a group consisting of ascorbic acid, glutathione, uric acid, acetaminophen, isoniazid, salicylate, and combinations thereof.

28. The analyte sensor of claim 27, wherein the interferent is ascorbic acid.

29. The analyte sensor of claim 28, wherein the interferent signal is reduced to 5% or less of a total signal when an electrode potential is in the range of −100 mV to +100 mV.

30. The analyte sensor of claim 29, wherein the at least one analyte responsive enzyme disposed on the at least one sensing spot of the first active working electrode area is a glucose responsive enzyme.

31. The analyte sensor of claim 28, wherein the interferent signal is reduced to 3% or less of a total signal when an electrode potential is in the range of −80 mV to +80 mV.

32. The analyte sensor of claim 25, wherein the interferent-barrier membrane layer is coated on the second membrane layer.

33. An analyte sensor comprising: a substrate having an upper surface comprising a first portion and a second exposed portion; a working electrode including a working electrode layer disposed upon the first portion of the upper surface of the substrate, the working electrode layer including an in vivo portion having a first active working electrode area comprising at least one sensing spot with at least one analyte-responsive enzyme disposed thereupon, a second electrode portion, and at least one channel or well electrically separating the first active working electrode area and the second electrode portion, wherein the second electrode portion is configured to reduce an overall interference to the signal attributed to one or more interferents; one or more additional electrodes, wherein the one or more additional electrodes comprise a counter electrode, a reference electrode, or both; and a membrane covering at least a portion of the working electrode layer and the second exposed portion of the upper surface of the substrate.

34. The analyte sensor of claim 33, wherein the substrate comprises a polymeric material selected from polyester, or polyimide.

35. The analyte sensor of claim 34, wherein the polymeric material is polyester.

36. The analyte sensor of claim 33, wherein at least a portion of the second exposed portion of the upper surface of the substrate is roughened.

37. The analyte sensor of claim 33, wherein the membrane comprises a material selected from a polymeric material, a cross-linking agent, and combinations thereof.

38. The analyte sensor of claim 37, wherein the polymeric material comprises polyvinylpyridine homopolymer or copolymer.

39. The analyte sensor of claim 33, wherein the at least one analyte responsive enzyme disposed upon the sensing spot of the first active working electrode area is a glucose responsive enzyme.

* * * * *